(12) United States Patent
Mittal et al.

(10) Patent No.: US 7,025,967 B2
(45) Date of Patent: *Apr. 11, 2006

(54) RECOMBINANT PROTEIN PRODUCTION IN BOVINE ADENOVIRUS EXPRESSION VECTOR SYSTEM

(75) Inventors: Suresh K. Mittal, West Lafayette, IN (US); Frank L. Graham, Rome (IT); Ludvik Prevec, Burlington (CA); Lorne A. Babiuk, Saskatoon (CA)

(73) Assignee: University of Saskatchewan, Saskatoon (CA)

(*) Notice: Subject to any disclaimer, the term of this patent is extended or adjusted under 35 U.S.C. 154(b) by 383 days.

This patent is subject to a terminal disclaimer.

(21) Appl. No.: 10/046,938

(22) Filed: Jan. 14, 2002

(65) Prior Publication Data

US 2002/0192185 A1 Dec. 19, 2002

Related U.S. Application Data

(63) Continuation of application No. 09/435,242, filed on Nov. 5, 1999, now Pat. No. 6,379,944, which is a continuation of application No. 08/815,927, filed on Mar. 13, 1997, now Pat. No. 6,086,890, which is a continuation of application No. 08/164,292, filed on Dec. 9, 1993, now Pat. No. 5,820,868.

(51) Int. Cl.
*A61K 39/235* (2006.01)
*A61K 39/295* (2006.01)
*C12N 7/01* (2006.01)
*C12N 15/861* (2006.01)

(52) U.S. Cl. .............. 424/199.1; 435/320.1; 435/235.1; 435/455; 435/456; 435/93.2

(58) Field of Classification Search ........... 435/320.1, 435/235.1, 69.1, 455, 456, 325; 424/199.1, 424/93.2, 233.1
See application file for complete search history.

(56) References Cited

U.S. PATENT DOCUMENTS

| | | | |
|---|---|---|---|
| 3,962,424 A | 6/1976 | Zygraich et al. |
| 4,510,245 A | 4/1985 | Cousens et al. |
| 4,920,209 A | 4/1990 | Davis et al. |

(Continued)

FOREIGN PATENT DOCUMENTS

| CA | 2012895 | 9/1990 |
|---|---|---|
| EP | 0 185 573 | 6/1986 |
| EP | 0 259 149 | 3/1988 |
| EP | 0 389 286 | 9/1990 |
| FR | 2642767 | 8/1990 |
| FR | 2657880 | 8/1991 |
| GB | 0 185 573 | 6/1986 |
| WO | WO 86/06409 | 11/1986 |
| WO | WO 91/11525 | 8/1991 |
| WO | WO 95/16048 | 6/1995 |
| WO | WO 96/22398 | 7/1996 |
| WO | WO 98/59063 | 12/1998 |
| WO | WO 01/92547 | 12/2001 |
| WO | WO 02/06502 | 1/2002 |
| WO | WO 03/040305 | 5/2003 |

OTHER PUBLICATIONS

Alley, C.D. and Mestecky, J. (1988). "The mucosal immune system" Chapter 9 *In B–lymphocytes in human diseases*. G. Bird and J.E. Calvert, eds., Oxford University Press: Oxford, pp. 222–254.

Amalfitano, A. et al. (Apr. 1996). "Improved adenovirus packaging cell lines to support the growth of replication-defective gene–delivery vectors," *Proc. Natl. Acad. Sci.. USA*, Genetics 93(8):3352–3356.

Andersson, M. et al. (1985). "Impaired Intracellular Transport of Class I MHC Angigens as a Possible Means for Adenoviruses to Evade Immune Surveillance," *Cell* 43:215–222.

Baca–Estrada, M.E. et al. (1996). "Immunogenicity of bovine herpesvirus 1 glycoprotein D in mice: Effect of antigen form on the induction of cellular and humoral immune responses," *Viral Immunol.* 9(1):11–22.

Barbeau, D. et al. (1992). "Quantitative analysis of regions of adenovirus E1A products involved in interactions with cellular proteins," *Biochem. Cell .Biol.* 70:1123–1134.

Bartha, A. (1969). "Proposal for subgrouping of bovine adenoviruses," *Acta. Vet. Acad. Sci. Hung.* 19(3):319–321.

Baxi, M.K. et al. (1998). "Characterization of bovine adenovirus type 3 early region 2B," *Virus Genes* 16(3):313–316.

Belák et al. (1986). "Subtypes of bovine adenovirus type 2 exhibit major differences in region E3," *Virology* 153:262–271.

Bellett, A.J.D. et al. (1989). "Functions of the Two Adenovirus Early E1A Proteins and Their Conserved Domains in Cell Cycle Alteration. Actin Reorganization. and Gene Activation in Rat Cells." *J. Virol.* 63(1):303–310.

Benköet al. (1990). "Molecular Cloning and physical mapping of the DNA of bovine adenovirus serotype 4: study of the DNA homology among bovine, and porcine adenoviruses," *Journal of General Virology* 71:465–469.

Berg, J.M. (1986). "Potential Metal–Binding Domains in Nucleic Acid Binding Proteins," *Science* 232:485–487.

(Continued)

*Primary Examiner*—Mary E. Mosher
(74) *Attorney, Agent, or Firm*—Morrison & Foerster LLP

(57) ABSTRACT

The present invention relates novel live bovine adenovirus (BAV) expression vector systems in which part or all of one or both of the early region 1 (E1) and early region 3 (E3) genes are deleted and replaced by a foreign gene or fragment thereof and novel recombinant mammalian cell lines stably transformed with BAV E1 sequences, and therefore, express E1 gene products capable of allowing replication therein of a bovine adenovirus having an E1 deletion replaced by a heterologous nucleotide sequence encoding a foreign gene or fragment thereof and their use in production of (antigenic) polypeptides or fragments thereof for the purpose of live recombinant virus or subunit vaccine or for other therapies.

17 Claims, 50 Drawing Sheets

U.S. PATENT DOCUMENTS

| | | |
|---|---|---|
| 5,024,939 A | 6/1991 | Gorman |
| 5,151,267 A | 9/1992 | Babiuk et al. |
| 5,756,086 A | 5/1998 | McClelland et al. |
| 5,770,442 A | 6/1998 | Wickham et al. |
| 5,820,868 A | 10/1998 | Mittal et al. |
| 5,846,782 A | 12/1998 | Wickham et al. |
| 5,871,727 A | 2/1999 | Curiel |
| 5,922,576 A | 7/1999 | He et al. |
| 6,001,591 A | 12/1999 | Mittal et al. |
| 6,086,890 A | 7/2000 | Mittal et al. |
| 6,319,716 B1 | 11/2001 | Tikoo et al. |
| 2002/0034519 A1 | 3/2002 | Tikoo et al. |
| 2002/0064859 A1 | 5/2002 | Tikoo |
| 2003/0099615 A1 | 5/2003 | Tikoo |
| 2003/0143200 A1 | 7/2003 | Tikoo |

OTHER PUBLICATIONS

Berk, A. J. et al. (1979). "Pre–Early Adenovirus 5 Gene Product Regulates Synthesis of Early Viral Messenger RNAs," *Cell* 17:935–944.

Berk, A.J (1986). "Adenovirus Promoters and E1A Trans-activation," *Ann. Rev. Genet* 20:45–79.

Berk, A.J. and Sharp, P.A. (1978). "Structure of the Adenovirus 2 Early mRNAs," *Cell.* 14:695–711.

Berkner, K.L. (1989) "Development of Adenovirus Vectors for the Expression of Heterologous Genes" *Biotechniques* 6:616–629.

Berkner, K.L. and Sharp, P.A. (1984). "Expression of dihydrofolate reductase, and of the adjacent E1b region, in an Ad5–dihydrofolate reductase recombinant virus," *Nuc. Acid Res.* 12(4):1925–1941.

Bett, A.J. et al. (1993). "Packaging Capacity and Stability of Human Adenovirus Type 5 Vectors," *J. Virol.* 67(10):5911–5921.

Birnboim, H.C. and Doly, J. (1979). "A rapid alkaline extraction procedure for screening recombinant plasmid DNA," *Nuc. Acids Res.* 7(6):1513–1523.

Boshart, M. et al. (Jun. 1985). "A very strong enhancer is located upstream of an immediate early gene of human cytomegalovirus," *Cell 41*:521–530.

Bostock, C.J. (1990). "Viruses as Vectors" *Vet. Microbiol.* 23:55–71.

Boyle et al. (1992). "Vectors for Recombinant Vaccine Delivery" *In Animal Parasite Conrol Utilizing Biotechnology*, W.K. Yong CRC Press:Boca Raton, pp. 25–47.

Boyle et al. (1993). "Recombinant fowlpox virus vaccines for poultry," *Immunol. Cell Biol.* 71:391–397.

Boyle, D.B. (1989). "How do other Poxviruses fit in as Potential Vectored Vaccine Substrates for Animal Immunizations?" *Res. Virol.* 140(5):483–491.

Branton, P.E. et al. (1985). "Transformation by Human Adenoviruses," *Biochim. Biophys. Acta* 780:67–94.

Brennan, S. and Savage, R. (1990). "Embryonic transcriptional activation of a Xenopus cytoskeletal actin gene does not require a serum response element," *Roux's Arch. Dev. Biol.* 199:89–96.

Brough, D.E. et al. (Sep. 1996). "A gene transfer vector–cell line system for complete functional complementation of adenovirus early regions E1 and E4," *J. of Virol.* 70(9):6497–6501.

Bruder, J.T. and Hearing, P. (1989). "Nuclear Factor EF–1A Binds to the Adenovirus E1A Core Enhancer Element and to Other Transcriptional Control Regions," *Mol. Cell Biol.* 9(11):5143–5153.

Burgert, H. and Kvist, S. (1985). "An Adenovirus Type 2 Glycoprotein Blocks Cell Surface Expression of Human Histocompatibility Class I Antigens," *Cell* 41:987–997.

Burgert, H. and Kvist, S. (1987). "The E3/19K protein of adenovirus type 2 binds to the domains of histocompatibility antigens required for CTL recognition," *EMBO J.* 6(7):2019–2026.

Cai, F. et al. (1990). "Nucleotide and deduced amino acid sequence of the bovine adenovirus type 3 proteinse," *Nuc. Acids Res.* 18(18):5568.

Carlin, C.R. et al. (1989). "Epidermal Growth Factor Receptor Is Down–Regulated by a 10,400 MW Protein Encoded by the E3 Region of Adenovirus," *Cell* 57:135–144.

Chanda, P.K. et al. (1990). "High Level Expression of the Envelope Glycoproteins of the Human Immunodeficiency Virus Type I in Presence of rev Gene Using Helper–Independent Adenovirus Type 7 Recombinants," *Virology* 175:535–547.

Chroboczek, J. and Jacrot, B. (1987). "The Sequence of Adenovirus Fiber: Similarities and Differences between Serotypes 2 and 5," *Virology.* 161:549–554.

Chu, G. et al. (1987). "Electroporation for the efficient transfection of mammalian cells with DNA," *Nucl. Acids Res* 15(3):1311–1327.

Cladaras, C. and Wold, W.S.M. (1985). "DNA Sequence of the Early E3 Transcription Unit of Adenovirus 5," *Virology* 140:28–43.

Conley, M.E. et al., (1987). "Intravascular and mucosal immunoglobin A: Two separate but related systems of immune defense?" *Ann. Intern. Med. 106*:892–899.

Culp, J.S. et al. (1988). "The 289–amino acid E1A protein of adenovirus binds zinc in a region that is important for trans–activation," *PNAS, USA* 85:6450–6454.

Darbyshire, J.H. (1966). "Oncogenicity of Bovine Adenovirus Type 3 in Hamsters," *Nature* 211:102.

Darbyshire, J.H. et al. (1965). "A New Adenovirus Serotype of Bovine Origin," *J. Comparative Pathology* 75:327–331.

Darbyshire, J.H. et al. (1966). "The Pathogenesis and Pathology of Infection inCalves with a Strain of Bovine Adenovirus Type 3," *Res. Vet Sci* 7:81–93.

de Wet, J.R. et al. (1987). "Firefly Luciferase Gene: Structure and Expression in Mammalian Cells," *Mol. Cell. Biol.* 7(2):725–737.

Degryse, F., (1996). "In vivo intermolecular recombination in *Escherichia coli*: Application to plasmid constructions," *Gene 170*:45–50.

Dewar, R.L. et al. (1989). "Synthesis and Processing of Human Immunodeficiency Virus Type I Envelope Proteins Encoded by a Recombinant Human Adenovirus," *J. Virol.* 63(1):129–136.

Doronin, K.K. et al. (1993). "Expression of the gene encoding secreted placental alkaline phosphatase (SEAP) by a nondefective adenovirus vector," *Gene 126*:247–250.

Dower, W.J. et al. (1988). "High efficiency transformation of *E. coli* by high voltage electroporation," *Nuc. Acids Res.* 16(13):6127–6145.

Dragulev, B.P. et al. (1991). "Sequence Analysis of Putative E3 and Fiber Genomic Regions of Two Strains of Canine Adenovirus Type 1," *Virology*, 183:298–305.

Dynan, S.W. and Tjian, R. (1983). "The Promoter–Specific Transcription Factor Sp1 Binds to Upstream Sequences in the SV40 Early Promoter," *Cell*. 35:79–87.

Dyson, N. et al. (1990). "Large T Antigens of Many Polyomaviruses Are Able To Form Complexes with the Retinoblastoma Protein," *J. Virol.* 64(3):1353–1356.

Egan, C. et al. (1989). "Binding of the Rh1 protein to E1A products is required for adenovirus transformation," *Oncogene* 4:383–388.

Elgadi, M. et al. (1993). "Sequence and sequence analysis of E1 and pIX regions of the BAV3 genome," *Intervirology* 36:113–120.

Ertl, H.C.J. and Xiang, Z. (1996). "Novel vaccine approaches," *J. Immunol.* 156:3579–3582.

Esposito et al. (1989). "Infectious Recombinant Vectored Virus Vaccines," *Adv. Vet. Sci. Comp. Med.* 33:195–247.

Fallaux, F.J. et al. (Jan. 20, 1996). "Characterization of 911: a new helper cell line for the titration and propagation of early region 1–deleted adenoviral vectors," *Human Gene Therapy* 7:215–222.

Fejér et al. (1992). "Multiple enlargements in the right inverted terminal repeat of the DNA of canine adenovirus type 2" *Acta Microbiologica Hungarica* 39:159–168.

Fitzgerald, L. et al. (1997). "Cloning and sequencing of the bovine adenovirus type 2 early region 4," *Gene* 185:181–186.

Fitzpatrick, D.R. et al. (1990). Mapping of 10 Epitopes on Bovine Herpesvirus Type I Glycoproteins gI and GIII, *Virology* 176:145–157.

Flomenberg, P.R. et al. (1988). "Sequence and Genetic Organization of Adenovirus Type 35 Early Region 3," *J. of Virology*, 62(11):4431–4437.

GenBank database under accession No. D16839.

Ghosh–Choudhury, G. et al. (1987). "Protein IX, a minor component of the human adenovirus capsid, is essential for the packaging of full length genomes," *EMBO. J.* 6(6):1733–1739.

Ginsberg, H.S. ed. (1984). *The Adenoviruses*. Plenum Press: New York, Table of Contents, pp. ix–xvii.

Ginsberg, H.S. et al. (1989). "Role of early region 3 (E3) in pathogenesis of adenovirus disease," *PNAS, USA* 86:3823–3827.

Gooding, L.R. et al. (1988). "A 14,700 MW Protein from the E3 Region of Adenovirus Inhibits Cytolysis by Tumor Necrosis Factor," *Cell* 53:341–346.

Graham, F.L. and Prevec, L. (1992) "Adenovirus–based expression vectors and recombinant vaccines" Chapter 16 *In Vaccines: New approaches to immunological problems.* R.W. Ellis ed., Butterworth–Heinemann: Stoneham, pp. 363–390.

Graham, F.L. and Prevec, L. (1991). "Manipulation of adenovirus vectors" Chapter 11 *In Methods in Molecular Biology: Gene Transfer and Expression Techniques.* Murray and Walker eds., Humana Press: Clifton, N.J., vol. 7, pp. 109–146.

Graham, F.L. and VanDerEb, A.J. (1973). "A New Technique for the Assay of Infectivity of Human Adenovirus 5 DNA," *Virology* 52:456–467.

Graham, F.L. et al. (1977). "Characteristics of a Human Cell Line Transformed by DNA from Human Adenovirus Type 5," *J. Gen. Virol.* 36:59–72.

Graham, F.L. et al. (1988). "Cloning and expression of glycoprotein genes in human adenovirus vectors," *J. Cell. Biochem.* UCLA Symposium on Molecular and Cellular Biology, Suppl. 12B Abstract F109.

Graham, F.L. et al. (1989). "Infectious circular DNA of human adenovirus type 5: regeneration of viral DNA termini from molecules lacking terminal sequences," *EMBO J.* 8(7):2077–2085.

Green, N.M. et al. (1983). "Evidence for a repeating cross–β sheet structure in the adenovirus fibre," *EMBO J.* 2(8):1357–1365.

Grunhaus, A. and Horwitz, M.S. (1992). "Adenoviruses as cloning vectors," *Sem. in Virol.* 3:237–252.

Gunning, P. et al. (1987). "A human β–actin expression vector system directs high–level accumulation of antisense transcripts," *PNAS, USA.* 84:4831–4835.

Haj–Ahmad et al. (1986). "Development of a helper–independent human adenovirus vector and its use in the transfer of the herpes simplex virus thymidine kinase gene," *J. Virol.* 57:267–274.

Harlow, E. et al. (1986). "Association on Adenovirus Early–Region 1A Proteins with Cellular Polypeptides," *Mol. Cell Biol.* 6(5):1579–1589.

Hearing, P. and Shenk, T. (1986). "The Adenovirus Type 5 E1A Enhancer Contains Two Functionally Distinct Domains: One Is Specific for E1A and the Other Modulates All Early Units in Cis," *Cell.* 45:229–236.

Henikoff, S. (1984). "Unidirectional digestion with exonuclease III creates targeted breakpoints for DNA sequencing," *Gene.* 28:351–359.

Hérissé, J. and Galibert, F. (1981). "Nucleotide sequence of the EcoR1 E fragment of adenovirus 2 genome," *Nucl. Acids Res.* 9(5):1229–1240.

Hérissé, J. et al. (1980). "Nucleotide sequence of the EcoRI D fragment of adenovirus 2 genome," *Nuc. Acids Res.* 8(10):2173–2192.

Hirt, B. (1967). "Selective extraction of polyoma DNA from infected mouse cell cultures," *J. Mol. Biol.* 26:365–369.

Holland, J.J. et al. (1979). "Evolution of Multiple Genome Mutations During Long–Term Persistent Infection by Vesicular Stomatitis Virus." *Cell* 16:495–504.

Hong, J.S. et al. (1988). "Characterization of the Early Region 3 and Fiber Genes of Ad7," *Virology* 167:545–553.

Horton, T.M. et al. (1990). "A Protein Serologically and Functionally Related to the Group C E3 14,700–Kilodalton Protein Is Found in Multiple Adenovirus Serotypes." *J. Virology.* 64(3):1250–1255.

Howe, J.A. and Bayley, S.T. (1992). "Effects of Ad5 E1A Mutant Viruses on the Cell Cycle in Relation to the Binding of Cellular Proteins Including the Retinoblastoma Protein and Cyclin A," *Virology* 186:15–24.

Howe, J.A. et al. (1990). "Retinoblastoma growth suppressor and a 300–kDa protein appear to regulate cellular DNA synthesis," *PNAS, USA* 87:5883–5887.

Hu et al. (1984). "Sequence homology between bovine and human adenoviruses," *J. Virol*, 49:604–608.

Hu, S.L. et al. (1984). "Restriction Analysis and Homology Studies of the Bovine Adenovirus 7 Genome," *J. Virol.* 51:880–883.

Hughes, G. et al. (1988). "Functional and topographical analyses of epitopes on bovine herpesvirus type 1 glycoprotein IV," *Arch. Virol.* 103:47–60.

Idamakanti, N.. (1998). "Molecular characterization of early region–3 of bovine adenovirus–3," M. Sci. Thesis, University of Saskatchewan: Saskatoon, Saskatchewan, pp. ii–92.

Imler, J. (1995). "Adenovirus vectors as recombinant viral vaccines," *Vaccine* 13(13):1143–1151.

Jelsma, T.N. et al. (1988). "Use of Deletion and Point Mutants Spanning the Coding Region of the Adenovirus 5 E1A Gene to Define a Domain that is Essential for Transcriptional Activation," *Virology* 163:494–502.

Johnson, D.C. et al. (1988). "Abundant Expression of Herpes Simplex Virus Glycoprotein gB Using an Adenovirus Vector," *Virology* 164:1–14.

Jones, N. and Shenk, T. (1979). "Isolation of adenovirus type 5 host range deletion mutants defective for transformation of rat embroy cells," *Cell* 17(3):683–689.

Kaledin, A.S. (1988). "Cloning and Sequencing of EIA gene of bovine adenovirus 3 genome," *Shornik Nauchnykh Trudov–Moskovskaya Veterinaria Akademiya* 159:78–82 (translation provided).

Kimelman, D. et al. (1985). "Ela Regions of the Human Adenoviruses and of the Highly Oncogenic Simian Adenovirus 7 Are Closely Related," *J. Virol.* 53(2):399–409.

Kit, S. et al. (1991). "Modified–live infectious bovine rhinotracheitis virus vaccine expressing monomer and dimer forms of foot–and–mouth disease capsid protein epitopes on surface of hybrid virus particles," *Arch. Virol.* 120:1–17.

Kovesdi, I. et al. (1987). "Role of an adenovirus E2 promoter binding factor in E1A–mediated coordinate gene control," *PNAS, USA*, 84:2180–2184.

Krougliak, V. and Graham, F.L. (Dec. 1995). "Development of cell lines capable of complementing E1, E4, and protein IX defective adenovirus type 5 mutants," *Human Gene Therapy* 6:1575–1586.

Kruglyak, V.A. et al. (1987). "Cloning Fragments of Virion DNA of Cattle Adenoviruses BAV 3 in pUC 19 Plasmid," *Soviet Agricultural Sciences* 11:64–67.

Kunkel, T.A. et al. (1987). "Rapid and efficient site–specific mutagenesis without phenotypic selection," *Meth. Enzymol.* 154:367–382.

Kurokawa, T. et al. (1978). "Biochemical Studies on Bovine Adenovirus Type 3 III, Cleavage maps of Viral DNA by Restriction Endonucleases EcoRI, BamHI, and HindIII," *J. Virol.* 28(1):212–218.

Laemmli, U.K. (1970). "Cleavage of Structural Proteins during the Assembly of the Head of Bacteriophage T4," *Nature* 227:680–685.

Lee, J.B. et al. (1998). "Genetic organization and DNA sequence of early region 4 of bovine adenovirus type 3," *Virus Gene* 17:99–100.

Lee, W. et al. (1987). "Activation of transcription by two factors that bind promoter and enhancer sequences of the human metallothionein gene and SV40," *Nature* 325:368–372.

Liang, X. et al. (1993). "Identification and Deletion Mutagenesis of the Bovine Herpesvirus I dUTPase Gene and a Gene Homologous to Herpes Simplex Virus UL49.5," *Virology* 195:42–50.

Lillie, J.W. and Green, M.R. (1989). "Transcription activation by the adenovirus E1a protein," *Nature* 338:39–44.

Lillie, J.W. et al. (1986). "An Adenovirus E1a Protein Region Required for Transformation and Transcriptional Repression," *Cell* 46:1043–1051.

Lubeck, M.D. et al. (1989). "Immunogenicity and efficacy testing in chimpanzees of an oral hepatitis B vaccine based on live recombinant adenovirus," *PNAS, USA*. 86:6763–6767.

Mattson, D.E. et al. (1988). "Bovine adenovirus type–3 Infection in Feedlot Calves," *Am. J. Vet Res.* 49(1):67–69.

McDermott, M.R. et al. (1989). "Protection of Mice Against Lethal Challenge with Herpes Simplex Virus by Vaccination with an Adenovirus Vector Expressing HSV Glycoprotein B," *Virology* 169:244–247.

McKnight, S.L. Kingsbury, R. (1982). "Transcriptional Control Signals of a Eukaryotic Protein–Coding Gene," *Science* 217:316–324.

McLorie, W. et al. (1991). "Individual adenovirus E1B proteins induce transformation independently but by additive pathways," *J. Gen Virol.* 72:1467–1471.

Mittal, S.K. et al. (1992). "Sequence analysis of bovine adenovirus type 3 early region 3 and fibre protein genes," *J. Gen. Virol.* 73:3295–3300.

Mittal, S.K. et al. (1992). "Sequence analysis of bovine adenovirus type 3 early region 3 and fibre protein genes," *J. Gen. Virol.* 74:2825 (Corrections of Mittal (1992) *J. Gen. Virol.* 73:3295–3300).

Mittal, S.K. et al. (1993). "Monitoring foreign gene expression by a human adenovirus–based vector using the firefly luciferase gene as a reporter," *Virus Res.* 28:67–90.

Mittal, S.K. et al. (1995). "Development of a bovine adenovirus type 3–based expression vector," *J. Gen. Virol.* 76:93–102.

Mittal, S.K. et al. (1995). "Pathogenesis and immunogenicity of Bovine Adenovirus Type 3 in Cotton rats (*Sigmodon hispidus*)," *Virology* 213:131–139.

Mittal, S.K. et al. (1996). "Induction of systemic and mucosal immune responses in cotton rats immunized with human adenovirus type 5 recombinants expressing the full and truncated forms of bovine herpesvirus type 1 glycoprotein gD," *Virology* 222:299–309.

Mittal, S.K. et al. (1996). "Pathology and immunogenicity in the cotton rat (*Sigmoodon hispidus*) model after infection with a bovine adenovirus type 3 recombinant virus expressing the firefly luciferase gene," *J. General Virology* 77:1–9.

Morin, J.E. et al. (1987). "Recombinant adenovirus induces antibody response to hepatitis B virus surface antigen in hamsters," *PNAS, USA* 84:4626–4630.

Moss, B. (1990). "Recombinant DNA virus vectors for vaccination," *Semin. Immunol.* 2:317–327.

Motoi, M. et al. (1972). "Neoplastic transformation of hamster cells in vitro by Bovine adenovirus Type–3," *Gann* 63:415–418.

Murphy, R.R. (1994). "Mucosal immunity to viruses," Chapter 29 In *Handbook of mucosal immunology*. P.L. Ogra et al. eds., Academic Press: San Diego, pp. 333–343.

Nevins, J.R. (1981). "Mechanisms of Activation of Early Viral Transcription by the Adenovirus E1A Gene Product," *Cell* 26:213–220.

Nevins, J.R. (1982). "Induction of the Synthesis of a 70,000 Dalton Mammalian Heat Shock Protein by the Adenovirus E1A Gene Product," *Cell* 29:913–919.

Niiyama, Y. et al. (1975). "Biochemical studies on bovine adenovirus type 3," *Virol.* 16(3):621–633.

Ojkic, D. et al. (1997). "Sequence analysis of the terminal protein precursor coding regions from bovine adenovirus serotypes 2 and 3," *Intervirology* 40:253–262.

Ojkie, D. et al. (May 4–8, 1997). "Sequencing analysis of the coding regions for the terminal protein precursor of bovine adenovirus serotypes 2 and 3," *Abstracts of the 97th General Meeting of the American Society for Microbiology*, Division S: DNA Viruses, Part 114–S "Viral strain variation: detection and molecular and biologic properties," Abstract No. S–2a, p. 532.

Orkin, S.H. and Motulsky, A.G. (Dec. 7, 1995). "Report and recommendations of the panel to assess the NIH investment in research on gene therapy" <http://www.nih.gov/news/panelrep.html>, visited Aug. 8, 2000, 40 pages.

Papp, Z. et al. (1997). "Mucosal immunization with recombinant adenoviruses: Induction of immunity and protection of cotton rats against respiratory bovine herpesvirus type 1 infection," *J. Gen. Virol*, 78:2933–2943.

Philipson, L. (1983). "Structure and Assembly of Adenoviruses." *Current Topics in Microbiology and Immunology* 109:1–52.

Prevec, L. et al. (1989). "Use of human adenovirus–based vectors for antigen expression in animals" *J. Gen. Virol*. 70:429–434.

Prevec, L. et al. (1990). "A Recombinant Human Adenovirus Vaccine against Rabies," *J. Inf. Dis*. 161:27–30.

Ragot, T. et al. (1993). "Efficient adenovirus–mediated transfer of a human minidystrophin gene to skeletal muscle of mdx mice," *Nature* 361:647–650.

Raviprakash, K.S. et al. (1989). "The Mouse Adenovirus Type 1 Contains an Unusual E3 Region," *J. Virology* 63(12):5455–5458.

Reddy, P.S. et al. (1998). "Nucleotide sequence, genome organization, and transcription map of bovine adenovirus type 3," *J. Virol* 72(2):1394–1402.

Reddy, P.S. et al. (1999). "Replication–defective bovine adenovirus type 3 as an expression vector," *J. Virol*. 73(11):9137–9144.

Rosenfeld, M.A. et al. (1991). "Adenovirus–Mediated Transfer of a Recombinant αl–Antitrypsin Gene to the Lung Epithelium in Vivo," *Science* 252:431–434.

Rosenfeld, M.A. et al. (1992). "In Vivo Transfer of the Human Cystic Fibrosis Transmembrane Conductance Regulator Gene to the Airway Epithelium," *Cell* 68:143–155.

Rouse, B.T. and Babiuk, L.A. (1974). "Host response to infectious bovine rhinotracheitis virus," *J. Immunol*. 113(5):1391–1398.

Sanger, F. et al. (1977). "DNA sequencing with chain–terminating inhibitors," *PNAS, USA* 74(12):5463–5467.

Schneider, M. et al. (1989). "Expression of the Glycoprotein of Vesicular Stomatitis Virus by Infectious Adenovirus Vectors," *J. Gen. Virol*. 70:417–427.

Shinagawa, M. et al. (1987). "Phylogenetic relationships between adenoviruses as inferred from nucleotide sequences of inverted terminal repeats," *Gene* 55:85–93.

Signäs, C. et al. (1985). "Adenovirus 3 Fiber Polypeptide Gene: Implications for the Structure of the Fiber Protein," *J. Virology* 53(2):672–678.

Signäs, C. et al. (1986). "Region E3 of Human adenoviruses: differences between the oncogenic adenovirus–3 and the non–oncogenic adenovirus–2," *Gene* 50:173–184.

Song, B. et al. (1996). "Conservation of DNA sequence in the predicted major late promoter regions of selected mastadenoviruses," *Virology* 220:390–401.

Southern, E.M. (1975). "Detection of Specific Sequences Among DNA Fragments Separated by Gel Electrophoresis," *J. Mol. Biol*. 98:503–517.

Southern, P.J. and Berg, P. (1982). "Transformation of Mammalian Cells to Antibiotic Resistance with a Bacterial Gene Under Control of the SV40 Early Region Promoter," *J. Mol. Appl. Genet* 1:327–341.

Spibey, N. et al. (1989). "Identification and nucleotide sequence of the early region 1 from canine adenovirus types 1 and 2," *Virus Research* 14:241–256.

Stephens, C. and Harlow, E. (1987). "Differential splicing yields novel adenovirus 3 E1A mRNAs that encode 30 kd and 35 kd proteins," *EMBO J*. 6(7):2027–2035.

Stratford–Perricaudet, I..D. et al. (1990). "Evaluation of the Transfer and Expression in Mice of an Enzyme–Encoding Gene Using a Human Adenovirus Vector," *Hum. Gene. Ther*. 1:241–256.

Subramani, S. and Southern, P.J. (1983). "Analysis of Gene Expression Using Simian Virus 40 Vectors," *Anal. Biochem*. 135:1–15.

Thomsen, D.R. et al. (1987). "Pseudorabies virus as a live virus vector for expression of foreign genes," *Gene* 5:261–265.

Tikoo, S.K. et al. (1990). "Molecular Cloning, Sequencing, and Expression of Functional Bovine Herpesvirus 1 Glycoprotein gIV in Transfected Bovine Cells," *J. Virol*. 64:5132–5142.

Tikoo, S.K. et al. (1993). "Analysis of bovine herpesvirus 1 glycoprotein gIV truncations and deletions expressed by recombinant vaccinia viruses," *J. Virol*. 67(4):2103–2109.

Tollefson, A.E. et al. (1991). "The 10,400– and 14,500–Dalton Proteins Encoded by Region E3 of Adenovirus Form a Complex and Function Together To Down–Regulate the Epidermal Growth Factor Receptor," *J. Virol*. 65(6):3095–3105.

Tsukamoto, K. and Sugino, Y. (1972). "Nonproductive Infection and Induction of Cellular Deoxyribonucleic Acid Synthesis by Bovine Adenovirus Type 3 in a Contact–Inhibited Mouse Cell Line," *J. Virol*. 9(3):465–473.

Verma, I.M. and Somia, N. (1997). "Gene therapy– promises, problems and prospects," *Nature* 389:239–242 .

Whyte, P. et al. (1988). "Association Between an Oncogene and an Anti–Oncogene: the Adenovirus E1A proteins bind to the Retinoblastoma gene product," *Nature* 334:124–129.

Whyte, P. et al. (1988). "Two Regions of the Adenovirus Early Region 1A Proteins Are Required for Transformation," *J. Virol*. 62(1):257–265.

Wold, W.S.M. and Gooding. L.R. (1989). "Adenovirus Region E3 Proteins that Prevent Cytolysis by Cytotoxic T Cells and Tumor Necrosis Factor," *Mol. Biol. Med*. 6:433–452.

Wold, W.S.M. and Gooding, L.R. (1991). "Region E3 of Adenovirus: A Cassette of Genes Involved in Host Immunosurveillance and Virus–Cell Interactions," *Virology* 184:1–8.

Xu, Z.Z. et al. (1995). "Investigation of promoter function in human and animal cells infected with human recombinant adenoviruses expressing rotavirus antigen VP7sc," *J. Gene Virol*. 76:1971–1980.

Xu, Z.Z. et al. (1997). "Construction of ovine aenovirus recombinants by gene insertion or deletion of related terminal region sequences," *Virol*. 230:62–71.

Yagubi, A. et al. (May 4–8, 1997). "Sequencing analysis of the region encoding the DNA polymerase of bovine adenovirus serotypes 2 and 3," *Abstracts of the 97th General Meeting of the American Society for Microbiology*, Division S: DNA Viruses, Part 114–S: Viral strain variation: detection and molecular and biologic properties, Abstract No. S–2b, p. 532.

Yanisch–Perron, C. et al. (1985). "Improved M13 phage cloning vectors and host strains: nucleotide sequences of the M13mp18 and pUC19 vectors." *Gene* 33:103–119.

Yee, S. and Branton, P.E. (1985). "Detection of Cellular Proteins Associated with Human Adenovirus Type 5 Early Region 1A Polypeptides," *Virology* 147:142–153.

Yuasa, T. et al. (1991). "Preferential expression of the large hepatitis B virus surface antigen gene by an adenovirus–hepatitis B virus recombinant," *J. Gen. Virol.* 72:1927–1934.

Zerler, B. et al. (1987). "Different Functional Domains of the Adenovirus E1A Gene Are Involved in Regulation of Host Cell Cycle Products," *Mol. Cell Biol.* 7(2):821–829.

Zheng, B. et al. (1994). "The E1 sequence of bovine adenovirus type 3 and complementation of human adenovirus type 5 E1A function in bovine cells," *Virus Res.* 31:163–186.

Zoller, M.J. and Smith, M. (1982). "Oligonucleotide–direct mutagenesis using M13–derived vectors: An efficient and general procedure for the production of point mutations in any fragment of DNA," *Nucl. Acids Res.* 10(20):6487–6500.

```
         10         20         30         40         50         60
CATCATCAAT AATCTACAGT ACACTGATGG CAGCGGTCCA ACTGCCAATC ATTTTTGCCA 70         80         90        100        110        120
CGTCATTTAT GACGCAACGA CGGCGAGCGT GGCGTGCTGA CGTAACTGTG GGGCGGAGCG 130        140        150        160        170        180
CGTCGCGGAG GCGGCGGCGC TGGGCGGGGC TGAGGGGGGG GGGGCGGGCG CGCGGGGCGG 190        200        210        220        230        240
CGGCGGGGGC GGGGCGGAGGG GCGGAGTTCC GCACCCGCTA CGTCATTTTC AGACATTTTT 250        260        270        280        290        300
TAGCAAAATT GCGCCTTTTG CAAAGCATTT TCTCACATTT CAGGTATTTA GAGGGCGGAT 310        320        330        340        350        360
TTTTGGTGTT CGTACTTCCG TGTCACATAG TTCACTGTCA ATCTTCATTA CGGCTTAGAC 370        380        390        400        410        420
AAATTTTCGG CGTCTTTTCC GGGTTTATGT CCCCGGTCAC CTTTATGACT GTGTGAAACA 430        440        450        460        470        480
CACCTGCCCA TTGTTTACCC TTGGTCAGTT TTTTCGTCTC CTAGGGTGGG AACATCAAGA
```

FIG. IA

```
                490         500         510         520         530         540
         ACAAAATTGC CGAGTAATTG TGCACCTTTT TCCGGCGTTAG GACTGCGTTT CACACGTAGA 550         560         570         580         590         600
         CAGACTTTTT CTCATTTTCT CACACTCCGT CGTCCGCTTC AGAGCTCTGC GTCTTCGCTG 610         620         630         640         650
         CCACC ATG AAG TAC CTG TGT CTC GTT CTC AAC GAC GGC ATG AGT CGA ATT GAA
                Met Lys Tyr Leu Val Leu Val Leu Asn Asp Gly Met Ser Arg Ile Glu 660         670         680         690         700
         AAA GCT CTC CTG TGC AGC GAT GGT GAG GTG GAT TTA GAG TGT CAT GAG GTA
         Lys Ala Leu Leu Cys Ser Asp Gly Glu Val Asp Leu Glu Cys His Glu Val 710         720         730         740         750
         CTT CCC CCT TCT CCC GCG CCT GTC CCC GCT TCT GTG TCA CCC GTG AGG AGT
         Leu Pro Pro Ser Pro Ala Pro Val Pro Ala Ser Val Ser Pro Val Arg Ser 760         770         780         790         800
         CCT CCT CCT CTG TCT CCG GTG TTT CCT CCG TCT CCG CCA GCC CCG CTT GTG
         Pro Pro Pro Leu Ser Pro Val Phe Pro Pro Ser Pro Pro Ala Pro Leu Val 810         820         830         840         850
         AAT CCA GAG GCG AGT TCG CTG CAG CAG TAT CGG AGA GAG CTG TTA GAG
         Asn Pro Glu Ala Ser Ser Leu Gln Gln Tyr Arg Arg Glu Leu Leu Glu
```

FIG. 1B

```
860                 870                 880                 890                 900
AGG AGC CTG CTC CGA ACG GCC GAA GGT CAG CAG CGT GCA GTG TGT CCA TGT
Arg Ser Leu Leu Arg Thr Ala Glu Gly Gln Gln Arg Ala Val Cys Pro Cys 910                 920                 930                 940                 950
GAG CGG TTG CCC GTG GAA GAG GAT GAG TGT CTG AAT GCC GTA AAT TTG CTG
Glu Arg Leu Pro Val Glu Glu Asp Glu Cys Leu Asn Ala Val Asn Leu Leu 960                 970                 980                 990                 1000                1010
TTT CCT GAT CCC TGG CTA AAT GCA GCT GAA AAT GGG GGT GAT ATT TTT AAG
Phe Pro Asp Pro Trp Leu Asn Ala Ala Glu Asn Gly Gly Asp Ile Phe Lys 1020                1030                1040                1050                1060
TCT CCG GCT ATG TCT CCA GAA CCG TGG ATA GAT TTG TCT AGC TAC GAT AGC
Ser Pro Ala Met Ser Pro Glu Pro Trp Ile Asp Leu Ser Ser Tyr Asp Ser 1070                1080                1090                1100                1110
GAT GTA GAA GAG ACT AGT CAC TTT TTT CTG GAT TGC CCT GAA GAC CCC
Asp Val Glu Glu Thr Ser His Phe Phe Leu Asp Cys Pro Glu Asp Pro 1120                1130                1140                1150                1160
AGT CGG GAG TGT TCA TCT TGT GGG TTT CAT CAG GCT CAA AGC GGA ATT CCA
Ser Arg Glu Cys Ser Ser Cys Gly Phe His Gln Ala Gln Ser Gly Ile Pro
```

FIG. 1C

```
                    1170           1180           1190           1200           1210
               GGC ATT ATG TGC AGT TTG TGC TAC ATG CGC CAA ACC TAC CAT TGC ATC TAT
               Gly Ile Met Cys Ser Leu Cys Tyr Met Arg Gln Thr Tyr His Cys Ile Tyr 1220           1230           1240           1250           1260           1270
       A [GTAAG TACATTCTGT AAAAGAACAT CTTGGTGATT TCTAGTATT GTTTAGGGAT
       s 1280           1290           1300           1310           1320           1330
       TAACTGGGTG GAGTGATCTT AATCCGGCAT AACCAAATAC ATGTTTTCAC AG]GT CCA GTT
                                                                    er Pro Val 1340           1350           1360           1370           1380           1390
       TCT GAA GAG GAA ATG TGAGT CATGTTGACT TTGGGCGCG A AGAGGAAATG TGAGTCATGT
       Ser Glu Glu Glu Met End 1400           1410           1420           1430           1440           1450
       TGACTTTGGC GCGCCCTACG GTGACTTTAA AGCAATTTGA GGATCACTTT TTTGTTAGTC 1460           1470           1480           1490           1500
       GCTATAAAGT AGTCACGGAG TCTTTC ATG GAT CAC TTA AGC GTT CTT TTG GAT TTG
                                    Met Asp His Leu Ser Val Leu Leu Asp Leu 1510           1520           1530           1540           1550
       AAG CTG CTT CGC TCT ATC GTA GCG GGG GCT TCA AAT CGC ACT GGA GTG TGG
       Lys Leu Leu Arg Ser Ile Val Ala Gly Ala Ser Asn Arg Thr Gly Val Trp
```

FIG. 1D

```
1560                        1570                        1580                        1590                        1600
AAG AGG CGG CTG TGG CTG GGA CGC CTG ACT CAA CTG GTC CAT GAT ACC TGC
Lys Arg Arg Leu Trp Leu Gly Arg Leu Thr Gln Leu Val His Asp Thr Cys 1610                        1620                        1630                        1640                        1650
GTA GAG AAC GAG AGC ATA TTT CTC AAT TCT CTG CCA GGG AAT GAA GCT TTT
Val Glu Asn Glu Ser Ile Phe Leu Asn Ser Leu Pro Gly Asn Glu Ala Phe 1660                        1670                        1680                        1690                        1700
TTA AGG TTG CTT CGG AGC TAT TTT GAA GTG TTT GAC GTG TTT GTG GTG
Leu Arg Leu Leu Arg Ser Gly Tyr Phe Glu Val Phe Asp Val Phe Val Val 1710                        1720                        1730                        1740                        1750                1760
CCT GAG CTG CAT CTG GAC ACT CCG GGT CGA GTG GTC GCC GCT CTT GCT CTG
Pro Glu Leu His Leu Asp Thr Pro Gly Arg Val Val Ala Ala Leu Ala Leu 1770                        1780                        1790                        1800                        1810
CTG GTG TTC ATC CTC AAC GAT GCT AAT TCT GCT TCT TCA GGC TTT
Leu Val Phe Ile Leu Asn Asp Leu Asp Ala Asn Ser Ala Ser Ser Gly Phe 1820                        1830                        1840                        1850                        1860
GAT TCA GGT TTT CTC GTG GAC CGT CTC TGC GTG CTA TGG CTG CCG AAG GCC
Asp Ser Gly Phe Leu Val Asp Arg Leu Cys Val Pro Leu Trp Leu Lys Ala

Met Ala Glu Gly
```

FIG. 1E

```
                    1870      1880          1890         1900         1910
AGG GCG TTC AAG ATC ACC CAG AGC TCC AGG AGC ACT TCG CAG CCT TCC TCG
Arg Ala Phe Lys Ile Thr Gln Ser Ser Arg Ser Thr Ser Gln Pro Ser Ser
Gln Gly Val Gln Asp His Pro Glu Leu Gln Glu His Phe Ala Ala Phe Leu 1920         1930         1940         1950         1960
TCG CCC GAC AAG ACG ACC CAG ACT ACC AGC CAG TA GAC GGG GAC AGC CCA
Ser Pro Asp Lys Thr Thr Gln Thr Thr Ser Gln End
Val Ala Arg Gln Asp Asp Pro Asp Tyr Gln Pro Val Asp Gly Asp Ser Pro 1970         1980         1990         2000         2010
CCC CGG GCT AGC CTG GAG GAG GCT GAA CAG AGC ACT CGT TTC GAG CAC
Pro Arg Ala Ser Leu Glu Glu Ala Glu Gln Ser Thr Arg Phe Glu His 2020         2030         2040         2050         2060
ATC AGT TAC CGA GAC GTG GTG GAT GAC TTC AAT AGA TGC CAT GAT GTT TTT
Ile Ser Tyr Arg Asp Val Val Asp Asp Phe Asn Arg Cys His Asp Val Phe 2070         2080         2090         2100         2110
TAT GAG AGG TAC AGT TTT GAG GAC ATA AAG AGC TAC GAG GCT TTG CCT GAG
Tyr Glu Arg Tyr Ser Phe Glu Asp Ile Lys Ser Tyr Glu Ala Leu Pro Glu
```

FIG. 1F

```
2120                2130                2140                2150                2160
GAC AAT TTG GAG CAG CTC ATA GCT ATG CAT GCT AAA ATC AAG CTG CCC
Asp Asn Leu Glu Gln Leu Ile Ala Met His Ala Lys Ile Lys Leu Pro 2170                2180                2190                2200                2210
GGT CGG GAG TAT GAG TTG ACT CAA CCT TTG AAC ATA ACA TCT TGC GCC TAT
Gly Arg Glu Tyr Glu Leu Thr Gln Pro Leu Asn Ile Thr Ser Cys Ala Tyr 2220                2230                2240                2250                2260
GTG CTC GGA AAT GGG GCT ACT ATT AGG GTA ACA GGG GAA GCC TCC CCG GCT
Val Leu Gly Asn Gly Ala Thr Ile Arg Val Thr Gly Glu Ala Ser Pro Ala 2270                2280                2290                2300                2310                2320
ATT AGA GTG GGG GCC ATG GCC GTG GGT CCG TGT GTA ACA GGA ATG ACT GGG
Ile Arg Val Gly Ala Met Ala Val Gly Pro Cys Val Thr Gly Met Thr Gly 2330                2340                2350                2360                2370
GTG ACT TTT GTG AAT TGT AGG TTT GAG AGA GAG TCA ACA ATT AGG GGG TCC
Val Thr Phe Val Asn Cys Arg Phe Glu Arg Glu Ser Thr Ile Arg Gly Ser 2380                2390                2400                2410                2420
CTG ATA CGA GCT TCA ACT CAC GTG CTG TTT CAT GGC TGT TAT TTT ATG GGA
Leu Ile Arg Ala Ser Thr His Val Leu Phe His Gly Cys Tyr Phe Met Gly
```

FIG. 1G

```
      2430              2440              2450              2460              2470
ATT ATG GGC ACT TGT ATT GAG GTG GGG GCG GGA GCT TAC ATT CGG GGT TGT
Ile Met Gly Thr Cys Ile Glu Val Gly Ala Gly Ala Tyr Ile Arg Gly Cys 2480              2490              2500              2510              2520
GAG TTT GTG GGC TGT TAC CGG GGA ATC TGT TCT ACT TCT AAC AGA GAT ATT
Glu Phe Val Gly Cys Tyr Arg Gly Ile Cys Ser Thr Ser Asn Arg Asp Ile 2530              2540              2550              2560              2570
AAG GTG AGG CAG TGC AAC TTT GAC AAA TGC TTA CTG GGT ATT ACT TGT AAG
Lys Val Arg Gln Cys Asn Phe Asp Lys Cys Leu Leu Gly Ile Thr Cys Lys 2580              2590              2600              2610              2620
GGG GAC TAT CGT CTT TCG GGA AAT GTG TGT TCT GAG ACT TTC TGC TTT GCT
Gly Asp Tyr Arg Leu Ser Gly Asn Val Cys Ser Glu Thr Phe Cys Phe Ala 2630              2640              2650              2660              2670
CAT TTA GAG GGA GAG GGT TTG GTT AAA AAC ACA GTC AAG TCC CCT AGT
His Leu Glu Gly Glu Gly Leu Val Lys Asn Thr Val Lys Ser Pro Ser 2680              2690              2700              2710              2720
CGC TGG ACC AGC GAG TCT GGC TTT TCC ATG ATA ACT TGT GCA GAC GGC AGG
Arg Trp Thr Ser Glu Ser Gly Phe Ser Met Ile Thr Cys Ala Asp Gly Arg
```

FIG. 1H

```
2730        2740              2750              2760              2770
GTT ACG CCT TTG GGT TCC CTC CAC ATT GTG GGC AAC CGT TGT AGG CGT TGG
Val Thr Pro Leu Gly Ser Leu His Ile Val Gly Asn Arg Cys Arg Arg Trp 2780        2790              2800              2810          2820        2830
CCA ACC ATG CAG GGG AAT GTG TTT ATC ATG TCT AAA CTG TAT CTG GGC AAC
Pro Thr Met Gln Gly Asn Val Phe Ile Met Ser Lys Leu Tyr Leu Gly Asn 2840              2850              2860              2870        2880
AGA ATA GGG ACT GTA GCC CTG CCC CAG TGT GCT TTC TAC AAG TCC AGC ATT
Arg Ile Gly Thr Val Ala Leu Pro Gln Cys Ala Phe Tyr Lys Ser Ser Ile 2890              2900              2910              2920            2930
TGT TTG GAG GAG AGG ACA AAC AAG CTG GTC TTG GCT TGT GCT TTT GAG
Cys Leu Glu Glu Arg Thr Asn Lys Leu Val Leu Ala Cys Ala Phe Glu 2940              2950              2960              2970            2980
AAT AAT GTA CTG GTG TAC AAA GTG CTG AGA CGG GAG AGT CCC TCA ACC GTG
Asn Asn Val Leu Val Tyr Lys Val Leu Arg Arg Glu Ser Pro Ser Thr Val 2990            3000              3010              3020          3030
AAA ATG TGT GTT TGT GGG ACT TCT CAT TAT GCA AAG CCT TTG ACA CTG GCA
Lys Met Cys Val Cys Gly Thr Ser His Tyr Ala Lys Pro Leu Thr Leu Ala
```

FIG. 1I

```
         3040            3050            3060            3070            3080
ATT ATT TCT TCA GAT ATT CGG GCT AAT CGA TAC ATG TAC ACT GTG GAC TCA
Ile Ile Ser Ser Asp Ile Arg Ala Asn Arg Tyr Met Tyr Thr Val Asp Ser 3090            3100            3110            3120            3130            3140
ACA GAG TTC ACT TCT GAC GAG GAT T AAAAGTGGGC GGGGCCAAGA GGGGTATAAA
Thr Glu Phe Thr Ser Asp Glu Asp End 3150         3160         3170         3180         3190         3200
TAGGTGGGGA GGTTGAGGGG AGCCGTAGTT TCTGTTTTTC CCAGACTGGG GGGGACAAAC ATG
                                                                    Met 3210            3220            3230            3240            3250
GCC GAG GAA GGG CGC ATT TAT GTG CCT TAT GTA ACT GCC CGC CTG CCC AAG
Ala Glu Glu Gly Arg Ile Tyr Val Pro Tyr Val Thr Ala Arg Leu Pro Lys 3260            3270            3280            3290            3300
TGG TCG GGT TCG GTG CAG GAT AAG ACG GGC TCG AAC ATG TTG GGG GGT GTG
Trp Ser Gly Ser Val Gln Asp Lys Thr Gly Ser Asn Met Leu Gly Gly Val 3310            3320            3330            3340            3350
GTA CTC CCT CCT AAT TCA CAG GCG CAC CGG ACG GAG ACC GTG GGC ACT GAG
Val Leu Pro Pro Asn Ser Gln Ala His Arg Thr Glu Thr Val Gly Thr Glu
```

FIG. 1J

```
       3360              3370              3380              3390              3400
GCC ACC AGA GAC AAC CTG CAC GCC GAG GGA GCG CGT CGT CCT GAG GAT CAG
Ala Thr Arg Asp Asn Leu His Ala Glu Gly Ala Arg Arg Pro Glu Asp Gln 3410              3420              3430              3440              3450
ACG CCC TAC ATG ATC TTG GTG GAG GAC TCT CTG GGA GGT TTG AAG AGG CGA
Thr Pro Tyr Met Ile Leu Val Glu Asp Ser Leu Gly Gly Leu Lys Arg Arg 3460              3470              3480              3490              3500
ATG GAC TTG CTG GAA GAA TCT AAT CAG CAG CTG CTG GCA ACT CTC AAC CGT
Met Asp Leu Leu Glu Glu Ser Asn Gln Gln Leu Leu Ala Thr Leu Asn Arg 3510              3520              3530              3540              3550
CTC CGT ACA GGA CTC GCT GCC TAT GTG CAG GCT AAC CTT GTG GGC GGC CAA
Leu Arg Thr Gly Leu Ala Ala Tyr Val Gln Ala Asn Leu Val Gly Gly Gln 3560              3570              3580              3590              3600              3610
GTT AAC CCC TTT GTT TAAATA AAAATACACT CATACAGTTT ATTATGCTGT
Val Asn Pro Phe Val End 3620         3630         3640         3650         3660         3670
CAATAAAATT CTTTATTTTT CCTGTGATAA TACCGTGTCC AGCGTGCTCT GTCAATAAGG 3680         3690         3700         3710         3720         3730
GTCCTATGCA TCCTGAGAAG GGCCTCATAT ACCCATGGCA TGAATATTAA GATACATGGG
```

FIG. 1K

```
      3740        3750        3760        3770        3780        3790
CATAAGGCCC  TCAGAAGGGT  TGAGGTAGAG  CCACTGCAGA  CTTTCGTGGG  GAGGTAAGGT 3800        3810        3820        3830        3840        3850
GTTGTAAATA  ATCCAGTCAT  ACTGACTGTG  CTGGGCGTGG  AAGGAAAAGA  TGTCTTTTAG 3860        3870        3880        3890        3900        3910
AAGAAGGGTG  ATTGGCAAAG  GGAGGCTCTT  AGTGTAGGTA  TTGATAAATC  TGTTCAGTTG 3920        3930        3940        3950        3960        3970
GGAGGGATGC  ATTCGGGGGC  TAATAAGGTG  GAGTTTAGCC  TGAATCTTAA  GGTTGGCAAT 3980        3990        4000        4010        4020        4030
GTTGCCCCCT  AGGTCTTTGC  GAGGATTCAT  GTTGTGCAGT  ACCACAAAAA  CAGAGTAGCC 4040        4050        4060
TGTGCATTTG  GGGAATTTAT  CATGAAGCT  T
```

FIG. 1L

```
                    ACTIVATION REGION 140                                  153
Ad5   GluGluPheValLeuAspTyr    ValGlu    HisProGlyHisGly
          |---|                 ||                 |---|
BAV3  GluGluValThrSerHisPhePheLeuAspCysProGluAspProSerArgGlu
          155                                          172

METAL BINDING REGION 154                                                      174
Ad5   CysArgSerCysHisTyrHisArgArgAsnThrGlyAspProAspIleMetCysSerLeuCys
          |---|                                                  |---|
BAV3  CysSerSerCysGlyPheHisGlnAlaGlnSerGlyIleProGlyIleMetCysSerLeuCys
          173                                                      193

PROMOTER BINDING REGION 175                    189
Ad5   TyrMetArgThrCys    GlyMetPheValTyrSerProValSerGluProGlu
          |---|            |---|                          |---|
BAV3  TyrMetArgGlnThrTyrHisCys    IleTyrSerProValSerGluGluProGluMetEnd
          194                                                      208
```

FIG. 2A

```
                                        Rb BINDING SEQUENCE
Ad5     120                                       132
        IleAspLeuThrCysHisGluAlaGlyPheProProSer
        :   |   |    |   |   |   |           |   |   |
        ValAspLeuGluCysHisGluVal    LeuProProSer
BAV3    26                                      37
```

FIG. 2B

```
Ad5     82                                                          100
        LeuAspPheSerThrProGlyArgAlaAlaAlaAlaValAlaPheLeuSerPheIle
        |   |           |   |   |   |           |   |   |   |   |   |   |
        LeuAsp      ThrProGlyArgValValAlaAlaLeuAlaLeuLeuValPheIle
BAV3    83                                                          99
```

FIG. 3A

```
Ad5     20          26
        GlnSerSerAsnSerThrSer
        |   |   |       |   |   |
        GlnSerSerArgSerThrSer
BAV3    136                142
```

FIG. 3B

```
Ad5  150  GlnLysTyrSerIleGluGlnLeuThrThrTyrTrpLeuGlnProGlyAspAspPheGlu
          :  | |        |       :    :  |              |   |    |
BAV3  74  GluArgTyrSerPheGluAspIleLysSerTyrGluAlaLeuProGluAspAsnLeuGlu

170 GluAlaIleArgValTyrAlaLysValAlaLeuArgProAspCysLysTyrLysIleSer
             :     | |   :     |       |             |            :  :
      94  GlnLeuIleAlaMetHisAlaLysIleLysLeuLeuProGlyArgGluTyrGluLeuThr

190 LysLeuValAsnIleArgAsnCysCysTyrIleSerGlyAsnGlyAlaGluValGluIle
          :  |       |        |    |  :  |   |   |              :   :
      114 GlnProLeuAsnIleThrSerCysAlaTyrValLeuGlyAsnGlyAlaThrIleArgVal

210 AspThrGluAspArgValAlaPheArgCysSerMetIleAsnMetTrpProGlyValLeu
             |         |     |              :   :      |   |
      134 ThrGlyGluAlaSerProAlaIleArgValGlyAlaMetAlaValGlyProCysValThr

230 GlyMetAspGlyValValIleMetAsnValArgPheThr    GlyProAsnPheSerGly
          |  |     |  |        :  |     |  |                           |
      154 GlyMetThrGlyValThrPheValAsnCysArgPheGluArgGluSerThrIleArgGly

249 ThrValPheLeuAlaAsnThrAsnLeuIleLeuHisGlyValSerPheTyr    GlyPhe
             :      |  |        |  |        |  |   :  :                |
      174 SerLeuIleArgAlaSerThrHisValLeuPheHisGlyCys    TyrPheMetGlyIle

268 AsnAsnThrCysValGluAlaTrpThrAspValArgValArgGlyCysAlaPheTyrCys
                |  |  :  |
      193 MetGlyThrCysIleGluValGlyAlaGlyAlaTyrIleArgGlyCysGluPheValGly

288 CysTrpLysGlyValValCysArgProLysSerArgAla    SerIleLysLysCysLeu
          |  :     |  :     |                                  :  :     |
      213 CysTyrArgGlyIle    CysSerThrSerAsnArgAspIleLysValArgGlnCysAsn

307 PheGluArgCysThrLeuGlyIleLeuSerGluGlyAsnSerArgValArgHisAsnVal
          |  :  :     |  |  |        |        |   :           | |
      232 PheAspLysCysLeuLeuGlyIleThrCysLysGlyAspTyrArgLeuSerGlyAsnVal

327 AlaSerAspCysGlyCysPheMetLeuValLysSerValAlaValIleLysHisAsnMet
          |  :        |  |     :                 :  :     |   |
      252 CysSerGluThrPheCysPheAlaHisLeuGluGlyGluGlyLeuValLysAsnAsnThr
```

FIG. 4A

```
347   Val   CysGlyAsn      CysGluAspArgAlaSerGlnMetLeuThrCysSerAsp
      |     |   |    |      :       |  :  |    |    :   |
272   ValLysSerProSerArgTrpThrSerGluSerGlyPheSerMetIleThrCysAlaAsp

364   GlyAsnCysHisLeuLeuLysThrIleHisVal   AlaSerHisSerArgLysAlaTrp
      |     |   |   :  :   |   :          :          |   :       |
292   GlyArgValThrProLeuGlySerLeuHisIleValGlyAsnArgCysArgArg   Trp

383   ProValPheGluHisAsnIleLeuHisArgCysSerLeuHisLeuGlyAsnArgArgGly
      |        |   :                    |   -  |   |   |        |
311   ProThrMetGlnGlyAsnValPheIleMetSerLysLeuTyrLeuGlyAsnArgIleGly

403      ValPheLeuProTyrGlnCysAsnLeuSerHisThrLysIleLeuLeuGluProGlu
         |     |   |      |   |                 :   :   |   |   |
331   ThrValAlaLeuPro   GlnCysAlaPheTyrLysSerSerIleCysLeuGluGluArg

422   SerMetSerLysValAsnLeuAsnGlyValPheAspMetThrMetLysIleTrpLysVal
      :        |   :        |       |   :              :   :   | |
350   AlaThrAsnLysLeuValLeuAlaCysAlaPheGluAsnAsnValLeuValTyrLysVal

442   LeuArgTyrAspGluThrArgThrArgCysArgProCysGluCysGlyGlyLysHisIle
      |  |        :           |      :       |   |   |           |
370   LeuArgArgGluSerProSerThr   ValLysMetCysValCysGlyThrSerHisTyr

462   ArgAsnGlnProValMetLeuAspVal   ThrGluGluLeuArgProAspHisLeuVal
         |   :  |      :     :  :              |           :     :
389      AlaLysProLeuThrLeuAlaIleIleSerSerAspIleArgAlaAsnArgTyrMet

481   LeuAlaCysHisArgAlaGluPheGlySerSerAspGluAspThrAspEnd
         :     |  |   ·     :     |   |   |   |
408      TyrThrValAspSerThrGluPhe   ThrSerAspGluAspEnd
```

FIG. 4B

| Ad5 | 1 | MetSerThrAsnSerPheAspGlySerIleValSerTyrLeuThrThrArgMetPro |
| BAV3 | 1 | MetAla Glu GluGlyArgIleTyrValProTyrValThrAlaArgLeuPro |
| | 21 | ProTrpAlaGlyValArgGlnAsnValMetGlySerSerIleAspGlyArgProValLeu |
| | 18 | LysTrpSerGlySerValGlnAspLysThrGlySerAsnMetLeuGlyGlyValValLeu |
| | 41 | ProAlaAsnSerThrThrLeuThrThrTyrGluThrValSerGlyThrProLeuGluThrAla |
| | 38 | ProProAsnSerGlnAlaHisArgThrGluThrVal GlyThrGlu AlaThr |
| | 61 | AlaSerAlaAlaAlaSerAlaAlaAlaAlaThrAlaArgGlyIleValThrAspPheAla |
| | 55 | ArgAspAsnLeuHisAlaGluGlyAlaArg ArgProGluAspGlnThr Pro |
| | 81 | PheLeuSerProLeuAlaSerSerAlaAlaSerArgSerAlaArgAspAspLysLeu |
| | 72 | TyrMetIle LeuValGluAspSerLeuGlyLeuLysArgMetAspLeuLeu |
| | 101 | ThrAlaLeuLeuAlaGlnLeu AspSerLeuThrArgGluLeuAsnValValSerGln |
| | 91 | GluGluSerAsnGlnGlnLeuLeuAlaThrLeuAsnArg LeuArgThr Gly |
| | 120 | GlnLeuLeuAspLeuArgGlnGlnValSerAlaLeuLysAlaSerSerProProAsnAla |
| | 108 | LeuAlaAlaTyr ValGln AlaAsnLeuValGlyGlyGlnValAsnProPhe |
| | 140 | ValEnd |
| | 125 | ValEnd |

FIG. 5

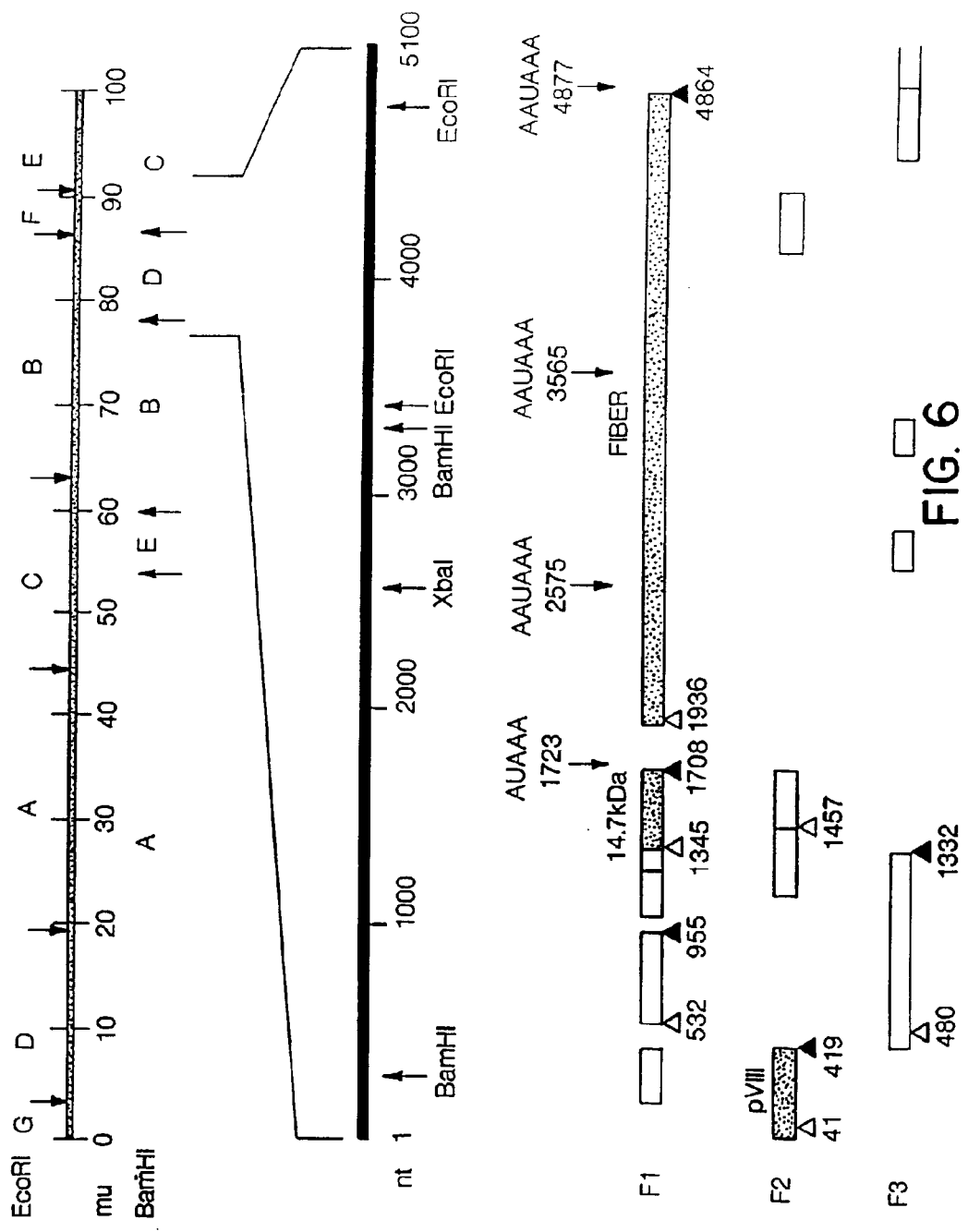

```
                        10                  20                  30                  40                  50
      C CTC ATC AAA CAA CCC GTG GGC ACC ACC CAC GTG GAA ATG CCT CGC AAC
ORF 1   Leu Ile Lys Gln Pro Val Val Gly Thr Thr His Val Glu Met Pro Arg Asn 60                  70                  80                  90                 100
      GAA GTC CTA GAA CAA CAT CTG ACC TCA CAT GGC GCT CAA ATC GCG GGC GGA
      Glu Val Leu Glu Gln His Leu Thr Ser His Gly Ala Gln Ile Ala Gly Gly 110                 120                 130                 140                 150
      GGC GCT GCG GGC GAT TAC TTT AAA AGC CCC ACT TCA GCT CGA ACC CTT ATC
      Gly Ala Ala Gly Asp Tyr Phe Lys Ser Pro Thr Ser Ala Arg Thr Leu Ile 160                 170                 180                 190                 200
      CCG CTC ACC GCC TCC TGC TTA AGA CCA GAT GGA GTC TTT CAA CTA GGA GGA
      Pro Leu Thr Ala Ser Cys Leu Arg Pro Asp Gly Val Phe Gln Leu Gly Gly 210                 220                 230                 240                 250
      GGC TCG CGT TCA TCT TTC AAC CCC CTG CAA ACA GAT TTT GCC TTC CAC GCC
      Gly Ser Arg Ser Ser Phe Asn Pro Leu Gln Thr Asp Phe Ala Phe His Ala 260                 270                 280                 290                 300
      CTG CCC TCC AGA CCG CGC CAC GGG GGC ATA GGA TCC AGG CAG TTT GTA GAG
      Leu Pro Ser Arg Pro Arg His Gly Gly Ile Gly Ser Arg Gln Phe Val Glu
```

FIG. 7A

```
310                    320                   330                    340                   350
GAA TTT GTG CCC GCC GTC TAC CTC AAC CCC TAC TCG GGA CCG CCG GAC TCT
Glu Phe Val Pro Ala Val Tyr Leu Asn Pro Tyr Ser Gly Pro Pro Asp Ser 360                    370                   380                    390                   400
TAT CCG GAC CAG TTT ATA CGC CAC TAC AAC GTG TAC AGC AAC TCT GTG AGC
Tyr Pro Asp Gln Phe Ile Arg His Tyr Asn Val Tyr Ser Asn Ser Val Ser
                                                               ORF 2 Ala 410                    420                   430                    440                   450                    460
GGT TAT AGC T GAG ATT GTA AGA CTC TCC TAT CTG TCT CTG TGC TGC TTT TCC
Gly Tyr Ser    Glu Ile Val Arg Leu Ser Tyr Leu Ser Leu Cys Cys Phe Ser
Val Ile Ala 470                    480                   490                    500                   510
GCT TCA AGC CCC ACA AGC ATG AAG GGG TTT CTG CTC ATC TTC AGC CTG CTT
Ala Ser Ser Pro Thr Ser Met Lys Gly Phe Leu Leu Ile Phe Ser Leu Leu 520                    530                   540                    550                   560
GTG CAT TGT CCC CTA ATT CAT GTT GGG ACC ATT AGC TTC TAT GCT GCA AGG
           ORF 3  Phe Met Leu Gly Pro Leu Ala Ser Met Leu Gln Gly
Val His Cys Pro Leu Ile His Val Gly Thr Ile Ser Phe Tyr Ala Ala Arg
```

FIG. 7B

```
570                         580                         590                         600                             610
CCC GGG TCT GAG CCT AAC GCG ACT GTT TGT GAC TAT GTT TGT GAC TAT GGA AGC GAG TCA
Pro Gly Leu Ser Leu Thr Arg Leu Met Phe Val Thr Met Glu Ala Ser Gln
Pro Gly Ser Glu Pro Asn Ala Thr Tyr Val Cys Asp Tyr Gly Ser Glu Ser 620                         630                         640                         650                             660
GAT TAC AAC CCC ACC ACG GTT CTG TGG GGT TTG GCT CGA GAG ACC GAT GGC TCC
Ile Thr Thr Pro Pro Arg Phe Cys Gly Trp Leu Gly Glu Arg Pro Met Ala Pro
Asp Tyr Asn Pro Thr Thr Val Leu Trp Leu Ala Arg Glu Thr Asp Gly Ser 670                         680                         690                         700                             710
TGG ATC TCT GTT CTT TTC CGT CAC AAC GGC TCC TCA ACT GCA GCC CCC GGG
Gly Ser Leu Phe Phe Ser Val Thr Thr Ala Pro Gln Leu Gln Pro Pro Gly
Trp Ile Ser Val Leu Phe Arg His Asn Gly Ser Ser Thr Ala Ala Pro Gly 720                         730                         740                         750                             760
GTC GTC GCG CAC TTT ACT GAC CAC AAC AGC AGC ATT GTG GTG CCC CAG TAT
Ser Ser Arg Thr Leu Leu Thr Thr Thr Ala Ala Leu Trp Cys Pro Ser Ile
Val Val Ala His Phe Thr Asp His Asn Ser Ser Ile Val Val Pro Gln Tyr 770                         780                         790                         800                             810
TAC CTC CTC AAC AAC TCA CTC TCT AAG CTC TGC TGC TCA TAC CGG CAC AAC
Thr Ser Ser Thr His Ser Leu Ser Ser Ala Ala His Thr Gly Thr Thr
Tyr Leu Leu Asn Asn Ser Leu Ser Lys Leu Cys Cys Ser Tyr Arg His Asn
```

FIG. 7C

820
GAG CGT TCT CAG TTT ACC TGC AAA CAA GCT GAC GTC CCT ACC TGT CAC GAG
Glu Arg Ser Gln Phe Thr Cys Lys Gln Ala Asp Val Pro Thr Cys His Glu
                830            840            850            860
Ser Val Leu Ser Leu Pro Ala Asn Lys Leu Thr Ser Leu Pro Val Thr Ser

870
CCC GGC AAG CTC ACC CTC CGC GTC TCC CCC GCG CTG GGA ACT GCC CAC
Pro Gly Lys Leu Thr Leu Arg Val Ser Pro Ala Leu Gly Thr Ala His
            880            890            900            910            920
Pro Ala Ser Arg Ser Pro Ser Ala Ser Pro Arg Trp Glu Leu Pro Thr

930
CAA GCA GTC ACT TGG TTT TTT CAA AAT GTA CCC ATA GCT ACT GTT TAC CGA
Lys Gln Ser Leu Gly Phe Phe Lys Phe Lys Met Tyr Pro
        940            950            960            970
Gln Ala Val Thr Trp Phe Phe Gln Asn Val Pro Ile Ala Thr Val Tyr Arg

980
CCT TGG GGC AAT GTA ACT TGG TTT CCT CCC TTC ATG TGT ACC TTT AAT
Pro Trp Gly Asn Val Thr Trp Phe Pro Pro Phe Met Cys Thr Phe Asn
            990            1000            1010            1020

1030
GTC AGC CTG AAC TCC CTA CTT ATT TAC AAC TTT TCT GAC AAA ACC GGG GGG
Val Ser Leu Asn Ser Leu Leu Ile Tyr Asn Phe Ser Asp Lys Thr Gly Gly
        1040            1050            1060            1070

FIG. 7D

```
         1080            1090           1100           1110          1120
CAA TAC ACA GCT CTC ATG CAC TCC GGA CCT GCT TCC CTC TTT CAG CTC TTT
Gln Tyr Thr Ala Leu Met His Ser Gly Pro Ala Ser Leu Phe Gln Leu Phe 1130            1140           1150           1160          1170
AAG CCA ACG ACT TGT GTC ACC AAG GTG GAG GAC CCG TAT GCC AAC GAC
Lys Pro Thr Thr Cys Val Thr Lys Val Glu Asp Pro Tyr Ala Asn Asp 1180            1190           1200           1210          1220
CCG GCC TCG CCT GTG TGG CGC CTG CTT TTT GCC TTC GTC CTC TGC ACC
Pro Ala Ser Pro Val Trp Arg Leu Leu Phe Ala Phe Val Leu Cys Thr 1230            1240           1250           1260          1270
GGC TGC GCG GTG TTG TTA ACC GCC TTC GGT CCA TCG ATT CTA TCC GGT ACC
Gly Cys Ala Val Leu Leu Thr Ala Phe Gly Pro Ser Ile Leu Ser Gly Thr
                         ORF 4  Pro Pro Ser Val His Arg Phe Tyr Pro Val Pro 1280            1290           1300           1310          1320
CGA AAG CTT ATC TCA GCC CGC TTT TGG AGT GTT CCC GAG CCC TAT ACC ACC CTC
Glu Ser Leu Ser Gln Pro Ala Phe Gly Val Pro Ser Pro Ile Pro Pro Ser
Arg Lys Leu Ile Ser Ala Arg Phe Trp Ser Pro Glu Pro Tyr Thr Thr Leu
```

FIG. 7E

```
1330         1340         1350         1360         1370         1380
CAC T AAC AGT CCC CCC ATG GAG CCA GAC GGA GTT CAT GCC GAG CAG CAG TTT
    Thr Asn Ser Pro Pro Met Glu Pro Asp Gly Val His Ala Glu Gln Gln Phe
His 1390         1400         1410         1420         1430
ATC CTC AAT CAG ATT TCC TGC GCC AAC ACT GCC CTC CAG CGT CAA AGG GAG
Ile Leu Asn Gln Ile Ser Cys Ala Asn Thr Ala Leu Gln Arg Gln Arg Glu 1440         1450         1460         1470         1480
GAA CTA GCT TCC CTT GTC ATG TTG CAT GCC TGT AAG CGT GGC CTC TTT TGT
Glu Leu Ala Ser Leu Val Met Leu His Ala Cys Lys Arg Gly Leu Phe Cys
ORF 5  Leu Pro Leu Ser Cys Cys Met Pro Val Ser Val Ala Ser Phe Val 1490         1500         1510         1520         1530
CCA GTC AAA ACT TAC AAG CTC AGC CTC AAC GCC TCG GCC AGC GAG CAC AGC
Pro Val Lys Thr Tyr Lys Leu Ser Leu Asn Ala Ser Ala Ser Glu His Ser
Gln Ser Lys Leu Thr Ser Ser Ala Ser Thr Pro Arg Pro Ala Ser Thr Ala 1540         1550         1560         1570         1580
CTG CAC TTT GAA AAA AGT CCC TCC CGA TTC ACC CTG GTC AAC ACT CAC GCC
Leu His Phe Glu Lys Ser Pro Ser Arg Phe Thr Leu Val Asn Thr His Ala
Cys Thr Leu Lys Lys Val Pro Pro Asp Ser Pro Trp Ser Pro Thr Leu Thr Pro
```

FIG. 7F

```
1590                1600                1610                1620                1630
GGA GCT TCT GTG CGA GTG GCC CTA CAC CAG GGA GCT TCC GGC AGC ATC
Gly Ala Ser Val Arg Val Ala Leu His Gln Gly Ala Ser Gly Ser Ile
Glu Leu Leu Cys Glu Trp Pro Tyr Thr Thr Arg Glu Leu Pro Ala Ala Ser 1640                1650                1660                1670                1680
CGC TGT TCC TGT TCC CAC GCC GAG TGC CTC CTC CTC AAG ACC CTC
Arg Cys Ser Cys Ser His Ala Glu Cys Leu Pro Val Leu Leu Lys Thr Leu
Ala Val Pro Val Pro Thr Pro Ser Ala Ser Pro Ser Ser Ser Arg Pro Ser 1690                1700                1710                1720        1730                1740
TGT GCC TTT AAC TTT TTA GAT TAG CTGAAAGCAA ATATAAAATG GTGTGCTTAC
Cys Ala Phe Asn Phe Leu Asp
Val Pro Leu Thr Phe 1750                1760                1770                1780                1790
CGTAATTCTG TTTTGACTTG TGTGCTTGA TTT CTC CCC CTG CGC CGT AAT CCA GTG 1800                1810                1820                1830                1840
CCC CTC TTC AAA ACT CTC GTA CCC TAT GCG ATT CGC ATA GGC ATA TTT TCT 1850                1860                1870                1880                1890
AAA AGC TCT GAA GTC AAC ATC ACT CTC AAA CAC TTC TCC GTT GTA GGT TAC
```

FIG. 7G

```
1900                 1910                 1920                 1930                 1940                 1950
TTT CAT CTA CAG ATA AAG TCA TCC ACC GGT T AAC ATC ATG AAG AGA AGT GTG
        ORF 6   Ser His Pro Pro Val  Asn Ile Met Lys Arg Ser Val 1960                 1970                 1980                 1990                 2000
CCC CAG GAC TTT AAT CTT GTG TAT CCG TAC AAG GCT AAG AGG CCC AAC ATC
Pro Gln Asp Phe Asn Leu Val Tyr Pro Tyr Lys Ala Lys Arg Pro Asn Ile 2010                 2020                 2030                 2040                 2050
ATG CCG CCC TTT TTT GAC CGC AAT GGC TTT GTT GAA GTT GAA AAC CAA GAA GCC ACG
Met Pro Pro Phe Phe Asp Arg Asn Gly Phe Val Glu Asn Gln Glu Ala Thr 2060                 2070                 2080                 2090                 2100
CTA GCC ATG CTT GTG GAA AAG CCG CTC ACG TTC GAC AAG GAA GGT GCG CTG
Leu Ala Met Leu Val Glu Lys Pro Leu Thr Phe Asp Lys Glu Gly Ala Leu 2110                 2120                 2130                 2140                 2150
ACC CTG GGC GTC GGA CGC GGC ATC CGC ATT AAC CCC GCG GGG CTT CTG GAG
Thr Leu Gly Val Gly Arg Gly Ile Arg Ile Asn Pro Ala Gly Leu Leu Glu 2160                 2170                 2180                 2190                 2200
ACA AAC GAC CTC GCG TCC GCT GTC TTC CCA CCG CTG GCC TCC GAT GAG GCC
Thr Asn Asp Leu Ala Ser Ala Val Phe Pro Pro Leu Ala Ser Asp Glu Ala
```

FIG. 7H

```
     2210           2220           2230           2240           2250
GGC AAC GTC ACG CTC AAC ATG TCT GAC GGG CTA TAT ACT AAG GAC AAC AAG
Gly Asn Val Thr Leu Asn Met Ser Asp Gly Leu Tyr Thr Lys Asp Asn Lys 2260           2270           2280           2290           2300
CTA GCT GTC AAA GTA GGT CCC GGG CTG TCC GAC TCC AAT AAT GCT CTC
Leu Ala Val Lys Val Gly Pro Gly Leu Ser Leu Asp Ser Asn Asn Ala Leu 2310           2320           2330           2340           2350
CAG GTC CAC ACA GGC GAC GGG CTC ACG GTA ACC GAT GAC AAG GTG TCT CTA
Gln Val His Thr Gly Asp Gly Leu Thr Val Thr Asp Asp Lys Val Ser Leu 2360           2370           2380           2390           2400
AAT ACC CAA GCT CCC CTC TCG ACC ACC AGC GCG GGC CTC TCC CTA CTT CTG
Asn Thr Gln Ala Pro Leu Ser Thr Thr Ser Ala Gly Leu Ser Leu Leu Leu 2410           2420           2430           2440           2450           2460
GGT CCC AGC CTC CAC TTA GGT GAG GAG CGA CTA GAA CGA AAC ACC GGA
Gly Pro Ser Leu His Leu Gly Glu Glu Arg Leu Glu Arg Asn Thr Gly 2470           2480           2490           2500           2510
GCG GGC CTC CAA ATT AGC AAT AAC GCT CTG GCC GTA AAA GTA GGT TCA GGT
Ala Gly Leu Gln Ile Ser Asn Asn Ala Leu Ala Val Lys Val Gly Ser Gly
```

FIG. 7I

```
              2520                    2540                    2560
ATC ACC GTA GAT GCT CAA AAC CAG CTC GCT GCA TCC CTG GGG GAC GGT CTA
Ile Thr Val Asp Ala Gln Asn Gln Leu Ala Ala Ser Leu Gly Asp Gly Leu 2570                    2590                    2610
GAA AGC AGA GAT AAT AAA ACT GTC GTT AAG GCT GGG CCC GGA CTT ACA ATA
Glu Ser Arg Asp Asn Lys Thr Val Val Lys Ala Gly Pro Gly Leu Thr Ile 2620                    2640                    2660
ACT AAT CAA GCT CTT ACT GTT GCT ACC GGG AAC GGC CTT CAG GTC AAC CCG
Thr Asn Gln Ala Leu Thr Val Ala Thr Gly Asn Gly Leu Gln Val Asn Pro 2670                    2690                    2710
GAA GGG CAA CTG CAG CTA AAC ATT ACT GCC GGT CAG GGC CTC AAC TTT GCA
Glu Gly Gln Leu Gln Leu Asn Ile Thr Ala Gly Gln Gly Leu Asn Phe Ala 2720                    2740                    2760
AAC AAC AGC CTC GCC GTG GAG CTG CTG GGC TCG GGC CTG CAT TTT CCC CCT GGC
Asn Asn Ser Leu Ala Val Glu Leu Leu Gly Ser Gly Leu His Phe Pro Pro Gly 2770                    2790                    2810
CAA AAC CAA GTA AGC CTT TAT CCC GGA GAT GGA ATA GAC ATC CGA GAT AAT
Gln Asn Gln Val Ser Leu Tyr Pro Gly Asp Gly Ile Asp Ile Arg Asp Asn
```

FIG. 7J

```
     2820                2830                2840                2850                2860
     AGG GTG ACT GTG CCC GCT GGG CCA GGC CTG AGA ATG CTC AAC CAC CAA CTT
     Arg Val Thr Val Pro Ala Gly Pro Gly Leu Arg Met Leu Asn His Gln Leu 2870                2880                2890                2900                2910
     GCC GTA GCT TCC GGA GAC GGT TTA GAA GTC CAC AGC GAC ACC CTC CGG TTA
     Ala Val Ala Ser Gly Asp Gly Leu Glu Val His Ser Asp Thr Leu Arg Leu 2920                2930                2940                2950                2960                2970
     AAG CTC TCC CAC GGC CTG ACA TTT GAA AAT GGC GCC GTA CGA GCA AAA CTA
     Lys Leu Ser His Gly Leu Thr Phe Glu Asn Gly Ala Val Arg Ala Lys Leu 2980                2990                3000                3010                3020
     GGA CCA GGA CTT GGC ACA GAC GAC TCT GGT CGG TCC GTG GTT CGC ACA GGT
     Gly Pro Gly Leu Gly Thr Asp Asp Ser Gly Arg Ser Val Val Arg Thr Gly 3030                3040                3050                3060                3070
     CGA GGA CTT AGA GTT GCA AAC GGC CAA GTC CAG ATC TTC AGC GGA AGA GGC
     Arg Gly Leu Arg Val Ala Asn Gly Gln Val Gln Ile Phe Ser Gly Arg Gly 3080                3090                3100                3110                3120
     ACC GCC ATC GGC ACT GAT AGC AGC CTC ACT CTC AAC ATC CGG GCG CCC CTA
     Thr Ala Ile Gly Thr Asp Ser Ser Leu Thr Leu Asn Ile Arg Ala Pro Leu
```

FIG. 7K

```
      3130                3140                3150               3160                   3170
CAA TTT TCT GGA CCC GCC TTG ACT GCT AGT TTG CAA GGC AGT GGT CCG ATT
Gln Phe Ser Gly Pro Ala Leu Thr Ala Ser Leu Gln Gly Ser Gly Pro Ile 3180                3190                3200               3210                   3220
ACT TAC AAC AGC AAC AAT GGC ACT TTC GGT CTC TCT ATA GGC CCC GGA ATG
Thr Tyr Asn Ser Asn Asn Gly Thr Phe Gly Leu Ser Ile Gly Pro Gly Met 3230                3240                3250               3260                   3270
TGG GTA GAC CAA AAC AGA CTT CAG GTA AAC CCA GGC GCT GGT TTA GTC TTC
Trp Val Asp Gln Asn Arg Leu Gln Val Asn Pro Gly Ala Gly Leu Val Phe 3280                3290                3300               3310                   3320
CAA GGA AAC AAC CTT GTC CCA AAC CTT GCG GAT CCG CTG ACC GCT ATT TCC GAC
Gln Gly Asn Asn Leu Val Pro Asn Leu Ala Asp Pro Leu Thr Ala Ile Ser Asp 3330                3340                3350               3360                   3370
AGC AAA ATT AGT CTC AGT CTC GGT CCC GGC CTG ACC CAA GCT TCC AAC GCC
Ser Lys Ile Ser Leu Ser Leu Gly Pro Gly Leu Thr Gln Ala Ser Asn Ala 3380                3390                3400               3410                   3420
CTG ACT TTA AGT TTA GGA AAC GGG CTT GAA TTC TCC AAT CAA GCC GTT GCT
Leu Thr Leu Ser Leu Gly Asn Gly Leu Glu Phe Ser Asn Gln Ala Val Ala
```

FIG. 7L

```
3430       3440              3450              3460              3470              3480
ATA AAA GCG GGC CGG GGC TTA CGC TTT GAG TCT TCC TCA CAA GCT TTA GAG
Ile Lys Ala Gly Arg Gly Leu Arg Phe Glu Ser Ser Ser Gln Ala Leu Glu 3490              3500              3510              3520              3530
AGC AGC CTC ACA GTC GGA AAT GGC TTA ACG CTT ACC GAT ACT GTG ATC CGC
Ser Ser Leu Thr Val Gly Asn Gly Leu Thr Leu Thr Asp Thr Val Ile Arg 3540              3550              3560              3570              3580
CCC AAC CTA GGG GAC GGC CTA GAG GTC AGA GAC AAT AAA ATC ATT GTT AAG
Pro Asn Leu Gly Asp Gly Leu Glu Val Arg Asp Asn Lys Ile Ile Val Lys 3590              3600              3610              3620              3630
CTG GGC GCG AAT CTT CGT TTT GAA AAC GGA GCC GTA ACC GCC GGC ACC GTT
Leu Gly Ala Asn Leu Arg Phe Glu Asn Gly Ala Val Thr Ala Gly Thr Val 3640              3650              3660              3670              3680
AAC CCT TCT GCG CCC GAG GCA CCA ACT CTC ACT GCA GAA CCA CCC CTC
Asn Pro Ser Ala Pro Glu Ala Pro Thr Leu Thr Ala Glu Pro Pro Leu 3690              3700              3710              3720              3730
CGA GCC TCC AAC TCC CAT CTT CAA CTG TCC CTA TCG GAG GGC TTG GTT GTG
Arg Ala Ser Asn Ser His Leu Gln Leu Ser Leu Ser Glu Gly Leu Val Val
```

FIG. 7M

```
3740                     3750                     3760                     3770                     3780
CAT AAC AAC GCC CTT GCT CTC CAA CTG GGA GAC GGC ATG GAA GTA AAT CAG
His Asn Asn Ala Leu Ala Leu Gln Leu Gly Asp Gly Met Glu Val Asn Gln 3790                     3800                     3810                     3820                     3830
CAC GGA CTT ACT TTA AGA GTA GGC TCG GGT TTG CAA ATG CGT GAC GGC ATT
His Gly Leu Thr Leu Arg Val Gly Ser Gly Leu Gln Met Arg Asp Gly Ile 3840                     3850                     3860                     3870                     3880
TTA ACA GTT ACA CCC AGC GGC ACT CCT ATT GAG CCC AGA CTG ACT GCC CCA
Leu Thr Val Thr Pro Ser Gly Thr Pro Ile Glu Pro Arg Leu Thr Ala Pro 3890                     3900                     3910                     3920                     3930
CTG ACT CAG ACA GAG AAT GGA ATC GGG GCT CTC GGC GCC GGC TTG GAA
Leu Thr Gln Thr Glu Asn Gly Ile Gly Ala Leu Gly Ala Gly Leu Glu 3940                     3950                     3960                     3970                     3980
TTA GAC GAG AGC GCG CTC CAA GTA AAA GTT GGG CCC GGC ATG CGC CTG AAC
Leu Asp Glu Ser Ala Leu Gln Val Lys Val Gly Pro Gly Met Arg Leu Asn 4000                     4010                     4020                     4030                     4040
CCT GTA GAA AAG TAT GTA ACC CTG CTC GGT CCT GGC CTT AGT TTT GGG
Pro Val Glu Lys Tyr Val Thr Leu Leu Gly Pro Gly Leu Ser Phe Gly
```

FIG. 7N

```
                4050            4060            4070            4080            4090
CAG CCG GCC AAC AGG ACA AAT TAT GAT GTG CGC GTT TCT GTG GAG CCC CCC
Gln Pro Ala Asn Arg Thr Asn Tyr Asp Val Arg Val Ser Val Glu Pro Pro 4100            4110            4120            4130            4140
ATG GTT TTC GGA CAG CGT GGT CAG CTC ACA TTT TTA GTG GGT CAC GGA CTA
Met Val Phe Gly Gln Arg Gly Gln Leu Thr Phe Leu Val Gly His Gly Leu 4150            4160            4170            4180            4190
CAC ATT CAA AAT TCC AAA CTT CAG CTC AAT TTG GGA CAA GGC CTC AGA ACT
His Ile Gln Asn Ser Lys Leu Gln Leu Asn Leu Gly Gln Gly Leu Arg Thr 4200            4210            4220            4230            4240
GAC CCC GTC ACC AAC CAG CTG GAA GTG CCC CTC GGT CAA GGT TTG GAA ATT
Asp Pro Val Thr Asn Gln Leu Glu Val Pro Leu Gly Gln Gly Leu Glu Ile 4250            4260            4270            4280            4290
GCA GAC GAA TCC CAG GTT AGG GTT AAA TTG GGC GAT GGC CTG CAG TTT GAT
Ala Asp Glu Ser Gln Val Arg Val Lys Leu Gly Asp Gly Leu Gln Phe Asp 4300            4310            4320            4330            4340
TCA CAA GCT CGC ATC ACT ACC GCT CCT AAC ATG GTC ACT GAA ACT CTG TGG
Ser Gln Ala Arg Ile Thr Thr Ala Pro Asn Met Val Thr Glu Thr Leu Trp
```

FIG. 70

```
4350                              4360                              4370                              4380                              4390
ACC GGA ACA GGC AGT AAT GCT AAT GTT ACA TGG CGG GGC TAC ACT GCC CCC
Thr Gly Thr Gly Ser Asn Ala Asn Val Thr Trp Arg Gly Tyr Thr Ala Pro 4400                              4410                              4420                              4430                              4440
GGC AGC AAA CTC TTT TTG AGT CTC ACT CGG TTC AGC ACT GGT CTA GTT TTA
Gly Ser Lys Leu Phe Leu Ser Leu Thr Arg Phe Ser Thr Gly Leu Val Leu 4450                              4460                              4470                              4480                              4490                              4500
GGA AAC ATG ACT ATT GAC AGC AGC AAT GCA TCC TTT GGG CAA TAC ATT AAC GCG
Gly Asn Met Thr Ile Asp Ser Ser Asn Ala Ser Phe Gly Gln Tyr Ile Asn Ala 4510                              4520                              4530                              4540                              4550
GGA CAC GAA CAG ATC GAA TGC TTT ATA TTG TTG GAC AAT CAG GGT AAC CTA
Gly His Glu Gln Ile Glu Cys Phe Ile Leu Leu Asp Asn Gln Gly Asn Leu 4560                              4570                              4580                              4590                              4600
AAA GAA GGA TCT AAC TTG CAA GGC ACT TGG GAA GTG AAG AAC AAC CCC TCT
Lys Glu Gly Ser Asn Leu Gln Gly Thr Trp Glu Val Lys Asn Asn Pro Ser 4610                              4620                              4630                              4640                              4650
GCT TCC AAA GCT GCT TTT TTG CCT TCC ACC GCC CTA TAC CCC ATC CTC AAC
Ala Ser Lys Ala Ala Phe Leu Pro Ser Thr Ala Leu Tyr Pro Ile Leu Asn
```

FIG. 7P

```
4660                     4670             4680                    4690                    4700
GAA AGC CGA GGG AGT CTT CCT GGA AAA AAT CTT GTG GGC ATG CAA GCC ATA
Glu Ser Arg Gly Ser Leu Pro Gly Lys Asn Leu Val Gly Met Gln Ala Ile 4710                    4720                    4730                    4740             4750
CTG GGA GGC GGG GGC ACT TGC ACT GTG ATA GCC ACC CTC AAT GGC AGA CGC
Leu Gly Gly Gly Gly Thr Cys Thr Val Ile Ala Thr Leu Asn Gly Arg Arg 4760                    4770                    4780                    4790             4800
AGC AAC AAC TAT CCC GCG GGC TCC ATA ATT TTC GTG TGG CAA GAA TTC
Ser Asn Asn Tyr Pro Ala Gly Ser Ile Ile Phe Val Trp Gln Glu Phe 4810                    4820                    4830                    4840             4850
AAC ACC ATA GCC CGC CAA CCT CTG AAC CAC TCT ACA CTT ACT TTT TCT TAC
Asn Thr Ile Ala Arg Gln Pro Leu Asn His Ser Thr Leu Thr Phe Ser Tyr 4860                    4870                    4880                    4890             4900
TGG ACT TA AAT AAG TTG GAA ATA AAG AGT TAA ACT GAA TGT TTA AGT GCA
Trp Thr 4910                    4920                    4930                    4940             4950
ACA GAC TTT TAT TGG TTT TGG CTC ACA ACA AAT TAC AAC AGC ATA GAC AAG 4960                    4970                    4980                    4990             5000
TCA TAC CGG TCA AAC AAC ACA GGC TCT CGA AAA CGG GCT AAC CGC TCC AAG
```

FIG. 7Q

```
5010            5020            5030            5040            5050            5060
AAT CTG TCA CGC AGA CGA GCA AGT CCT AAA TGT TTT TTC ACT CTC TTC GGG
       5070            5080            5090            5100
GCC AAG TTC AGC ATG TAT CGG ATT TTC TGC TTA CAC CTT T
```

FIG. 7R

| | | |
|---|---|---|
| Ad2 | MSKEIPTPYMWSYQPQMGLAAGAAQDYSTRINYMSAGPHMISRVNGIRAH | 50 |
| BAV3 | LIKQPVVGTTHV-------------------EMPRNEVLEQH | 23 |
| | :. : . :: .:: : | |
| Ad2 | RNRILLEQAAITTTPRNNLNPRSWPAALVYQESPAPTTVVLPRDAQAEVQ | 100 |
| BAV3 | LTSHGAQIAGGG-----AAGDYFKSPTSARTLIPLTASCL------RPDG | 62 |
| | .: :::.::: . : : : . :::: | |
| Ad2 | MTNSGAQLAGGFRHRVRSPGQGITHLKIRGRGIQLNDESVSSSLGLRPDG | 150 |
| BAV3 | VFQLGGGSRSSFNPLQTDFAFHALPSRPRHGGIGSRQFVEEFVPAVYLNP | 112 |
| | :: .:: :::: :. :. . : :: ::::. ::.::::.: :: | |
| Ad2 | TFQIGGAGRSSFTPRQAILTLQTSSSEPRSGGIGTLQFIEEFVPSVYFNP | 200 |
| BAV3 | YSGPPDSYPDQFIRHYNVYSNSVSGYS   139 | |
| | .:::: :::::::  .   : :: | |
| Ad2 | FSGPPGHYPDQFIPNFDAVKDSADGYD   227 | |

FIG. 8A

| | | |
|---|---|---|
| BAV3 | M------EPDGVHAEQQFILNQISCANTALQRQREELASLVMLHACKRGL | 77 |
| | : : ::. .:: . : .. :: :: .: :: ::::. | |
| Ad5 | MTDTLDLEMDGIITEQRLL--ERRRAAAEQQRMNQELQDMVNLHQCKRGI | 48 |
| BAV3 | FCPVKTYKLSLNASASEHSLHFEKSPSRFTLVNTHAGASVRVALHHQGAS | 127 |
| | :: :: :.. . .. :: . :: ... . | |
| Ad5 | FCLVKQAKVTYDSNTTGHRLSYKLPTKRQKLVVMVGEKPITITQHSVETE | 98 |
| BAV3 | GSIRCSCSHAECLPVLLKTLCAFNFLD   154 | |
| | : : : : : :.:::: : | |
| Ad5 | GCIHSPCQGPEDLCTLIKTLCGLKDLIPFN   128 | |

FIG. 8B

```
BAV3  - MKRSVPQD--FNLVYPYKAKR-----PNIMPPFFDRNGFVENQEATLAML   -43
        ::: .  :: :::: .      :  .::: ::: :           :..
Ad2   - MKRARPSEDTFNPVYPYDTETGPPTVPFLTPPFVSPNGFQESPPGVLSLR   -50

BAV3  - VEKPLTFDKE-GALTLGVGRGIRINPAGLLETNDLASAVFPPLASDEAGN   -92
        : :: :    : :.: .: :.. ::  :.. ...
Ad2   - VSEPL--DTSHGMLALKMGSGLTLDKAGNLTSQNVTTV------------   -86

BAV3  - VTLNMSDGLYTKDNKLAVKVGPGLSLDSNNALQVHTGDGLTVTDDKVSLN   -142
          .    ...   :... . :: :  :  : :  .:..
Ad2   - -------TQPLKKTKSNISLDTSAPLTI-TSGALTVATTAPLIVTSGALSVQ -130

BAV3  - TQAPLSTTSAGLSLLLGPSLHLGEEERLTVNTGAGLQISNNALAVKVGSG   -192
        .::::.     . .:.. :         ..:  ::..    .
Ad2   - SQAPLT--------------VQDSKLSIATKGPITVSDGKLALQTSAP    -164

BAV3  - ITVDAQNQLAASLGDGLESRDNKTVVKAGPGLTITNQALTVATGNGLQVN   -242
         ..       :..        :: :::    .  . ::
Ad2   - LSGSDSDTLTVT--------------------ASPPLTTATGS-LGIN   -191

BAV3  - PEGQLQLNITAGQGLNFANNSLAVELGSGLHFPPGQNQVSLYPGDGIDIR   -292
         :  . .:          :   ...     :
Ad2   - MEDPIYVN---------NGKIGIKISGPLQVAQ----------------   -215

BAV3  - DNRVTVPAGPGLRMLNHQLAVASGDGLEVHSDTLRLKLSHGLTFENGAVR   -342
                                   ::::  .     :: :.. ..:
Ad2   - --------------------------NSDTLTVVTGPGVTVEQNSLR    -236
```

FIG. 8C-1

| | | |
|---|---|---|
| BAV3 | - AKLGPGLGTDDSGRSVVRTGRGLRVANGQVQIFSGRGTAIGTDSSLTLNI | -392 |
| Ad2 | - TKVAGAIGYDSSNNMEIKTGGGMRINNNL--LILDVDYPFDAQTKLRLKL | -284 |
| BAV3 | - RAPLQFSGPALTASLQGSGPITYNSNNGTFGLSIGPGMWVDQNRLQVNPG | -442 |
| Ad2 | - ---------------GQGPLYINASHN----------------LDINYN | -302 |
| BAV3 | - AGLVFQGNNLVPNLADPLAISDSKISLSLGPGLTQASNALTLSLGNGLEF | -492 |
| Ad2 | - RGLYL-------------FNASNNTKKLEVSIKKSS---------GLNF | -329 |
| BAV3 | - SNQAVAIKAGRGLRFESSSQALESSLTVGNGLTLTDTVIRPNLGDGLEVR | -542 |
| Ad2 | - DNTAIAINAGKGLEFDTNT------------------------------ | -348 |
| BAV3 | - DNKIIVKLGANLRFENGAVTAGTVNPSAPEAPPTLTAEPPLRASNSHLQL | -592 |
| Ad2 | - ------------------------------------------------ | -348 |
| BAV3 | - SLSEGLVVHNNALALQLGDGMEVNQHGLTLRVGSGLQMRDGILTVTPSGT | -642 |
| Ad2 | - ------------------SESPDIN--PIKTKIGSGID------YNENGA | -372 |
| BAV3 | - PIEPRLTAPLTQTENGIGLALGAGLELDESALQVKVGPGMRLNPVEKYVT | -692 |
| Ad2 | - MIT--------------KLGAGLSFDNSG------------------- | -387 |

FIG. 8C-2

| | | |
|---|---|---|
| BAV3 | - LLLGPGLSFGQPANRTNYDVRVSVEPPMVFGQRGQLTFLVGHGLHIQNSK | -742 |
| Ad2 | - -----AITIG-----NKNDDKLTLWTTPDPSP--------------NCR | -412 |
| BAV3 | - LQLNLGQGLRTDPVTNQLEVPLGQGLEIADESQVRVKLGDGLQFDSQARI | -792 |
| Ad2 | - IHSD---------------------NDCKFTLVLT---KCGSQVLA | -434 |
| BAV3 | - TTAPNMVTETLWTGTGSNANVTWRGYTAPGSKLFLSLTRFSTGLVLGNMT | -842 |
| Ad2 | - TVAALAVSGDLSSMTGTVASVS---------IFLRFDQ--NGVLMENSS | -472 |
| BAV3 | - IDSNASFGQYINAGHEQIECFILLDNQGNLKEGSNLQGTWEVKNNPSASK | -892 |
| Ad2 | - LKKHY--------------------WNFRNGNS------TNANPYTNA | -494 |
| BAV3 | - AAFLPSTALYPILNESRGSLPGKNLVGMQAILGGGGTCTVIA-TLNGRRS | -941 |
| Ad2 | - VGFMPNLLAYP---KTQSQTAKNNIVSQVYLHGDKTKPMILTITLNGTSE | -541 |
| BAV3 | - NNYPAGQSII---FVWQ-EFNTIARQPLNHSTLTFSYWT | -976 |
| Ad2 | - STETSEVSTYSMSFTWSWESGKYTTETFATNSYTFSYIAQE | -582 |

FIG. 8C-3

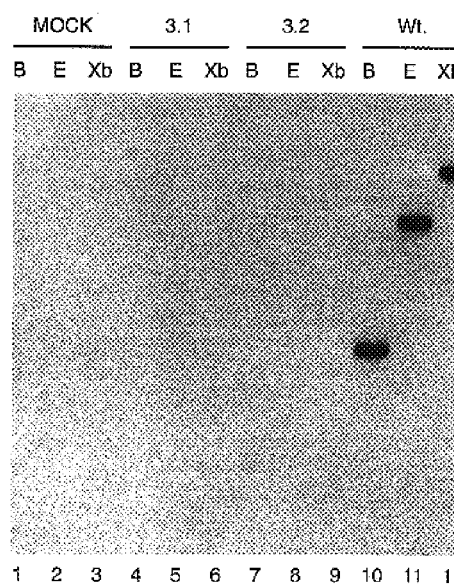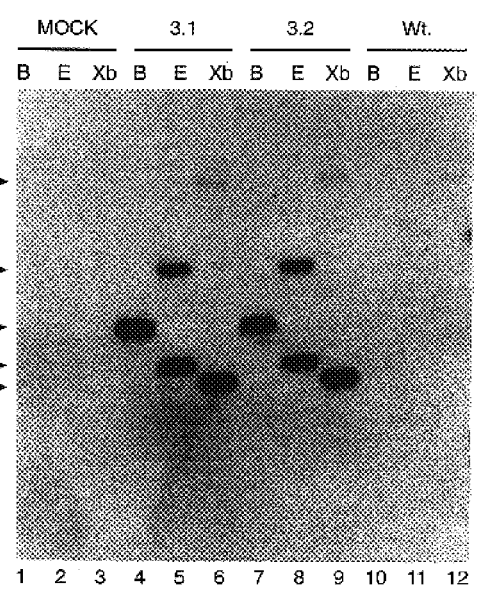
FIG. 11A  FIG. 11B

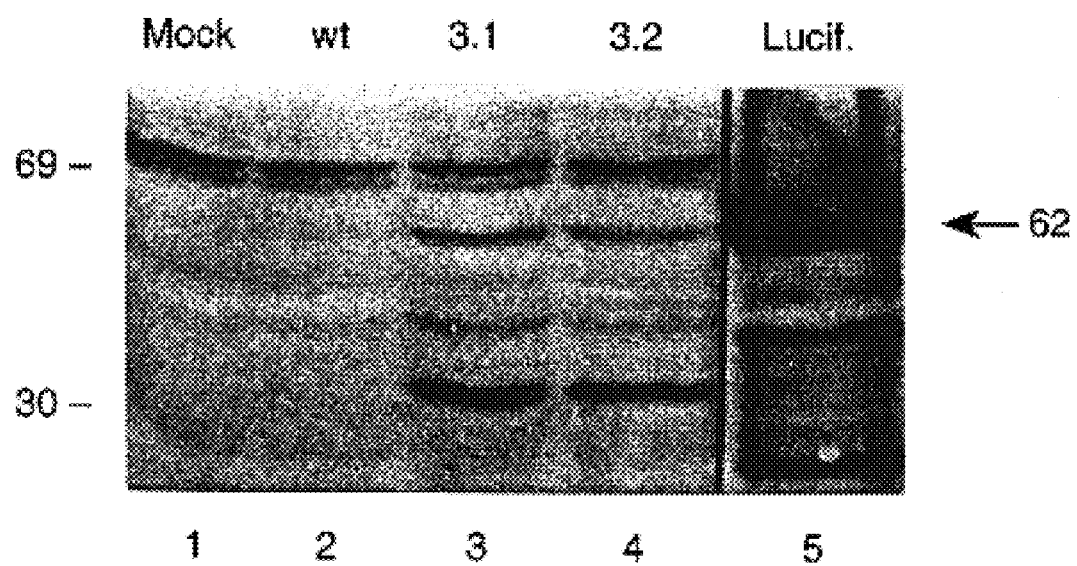
FIG._16

RECOMBINANT PROTEIN PRODUCTION IN BOVINE ADENOVIRUS EXPRESSION VECTOR SYSTEM

CROSS-REFERENCE TO RELATED APPLICATIONS

This is a continuation of U.S. patent application Ser. No. 09/435,242, filed Nov. 5, 1999 now U.S. Pat. No. 6,379,944; which is a continuation of U.S. patent application Ser. No. 08/815,927, filed Mar. 13, 1997, now U.S. Pat. No. 6,086,890; which is a continuation of U.S. patent application Ser. No. 08/164,292, filed Dec. 9, 1993, now U.S. Pat. No. 5,820,868, all of which are incorporated by reference herein in their entirety.

TECHNICAL FIELD

The present invention relates novel bovine adenovirus (BAV) expression vector systems in which one or both of the early region 1 (E1) and the early region 3 (E3) gene deletions are replaced by a foreign gene and novel recombinant mammalian cell lines stably transformed with BAV E1 sequences, and therefore, expresses E1 gene products, to allow a bovine adenovirus with an E1 gene deletion replaced by a foreign gene to replicate therein. These materials are used in production of recombinant BAV expressing heterologous (antigenic) polypeptides or fragments for the purpose of live recombinant virus or subunit vaccines or for other therapies.

BACKGROUND OF THE INVENTION

The adenoviruses cause enteric or respiratory infection in humans as well as in domestic and laboratory animals.

The bovine adenoviruses (BAVs) comprise at least nine serotypes divided into two subgroups. These subgroups have been characterized based on enzyme-linked immunoassays (ELISA), serologic studies with immunofluorescence assays, virus-neutralization tests, immunoelectron microscopy, by their host specificity and clinical syndromes. Subgroup 1 viruses include BAV 1, 2, 3 and 9 and grow relatively well in established bovine cells compared to subgroup 2 which includes BAV 4, 5, 6, 7 and 8.

BAV3 was first isolated in 1965 and is the best characterized of the BAV genotypes and contains a genome of approximately 35 kb (Kurokawa et al (1978) *J. Virol.* 28:212–218). The locations of hexon (Hu et al (1984) *J. Viol.* 49:604–608) and proteinase (Cai et al., (1990) *Nuc. Acids Res.*, 18:5568), genes in the BAV3 genome have been identified and sequenced. However, the location and sequences of other genes such as early region 1 (E1) and 3 (E3) in the BAV genome have not been reported.

In the human adenovirus (HAd) genome there are two important regions: E1 and E3 in which foreign genes can be inserted to generate recombinant adenoviruses (Berkner and Sharp (1984) *Nuc. Acid Res.*, 12:1925–1941 and Haj-Ahmad and Graham (1986) *J. Virol.*, 57:267–274). E1 proteins are essential for virus replication in tissue culture, however, conditional-helper adenovirus recombinants containing foreign DNA in the E1 region, can be generated in a cell line which constitutively expresses E1 (Graham et al., (1977) *J. Gen. Virol.*, 36:59–72). In contrast, E3 gene products of HAd 2 and HAd 5 are not required for in vitro or in vivo infectious virion production, but have an important role in host immune responses to virus infection (Andersson et al (1985) *Cell* 43:215–222; Burgert et al (1987) *EMBO J.* 6:2019–2026; Carlin et al (1989) *Cell* 57:135–144; Ginsberg et al (1989) *PNAS USA* 86:3823–3827; Gooding et al (1988) *Cell* 53:341–346; Tollefson et al (1991) *J. Virol.* 65:3095–3105; Wold and Gooding (1989) *Mol. Biol. Med.* 6:433–452 and Wold and Gooding (1991) *Virology* 184:1–8). The E3-19kiloDalton (kDa) glycoprotein (gp19) of human adenovirus type 2 (HAd2) binds to the heavy chain of a number of class 1 major histocompatibility complex (MHC) antigens in the endoplasmic reticulum thus inhibiting their transport to the plasma membrane (Andersson et al. (1985) *Cell* 43:215–222; Burgert and Kvist, (1985) *Cell* 41:987–997; Burgert and Kvist, (1987) *EMBO J.* 6:2019–2026). The E3-14.7 kDa protein of HAd2 or HAd5 prevents lysis of virus-infected mouse cells by tumor necrosis factor (TNF) (Gooding et al. (1988) *Cell* 53:341–346). In addition, the E3-10.4 kDa and E3-14.5 kDa proteins form a complex to induce endosomal-mediated internalization and degradation of the epidermal growth factor receptor (EGF-R) in virus-infected cells (Carlin et al. *Cell* 57:135–144; Tollefson et al. (1991) *J. Virol.* 65:3095–3105). The helper-independent recombinant adenoviruses having foreign genes in the E3 region replicate and express very well in every permissive cell line (Chanda et al (1990) *Virology* 175:535–547; Dewar et al (1989) *J. Virol.* 63:129–136; Johnson et al (1988) *Virology* 164:1–14; Lubeck et al (1989) *PNAS, USA* 86:6763–6767; McDermott et al (1989) *Virology* 169:244–247; Mittal et al (1993) *Virus Res.* 28:67–90; Morin et al (1987) *PNAS, USA* 84:4626–4630; Prevec et al (1990) *J. Inf. Dis.* 161:27–30; Prevec et al (1989) *J. Gen. Virol.* 70:429–434; Schneider et al (1989) *J. Gen. Virol.* 70:417–427 and Yuasa et al (1991) *J. Gen. Virol.* 72:1927–1934). Based on the above studies and the suggestion that adenoviruses can package approximately 105% of the wild-type (wt) adenovirus genome (Bett et al (1993) *J. Virol.* 67:5911–5921 and Ghosh-Choudhury et al (1987) *EMBO. J.* 6:1733–1739), an insertion of up to 1.8 kb foreign DNA can be packaged into adenovirus particles for use as an expression vector for foreign proteins without any compensating deletion.

It is assumed that an indigenous adenovirus vector would be better suited for use as a live recombinant virus vaccine in different animal species compared to an adenovirus of human origin. Non-human adenovirus-based expression vectors have not been reported so far. If like HAds E3, the E3 regions in other adenoviruses are not essential for virus replication in cultured cells, adenovirus recombinants containing foreign gene inserts in the E3 region could be generated.

BAV3 is a common pathogen of cattle usually resulting in subclinical infection though occasionally associated with a more serious respiratory tract infection (Darbyshire et al., 1966 *Res. Vet Sci* 7:81–93; Mattson et al., 1988 *J. Vet Res* 49:67–69). BAV3 can produce tumors when injected into hamsters (Darbyshire, 1966 *Nature* 211:102) and viral DNA can efficiently effect morphological transformation of mouse, hamster or rat cells in culture (Tsukamoto and Sugino, 1972 *J. Virol.* 9:465–473; Motoi et al., 1972 *Gann* 63:415–418; M. Hitt, personal communication). Cross hybridization was observed between BAV3 and human adenovirus type 2 (HAd2) (Hu et al., 1984 *J. Virol.* 49:604–608) in most regions of the genome including some regions near but not at the left end of the genome.

The E1A gene products of the group C human adenoviruses have been very extensively studied and shown to mediate transactivation of both viral and cellular genes (Berk et al., 1979 *Cell* 17:935–944; Jones and Shenk, 1979 *Cell* 16:683–689; Nevins, 1981 *Cell* 26:213–220; Nevins, 1982 *Cell* 29:913–919; reviewed in Berk, 1986 *Ann. Res.*

*Genet* 20:45–79), to effect transformation of cells in culture (reviewed in Graham, F. L. (1984) "Transformation by and oncogenicity of human adenoviruses. In:The Adenoviruses." H. S. Ginsberg, Editor. Plenum Press, New York; Branton et al., 1985 *Biochim. Biophys. Acta* 780:67–94) and induce cell DNA synthesis and mitosis (Zerler et al., 1987 *Mol. Cell Biol.* 7:821–929; Bellet et al., 1989 *J. Virol.* 63:303–310; Howe et al., 1990 *PNAS, USA* 87:5883–5887; Howe and Bayley, 1992 *Virology* 186:15–24). The E1A transcription unit comprises two coding sequences separated by an intron region which is deleted from all processed E1A transcripts. In the two largest mRNA species produced from the E1A transcription unit, the first coding regions is further subdivided into exon 1, a sequence found in both the 12 s and 13 s mRNA species, and the unique region, which is found only in the 13 s mRNA species. By comparisons between E1A proteins of human and simian adenoviruses three regions of somewhat conserved protein sequence (CR) have been defined (Kimelman et al., 1985 *J. Virol.* 53:399–409). CR1 and CR2 are encoded in exon 1, while CR3 is encoded in the unique sequence and a small portion of exon 2. Binding sites for a number of cellular proteins including the retinoblastoma protein Rb, cyclin A and an associated protein kinase p33$^{cdk2}$, and other, as yet unassigned, proteins have been defined in exon 1 encoded regions of E1A proteins (Yee and Branton, 1985 *Virology* 147:142–153; Harlow et al., 1986 *Mol. Cell Biol.* 6:1579–1589; Barbeau et al., 1992 *Biochem. Cell Biol.* 70:1123–1134). Interaction of E1A with these cellular proteins has been implicated as the mechanism through which E1A participates in immortalization and oncogenic transformation (Egan et al, 1989 *Oncogene* 4:383–388; Whyte et al., 1988 *Nature* 334:124–129; Whyte et al, 1988 *J. Virol.* 62:257–265). While E1A alone may transform or immortalize cells in culture, the coexpression of both E1A and either the E1B-19 k protein or the E1B-55 k protein separately or together is usually required for high frequency transformation of rodent cells in culture (reviewed in Graham, 1984 supra; Branton et al., 1985 supra; McLorie et al., 1991 *J. Gen Virol.* 72:1467–1471).

Transactivation of other viral early genes in permissive infection of human cells is principally mediated by the amino acid sequence encoded in the CR3 region of E1A (Lillie et al., 1986 *Cell* 46:1043–1051). Conserved cysteine residues in a $CysX_2CysX_{13}CysX_2Cys$ sequence motif (SEQ ID NO: 30) in the unique region are associated with metal ion binding activity (Berg, 1986 supra) and are essential for transactivation activity (Jelsma et al., 1988 *Virology* 163:494–502; Culp et al., 1988 *PNAS, USA* 85:6450–6454). As well, the amino acids in CR3 which are immediately amino (N)-terminal to the metal binding domain have been shown to be important in transcription activation, while those immediately carboxy (C)-terminal to the metal binding domain are important in forming associations with the promoter region (Lillie and Green, 1989 *Nature* 338:39–44; see FIG. 3).

The application of genetic engineering has resulted in several attempts to prepare adenovirus expression systems for obtaining vaccines. Examples of such research include the disclosures in U.S. Pat. No. 4,510,245 on an adenovirus major late promoter for expression in a yeast host; U.S. Pat. No. 4,920,209 on a live recombinant adenovirus type 7 with a gene coding for hepatitis-B surface antigen located at a deleted early region 3; European patent 389 286 on a non-defective human adenovirus 5 recombinant expression system in human cells for HCMV major envelope glycoprotein; WO 91/11525 on live non-pathogenic immunogenic viable canine adenovirus in a cell expressing E1a proteins; French patent 2 642 767 on vectors containing a leader and/or promoter from the E3 of adenovirus 2.

The selection of a suitable virus to act as a vector for foreign gene expression, and the identification of a suitable non-essential region as a site for insertion of the gene pose a challenge. In particular, the insertion site must be non-essential for the viable replication of the virus and its effective operation in tissue culture and also in vivo. Moreover, the insertion site must be capable of accepting new genetic material, whilst ensuring that the virus continues to replicate. An essential region of a virus genome can also be utilized for foreign gene insertion if the recombinant virus is grown in a cell line which complements the function of that particular essential region in trans.

The present inventors have now identified suitable regions in the BAV genome and have succeeded in inserting foreign genes to generate BAV recombinants.

DISCLOSURE OF THE INVENTION

The present invention relates to novel bovine adenovirus expression vector systems in which part or all of one or both of the E1 and E3 gene regions are deleted and to recombinant mammalian cell lines of bovine origin transformed with the BAV E1 sequences, and thus, constitutively express the E1 gene products to allow bovine adenovirus, having a deletion of part or all of the E1 gene region replaced by a heterologous nucleotide sequence encoding a foreign gene or fragment thereof, to replicate therein and use of these materials in production of heterologous (antigenic) polypeptides or fragments thereof.

The invention also related to a method of preparing a live recombinant virus or subunit vaccines for producing antibodies or cell mediated immunity to an infectious organism in a mammal, such as bovine, which comprises inserting into the bovine adenovirus genome the gene or fragment coding for the antigen which corresponds to said antibodies or induces said cell mediated immunity, together with or without an effective promoter therefore, to produce BAV recombinants.

Generally, the foreign gene construct is cloned into a nucleotide sequence which represents only a part of the entire viral genome having one or more appropriate deletions. This chimeric DNA sequence is usually present in a plasmid which allows successful cloning to produce many copies of the sequence. The cloned foreign gene construct can then be included in the complete viral genome, for example, by in vivo recombination following a DNA-mediated cotransfection technique. Multiple copies of a coding sequence or more than one coding sequences can be inserted so that the recombinant vector can express more than one foreign protein. The foreign gene can have additions, deletions or substitutions to enhance expression and/or immunological effects of the expressed protein.

The invention also includes an expression system comprising an bovine adenovirus expression vector wherein heterologous nucleotide sequences with or without any exogenous regulatory elements, replace the E1 gene region and/or part or all of the E3 gene region.

The invention also includes (A) a recombinant vector system comprising the entire BAV DNA and a plasmid or two plasmids capable of generating a recombinant virus by in vivo recombination following cotransfection of a suitable cell line comprising BAV DNA representing the entire wild-type BAV genome and a plasmid comprising a bovine adenovirus left or right end sequences containing the E1 or E3 gene regions, respectively, with a heterologous nucleotide sequence encoding a foreign gene or fragment thereof substituted for part or all of the E1 or E3 gene regions; (B) a live recombinant bovine adenovirus vector (BAV) system selected from the group consisting of: (a) a system wherein part or all of the E1 gene region is replaced by a heterologous nucleotide sequence encoding a foreign gene or fragment thereof; (b) a system wherein a part or all of the E3 gene region is replaced by a heterologous nucleotide sequence encoding a foreign gene or fragment thereof; and (c) a system wherein part or all of the E1 gene region and part or all of the E3 gene region are deleted and a heterologous nucleotide sequence encoding a foreign gene or fragment thereof is inserted into at least one of the deletions; (C) a recombinant bovine adenovirus (BAV) comprising a deletion of part or all of E1 gene region, a deletion of part or all of E3 gene region or deletion of both, and inserted into at least one deletion a heterologous nucleotide sequence coding for an antigenic determinant of a disease causing organism; (D) a recombinant bovine adenovirus expression system comprising a deletion of part or all of E1, a deletion of part or all of E3, or both deletions, and inserted into at least one deletion a heterologous nucleotide sequence coding for a foreign gene or fragment thereof under control of an expression promoter: or (E) a recombinant bovine adenovirus (BAV) for producing an immune response in a mammalian host comprising: (1) BAV recombinant containing a heterologous nucleotide sequence coding for an antigenic determinant needed to obtain the desired immune response in association with or without (2) an effective promoter to provide expression of said antigenic determinant in immunogenic quantities for use as a live recombinant virus or recombinant protein or subunit vaccine; (F) a mutant bovine adenovirus (BAV) comprising a deletion of part or all of E1 and/or a deletion of part or all of E3.

Recombinant mammalian cell lines stably transformed with BAV E1 gene region sequences, said recombinant cell lines thereby capable of allowing replication therein of a bovine adenovirus comprising a deletion of part or all of the E1 or E3 gene regions replaced by a heterologous or homologous nucleotide sequence encoding a foreign gene or fragment thereof. The invention also includes production, isolation and purification of polypeptides or fragments thereof, such as growth factors, receptors and other cellular proteins from recombinant bovine cell lines expressing BAV E1 gene products.

The invention also includes a method for providing gene therapy to a mammal in need thereof to control a gene deficiency which comprises administering to said mammal a live recombinant bovine adenovirus containing a foreign nucleotide sequence encoding a non-defective form of said gene under conditions wherein the recombinant virus vector genome is incorporated into said mammalian genome or is maintained independently and extrachromosomally to provide expression of the required gene in a target organ or tissue.

Another aspect of the invention provides a virus vaccine composition which comprises the recombinant virus or recombinant protein in association with or without a pharmaceutically acceptable carrier. The recombinant virus vaccine can be formulated for administration by an oral dosage (e.g. as an enteric coated tablet), by injection or otherwise. More specifically, these include a vaccine for protecting a mammalian host against infection comprising a live recombinant adenovirus or recombinant protein produced by the recombinant adenovirus of the invention wherein the foreign gene or fragment encodes an antigen and formulated with or without a pharmaceutically acceptable carrier.

The invention also includes methods of producing antibodies or cell mediated immunity in a mammal including (1) a method for eliciting an immune response in a mammalian host against an infection comprising: administering a vaccine comprising a live BAV recombinant of the invention wherein the foreign gene or fragment encodes an antigen with or without a pharmaceutically acceptable carrier, and (2) a method for eliciting an immune response in a mammalian host against an infection comprising: administering a vaccine comprising a recombinant antigen prepared by culturing a BAV recombinant wherein the foreign gene or fragment encodes the desired antigen with or without a pharmaceutically acceptable carrier.

The following disclosure will render these and other embodiments of the present invention readily apparent to those of skill in the art. While the disclosure often refers to bovine adenovirus type 3 (BAV3), it should be understood that this is for the purpose of illustration and that the same features apply to bovine adenovirus of the other type, 1, 2, 4, 5, 6, 7 8, and 9 and the invention described and claimed herein is intended to cover all of these bovine adenovirus types.

BRIEF DESCRIPTION OF THE DRAWINGS

FIGS. 1A–1L. Sequence and major open reading frames of the left 11% of the BAV3 genome (SEQ ID NO: 1 through SEQ ID NO: 8). The region comprises the E1 and protein IX transcription region. The 195 nucleotide inverted terminal repeat sequence identified by Shinagawa et al., 1987 *Gene* 55:85–93 is shown in italics. The amino acid sequence for the largest E1A protein, two E1B proteins and protein IX are presented. The probable splice donor ([), splice acceptor (]) and intron sequence (underlined italics) within the E1A region are marked. A 35 base pair repeat sequence between E1A and E1B is indicated in bold underline. Possible transcription promoter TATA sequences and possible poly A addition sequences AATAA are also indicated.

FIGS. 2A–2B. Regions of homology in the E1A proteins of BAV3 and human adenovirus type 5 (HAd5). The amino acid residue of each serotype is indicated. A. Conserved region 3 (CR3) of HAd5 (SEQ ID NO: 9) subdivided into three functional regions as defined by Lillie et al (1989) *Nature* 338:39–44 and described in the Background of the Invention. The intron sequence of BAV3 E1A occurs within the serine amino acid codon at position 204 (nucleotide positions 1216–1322 of SEQ ID NO: 1). B. A portion of conserved region 2 (CR2) of HAd5(SEQ ID NO: 10), showing the residues thought to be important in the binding of retinoblastoma protein Rb (Dyson et al., 1990 *J. Virol.* 64:1353–1356), and the comparable sequence from BAV3 (SEQ ID NO: 34).

FIGS. 3A–3B. Homology regions between the HAd5 and E1B 19 k (176R) protein (SEQ ID NO: 11 and SEQ ID NO: 12) and the corresponding BAV3 (157R) protein (amino acid positions 83–99 and 136–142 SEQ ID NO: 4). The amino acid residue number for each of the viruses is indicated.

FIGS. 4A–4B. The C-terminal 346R of HAd5 E1B 56 k (496R) (SEQ ID NO: 13) and the corresponding BAV3 protein (420R) (amino acid positions 74–420 SEQ ID NO: 6). The HAd5 protein comparison begins at residue 150 and the BAV3 (in italics) at residue 74. The amino terminal regions of these proteins which are not presented show no significant homology.

FIG. 5. Homology comparison of the amino acid sequence of HAd5 protein IX (SEQ ID NO: 14) and the corresponding protein of BAV3 (SEQ ID NO: 8) (in italics).

FIG. 6. The genome of BAV3 showing the location of EcoRI, XbaI and BAMHI sites and the structure of the 5100 bp segment from 77 to 92 m.u. ORFs for the upper strand which can encode 60 amino acids or more are represented by bars. Shaded portions indicate regions of similarity to pVIII, 14.7K E3 and fibre proteins of HAd2 or -5. The first methionine followed by a stretch of amino acids of at least 50 is shown by an open triangle. Termination codons for ORFs likely to code for viral proteins are shown by closed triangles.

FIGS. 7A–7R. Nucleotide sequence of BAV3 between 77 and 92 m.u. (SEQ ID NO: 15 through SEQ ID NO: 26) showing ORFs that have the potential to encode polypeptides of at least 50 amino acids after the initiating methionine. The nucleotide sequence was analyzed using the program DISPCOD (PC/GENE). Potential N-glycosylation sites (N-X-T/S) and polyadenylation signals are underlined and the first methionine of each ORF is shown in bold.

FIGS. 8A–8C-3. Comparison between the predicted amino acid sequences for the ORFs of BAV3 and known proteins of HAd2 or -5 using the computer program PALIGN (PC/GENE), with comparison matrix structural-genetic matrix; open gap cost 6; unit gap cost 2. Identical residues are indicated by a colon and similar residues by a dot. (a) Comparison between the predicted amino acid sequence encoded by the 3' end of BAV3 ORF 1 (SEQ ID NO: 16) and the HAd2 hexon-associated pVIII precursor (SEQ ID NO: 27). (b) Comparison between the ORF 4 (amino acid positions 34–154 SEQ ID NO: 22) and the HAd5 14.7K E3 (SEQ ID NO: 28) protein. (c) Comparison between the predicted amino acid sequence encoded by BAV3 ORF 6 (amino acid positions 8–983 SEQ ID NO: 26) and the HAd2 fibre protein (SEQ ID NO: 29).

FIGS. 11A–11B. Southern blot analyses of restriction enzymes digested DNA fragments of the wt BAV3 or recombinant genomes by using a 696 bp XhoI-NcoI fragment from pSM14 (FIG. 9) and a DNA fragment containing the luciferase gene as probes. 100 ng DNA isolated from the mock (lanes 1, 2, 3), BAV3-Luc (3.1) (lanes 4, 5, 6), BAV3-Luc (3.2) (lanes 7, 8, 9) or wt BAV3 (lanes 10, 11 12)-infected MDBK cells were digested with BamHI (lanes 1, 4, 7, 10), EcoRI (lanes 2, 5, 8, 11) or XbaI (lanes 3, 6, 9, 12) and analyzed by agarose gel electrophoresis. The DNA fragments from the gel were transferred onto a GeneScreen-Plus™ membrane and hybridized with a 696 bp XhoI-NcoI fragment from pSM14 (FIG. 9) labeled with $^{32}$P using Pharmacia Oligolabeling Kit (panel A). Panel B blot represents duplicate samples as in panel A but was probed with a 1716 bp BsmI-SspI fragment containing the luciferase gene (FIG. 9). The sizes of bands visualized following hybridization are shown in kb on the right in panel A and on the left in panel B.
B: BamHI, E: EcoRI, Xb: XbaI, 3.1: BAV3-Luc (3.1), 3.2: BAV3-Luc (3.2) and wt: wild-type BAV3.

FIG. 16. Western blot analysis of virus-infected MDBK cells using an anti-luciferase antibody. Confluent monolayers of MDBK cells were mock-infected (lane 1) or infected with the wt BAV3 (lane 2), BAV3-Luc (3.1) (lane 3) and BAV3-Luc (3.2) (lane 4) at a m.o.i. of 50 p.f.u. per cell, harvested at 18 h post-infection, cell extracts prepared and analyzed by SDS-PAGE and Western blotting using a rabbit anti-luciferase antibody. Purified firefly luciferase was used as a positive control (lane 5). The lane 5 was excised to obtain a shorter exposure. The protein molecular weight markers in kDa are shown on the left. The arrow indicates the 62 kDa luciferase bands reacted with the anti-luciferase antibody.

wt: wild-type BAV3, 3.1: BAV3-Luc (3.1) and 3.2: BAV3-Luc (3.2).

Figure 17:
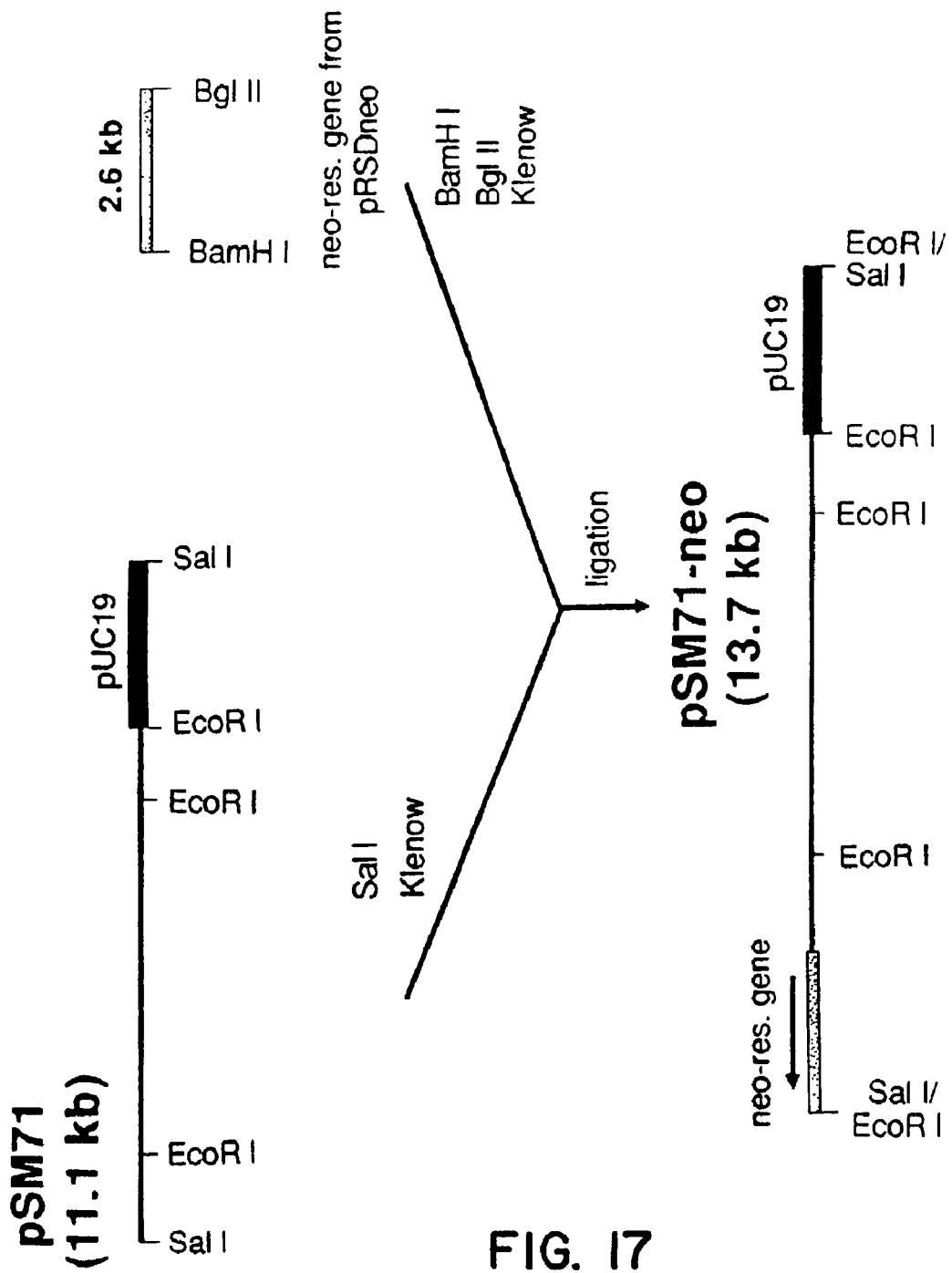

FIG. 17. Construction of pSM71-neo. A 8.4 kb SalI fragment of the BAV3 genome which falls between m.u. 0 and 24 was isolated and inserted into pUC19 at the SalI-SmaI site to generate pSM71. The plasmid, pRSDneo (Fitzpatrick et al (1990) *Virology* 176:145–157) contains the neomycin-resistant (neo$^r$ gene flanked with the simian virus 40 (SV40) regulatory sequences originally from the plasmid, pSV2 neo (Southern et al (1982) *J. Mol. Appl. Genet* 1:327–341) after deleting a portion of the SV40 sequences upstream of the neo$^r$ gene to remove several false initiation codons. A 2.6 kb fragment containing the neo$^r$ gene under the control of the SV40 regulatory sequences, was obtained from the plasmid, pRSDneo after digestion with BamHI and BgIII, and cloned into pSM71 at the SalI site by blunt end ligation to obtain pSM71-neo containing the neo$^r$ gene in the E1 parallel orientation.

Figure 18:
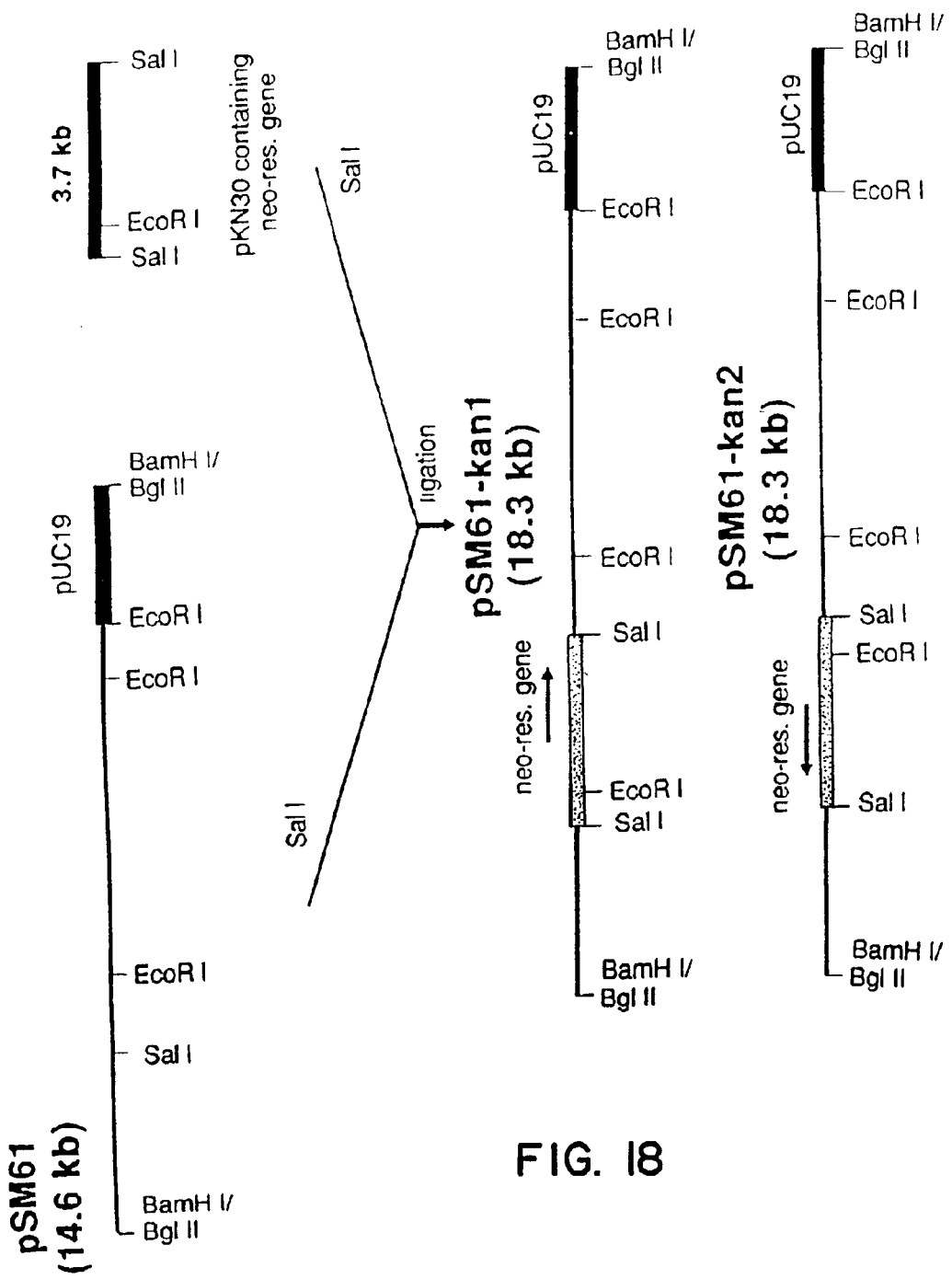

FIG. 18. Construction of pSM61-kan 1 and pSM61-kan2. A 11.9 kb BgIII fragment of the BAV3 genome which extends between m.u. 0 and 34 was purified and introduced into pUC19 at the BamHI-HincII site to obtain pSM61. The plasmid, pKN30 contains the neo$^r$ gene along with SV40 promoter and polyadenylation sequences from the plasmid pSV2neo without any modification. The entire pKN30 plasmid was inserted into pSM61 at the SalI site to generate pSM61-kan1 having the neo$^r$ gene in the E1 anti-parallel orientation and pSM61-kan2 when the neo$^r$ gene is in the E1 parallel orientation.

Figure 19:
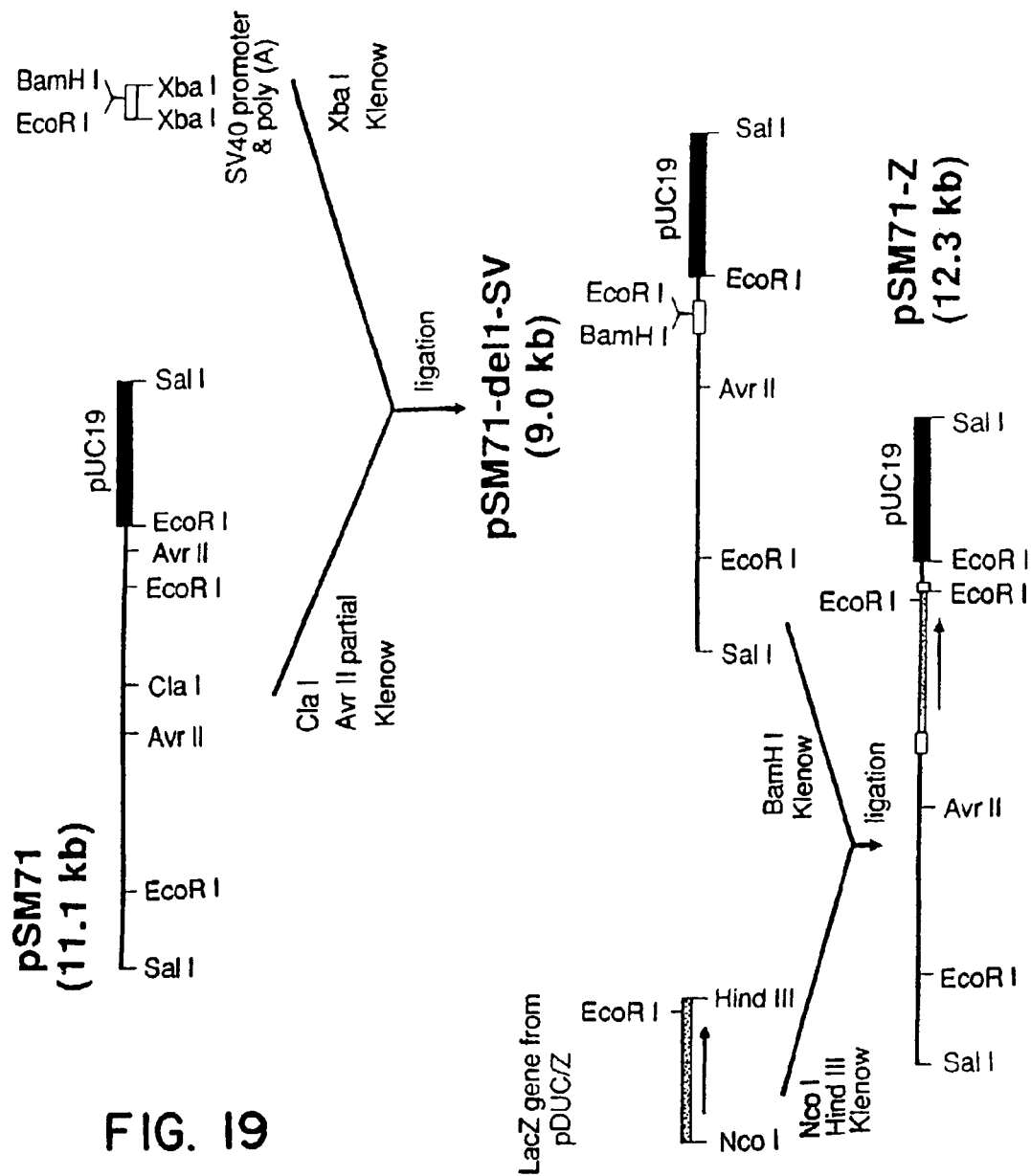

FIG. 19. Construction of an E1 transfer plasmid containing the beta-galactosidase gene.

The plasmid, pSM71 which contains the BAV3 genome between m.u. 0 and 24, was cleaved with ClaI and partially with AvrII to delete a 2.6 kb AvrII-ClaI fragment (between m.u. 1.3 and 8.7) which falls within the E1 region. A 0.5 kb fragment containing the SV40 promoter and polyadenylation sequences was obtained from pFG144K5-SV by digesting with XbaI and inserted into pSM71 to replace the 2.6 kb deletion to generate pSM71-del1-SV. A 3.26 kb fragment containing the bacterial beta-galactosidase gene was isolated from pDUC/Z (Liang et al (1993) *Virology* 195:42–50) after cleavage with NcoI and HindIII and cloned into pSM71-del1-SV at the BamHI site to put the beta-galactosidase gene under the control of the SV40 regulatory sequences to obtain pSM71-Z.

MODES OF CARRYING OUT THE INVENTION

The practice of the present invention will employ, unless otherwise indicated, conventional microbiology, immunology, virology, molecular biology, and recombinant DNA techniques which are within the skill of the art. These techniques are fully explained in the literature. See e.g., Maniatis et al., *Molecular Cloning: A Laboratory Manual* (1982); *DNA Cloning: A Practical Approach*, vols. I & II (D. Glover, ed.); *Oligonucleotide Synthesis* (N. Gait, ed. (1984)); *Nucleic Acid Hybridization* (B. Hames & S. Higgins, eds. (1985)); *Transcription and Translation* (B. Hames & S. Higgins, eds. (1984)); *Animal Cell Culture* (R. Freshney, ed. (1986)); Perbal, *A Practical Guide to Molecular Cloning* (1984). Sambrook et al., Molecular Cloning: A Laboratory Manual (2nd Edition); vols. I, II & III (1989).

A. Definitions

In describing the present invention, the following terminology, as defined below, will be used.

A "replicon" is any genetic element (e.g., plasmid, chromosome, virus) that functions as an autonomous unit of DNA replication in vivo; i.e., is capable of replication under its own control.

A "vector" is a replicon, such as a plasmid, phage, cosmid or virus, to which another DNA segment may be attached so as to bring about the replication of the attached segment.

By "live virus" is meant, in contradistinction to "killed" virus, a virus which is capable of producing identical progeny in tissue culture and inoculated animals.

A "helper-free virus vector" is a vector that does not require a second virus or a cell line to supply something defective in the vector.

A "double-stranded DNA molecule" refers to the polymeric form of deoxyribonucleotides (adenine, guanine, thymine, or cytosine) in its normal, double-stranded helix. This term refers only to the primary and secondary structure of the molecule, and does not limit it to any particular tertiary forms. Thus, this term includes double-stranded DNA found, inter alia, in linear DNA molecules (e.g., restriction fragments of DNA from viruses, plasmids, and chromosomes). In discussing the structure of particular double-stranded DNA molecules, sequences may be described herein according to the normal convention of giving only the sequence in the 5' to 3' direction along the nontranscribed strand of DNA (i.e., the strand having the sequence homologous to the mRNA).

A DNA "coding sequence" is a DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, procaryotic sequences, cDNA from eucaryotic mRNA, genomic DNA sequences from eucaryotic (e.g., mammalian) DNA, viral DNA, and even synthetic DNA sequences. A polyadenylation signal and transcription termination sequence will usually be located 3' to the coding sequence.

A "transcriptional promoter sequence" is a DNA regulatory region capable of binding RNA polymerase in a cell and initiating transcription of a downstream (3' direction) coding sequence. For purposes of defining the present invention, the promoter sequence is bound at the 3' terminus by the translation start codon (ATG) of a coding sequence and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eucaryotic promoters will often, but not always, contain "TATA" boxes and "CAAT" boxes. Procaryotic promoters contain Shine-Dalgarno sequences in addition to the −10 and −35 consensus sequences.

DNA "control sequences" refer collectively to promoter sequences, ribosome binding sites, polyadenylation signals, transcription termination sequences, upstream regulatory domains, enhancers, and the like, which collectively provide for the transcription and translation of a coding sequence in a host cell.

A coding sequence or sequence encoding is "operably linked to" or "under the control of" control sequences in a cell when RNA polymerase will bind the promoter sequence and transcribe the coding sequence into mRNA, which is then translated into the polypeptide encoded by the coding sequence.

A "host cell" is a cell which has been transformed, or is capable of transformation, by an exogenous DNA sequence.

A cell has been "transformed" by exogenous DNA when such exogenous DNA has been introduced inside the cell membrane. Exogenous DNA may or may not be integrated (covalently linked) to chromosomal DNA making up the genome of the cell. In procaryotes and yeasts, for example, the exogenous DNA may be maintained on an episomal element, such as a plasmid. A stably transformed cell is one in which the exogenous DNA has become integrated into the chromosome so that it is inherited by daughter cells through chromosome replication. For mammalian cells, this stability is demonstrated by the ability of the cell to establish cell lines or clones comprised of a population of daughter cell containing the exogenous DNA.

A "clone" is a population of daughter cells derived from a single cell or common ancestor. A "cell line" is a clone of a primary cell that is capable of stable growth in vitro for many generations.

Two polypeptide sequences are "substantially homologous" when at least about 80% (preferably at least about 90%, and most preferably at least about 95%) of the amino acids match over a defined length of the molecule.

Two DNA sequences are "substantially homologous" when they are identical to or not differing in more that 40% of the nucleotides, more preferably about 20% of the nucleotides, and most preferably about 10% of the nucleotides.

DNA sequences that are substantially homologous can be identified in a Southern hybridization experiment under, for example, stringent conditions, as defined for that particular system. Defining appropriate hybridization conditions is within the skill of the art. See, e.g., Maniatis et al., supra; *DNA Cloning*, vols. I & II, supra; *Nucleic Acid Hybridization*, supra.

A "heterologous" region of a DNA construct is an identifiable segment of DNA within or attached to another DNA molecule that is not found in association with the other molecule in nature. Thus, when the heterologous region encodes a viral gene, the gene will usually be flanked by DNA that does not flank the viral gene in the genome of the source virus or virus-infected cells. Another example of the heterologous coding sequence is a construct where the coding sequence itself is not found in nature (e.g., synthetic sequences having codons different from the native gene). Allelic variation or naturally occurring mutational events do not give rise to a heterologous region of DNA, as used herein.

"Bovine host" refers to cattle of any breed, adult or infant.

The term "protein"0 is used herein to designate a polypeptide or glycosylated polypeptide, respectively, unless otherwise noted. The term "polypeptide" is used in its broadest sense, i.e., any polymer of amino acids (dipeptide or greater) linked through peptide bonds. Thus, the term "polypeptide" includes proteins, oligopeptides, protein fragments, analogs, muteins, fusion proteins and the like.

"Fusion protein" is usually defined as the expression product of a gene comprising a first region encoding a leader sequence or a stabilizing polypeptide, and a second region encoding a heterologous protein. It involves a polypeptide comprising an antigenic protein fragment or a full length BAV protein sequence as well as (a) heterologous sequence (s), typically a leader sequence functional for secretion in a recombinant host for intracellularly expressed polypeptide, or an N-terminal sequence that protects the protein from host cell proteases, such as SOD. An antigenic protein fragment is usually about 5–7 amino acids in length.

"Native" proteins or polypeptides refer to proteins or polypeptides recovered from BAV or BAV-infected cells. Thus, the term "native BAV polypeptide" would include naturally occurring BAV proteins and fragments thereof. "Non-native" polypeptides refer to polypeptides that have been produced by recombinant DNA methods or by direct synthesis. "Recombinant" polypeptides refers to polypeptides produced by recombinant DNA techniques; i.e., produced from cells transformed by an exogenous DNA construct encoding the desired polypeptide.

A "substantially pure" protein will be free of other proteins, preferably at least 10% homogeneous, more preferably 60% homogeneous, and most preferably 95% homogeneous.

An "antigen" refers to a molecule containing one or more epitopes that will stimulate a host's immune system to make a humoral and/or cellular antigen-specific response. The term is also used interchangeably with "immunogen."

A "hapten" is a molecule containing one or more epitopes that does not stimulate a host's immune system to make a humoral or cellular response unless linked to a carrier.

The term "epitope" refers to the site on an antigen or hapten to which a specific antibody molecule binds or is recognized by T cells. The term is also used interchangeably with "antigenic determinant" or "antigenic determinant site."

An "immunological response" to a composition or vaccine is the development in the host of a cellular and/or antibody-mediated immune response to the composition or vaccine of interest. Usually, such a response consists of the subject producing antibodies, B cells, helper T cells, suppressor T cells, and/or cytotoxic T cells directed specifically to an antigen or antigens included in the composition or vaccine of interest.

The terms "immunogenic polypeptide" and "immunogenic amino acid sequence" refer to a polypeptide or amino acid sequence, respectively, which elicit antibodies that neutralize viral infectivity, and/or mediate antibody-complement or antibody dependent cell cytotoxicity to provide protection of an immunized host. An "immunogenic polypeptide" as used herein, includes the full length (or near full length) sequence of the desired protein or an immunogenic fragment thereof.

By "immunogenic fragment" is meant a fragment of a polypeptide which includes one or more epitopes and thus elicits antibodies that neutralize viral infectivity, and/or mediates antibody-complement or antibody dependent cell cytotoxicity to provide protection of an immunized host. Such fragments will usually be at least about 5 amino acids in length, and preferably at least about 10 to 15 amino acids in length. There is no critical upper limit to the length of the fragment, which could comprise nearly the full length of the protein sequence, or even a fusion protein comprising fragments of two or more of the antigens. The term "treatment" as used herein refers to treatment of a mammal, such as bovine or the like, either (i) the prevention of infection or reinfection (prophylaxis), or (ii) the reduction or elimination of symptoms of an infection. The vaccine comprises the recombinant BAV itself or recombinant antigen produced by recombinant BAV.

By "infectious" is meant having the capacity to deliver the viral genome into cells.

B. General Method

The present invention identifies and provides a means of deleting part or all of the nucleotide sequence of bovine adenovirus E1 and/or E3 gene regions to provide sites into which heterologous or homologous nucleotide sequences encoding foreign genes or fragments thereof can be inserted to generate bovine adenovirus recombinants. By "deleting part of" the nucleotide sequence is meant using conventional genetic engineering techniques for deleting the nucleotide sequence of part of the E1 and/or E3 region.

Various foreign genes or coding sequences (prokaryotic, and eukaryotic) can be inserted in the bovine adenovirus nucleotide sequence, e.g.,DNA, in accordance with the present invention, particularly to provide protection against a wide range of diseases and many such genes are already known in the art. The problem heretofore having been to provide a safe, convenient and effective vaccine vector for the genes or coding sequences.

It is also possible that only fragments of nucleotide sequences of genes can be used (where these are sufficient to generate a protective immune response) rather than the complete sequence as found in the wild-type organism. Where available, synthetic genes or fragments thereof can also be used. However, the present invention can be used with a wide variety of genes, fragment and the like, and is not limited to those set out above.

In some cases the gene for a particular antigen can contain a large number of introns or can be from an RNA virus, in these cases a complementary DNA copy (cDNA) can be used.

In order for successful expression of the gene to occur, it can be inserted into an expression vector together with a suitable promoter including enhancer elements and polyadenylation sequences. A number of eucaryotic promoter and polyadenylation sequences which provide successful expression of foreign genes in mammalian cells and how to construct expression cassettes, are known in the art, for example in U.S. Pat. No. 5,151,267, the disclosures of which are incorporated herein by reference. The promoter is selected to give optimal expression of immunogenic protein which in turn satisfactorily leads to humoral, cell mediated and mucosal immune responses according to known criteria.

The foreign protein produced by expression in vivo in a recombinant virus-infected cell may be itself immunogenic. More than one foreign gene can be inserted into the viral genome to obtain successful production of more than one effective protein.

Thus with the recombinant virus of the present invention, it is possible to provide protection against a wide variety of diseases affecting cattle. Any of the recombinant antigenic determinant or recombinant live virus of the invention can be formulated and used in substantially the same manner as described for the antigenic determinant vaccines or an live vaccine vectors.

The antigens used in the present invention can be either native or recombinant antigenic polypeptides or fragments. They can be partial sequences, full-length sequences, or even fusions (e.g., having appropriate leader sequences for the recombinant host, or with an additional antigen sequence for another pathogen). The preferred antigenic polypeptide to be expressed by the virus systems of the present invention contain full-length (or near full-length) sequences encoding antigens. Alternatively, shorter sequences that are antigenic (i.e., encode one or more epitopes) can be used. The shorter sequence can encode a "neutralizing epitope," which is defined as an epitope capable of eliciting antibodies that neutralize virus infectivity in an in vitro assay. Preferably the peptide should encode a "protective epitope" that is capable of raising in the host an "protective immune response;" i.e., an antibody- and/or a cell-mediated immune response that protects an immunized host from infection.

The antigens used in the present invention, particularly when comprised of short oligopeptides, can be conjugated to a vaccine carrier. Vaccine carriers are well-known in the art: for example, bovine serum albumin (BSA), human serum albumin (HSA) and keyhole limpet hemocyanin (KLH). A preferred carrier protein, rotavirus VP6, is disclosed in EPO Pub. No. 0259149, the disclosure of which is incorporated by reference herein.

Genes for desired antigens or coding sequences thereof which can be inserted include those of organisms which cause disease in mammals, particularly bovine pathogens such as bovine rotavirus, bovine coronavirus, bovine herpes virus type 1, bovine respiratory syncytial virus, bovine parainfluenza virus type 3 (BPI-3), bovine diarrhea virus, *Pasteurella haemolytica, Haemophilus somnus* and the like. The vaccines of the invention carrying foreign genes or fragments can also be orally administered in a suitable oral carrier, such as in an enteric-coated dosage form. Oral formulations include such normally-employed excipients as, for example, pharmaceutical grades of mannitol, lactose, starch, magnesium stearate, sodium saccharin cellulose, magnesium carbonate, and the like. Oral vaccine compositions may be taken in the form of solutions, suspensions, tablets, pills, capsules, sustained release formulations, or powders, containing from about 10% to about 95% of the active ingredient, preferably about 25% to about 70%. An oral vaccine may be preferable to raise mucosal immunity in combination with systemic immunity, which plays an important role in protection against pathogens infecting the gastrointestinal tract.

In addition, the vaccine be formulated into a suppository. For suppositories, the vaccine composition will include traditional binders and carriers, such as polyalkaline glycols or triglycerides. Such suppositories may be formed from mixtures containing the active ingredient in the range of about 0.5% to about 10% (w/w), preferably about 1% to about 2%.

Protocols for administering to animals the vaccine composition(s) of the present invention are within the skill of the art in view of the present disclosure. Those skilled in the art will select a concentration of the vaccine composition in a dose effective to elicit an antibody and/or T-cell mediated immune response to the antigenic fragment. Within wide limits, the dosage is not believed to be critical. Typically, the vaccine composition is administered in a manner which will deliver between about 1 to about 1,000 micrograms of the subunit antigen in a convenient volume of vehicle, e.g., about 1–10 cc. Preferably, the dosage in a single immunization will deliver from about 1 to about 500 micrograms of subunit antigen, more preferably about 5–10 to about 100–200 micrograms (e.g., 5–200 micrograms).

The timing of administration may also be important. For example, a primary inoculation preferably may be followed by subsequent booster inoculations if needed. It may also be preferred, although optional, to administer a second, booster immunization to the animal several weeks to several months after the initial immunization. To insure sustained high levels of protection against disease, it may be helpful to readminister a booster immunization to the animals at regular intervals, for example once every several years. Alternatively, an initial dose may be administered orally followed by later inoculations, or vice versa. Preferred vaccination protocols can be established through routine vaccination protocol experiments.

The dosage for all routes of administration of in vivo recombinant virus vaccine depends on various factors including, the size of patient, nature of infection against which protection is needed, carrier and the like and can readily be determined by those of skill in the art. By way of non-limiting example, a dosage of between $10^3$ pfu and $10^8$ pfu and the like can be used. As with in vitro subunit vaccines, additional dosages can be given as determined by the clinical factors involved.

In one embodiment of the invention, a number of recombinant cell lines are produced according to the present invention by constructing an expression cassette comprising the BAV E1 region and transforming host cells therewith to provide cell lines or cultures expressing the E1 proteins. These recombinant cell lines are capable of allowing a recombinant BAV, having an E1 gene region deletion replaced by heterologous nucleotide sequence encoding for a foreign gene or fragment, to replicate and express the desired foreign-gene or fragment thereof which is encoded within the recombinant BAV. These cell lines are also extremely useful in generating recombinant BAV, having an E3 gene deletion replaced by heterologous nucleotide sequence encoding for a foreign gene or fragment, by in vivo recombination following DNA-mediated cotransfection.

In one embodiment of the invention, the recombinant expression cassette can be obtained by cleaving the wild-type BAV genome with an appropriate restriction enzyme to produce a DNA fragment representing the left end or the right end of the genome comprising E1 or E3 gene region sequences, respectively and inserting the left or right end fragment into a cloning vehicle, such as plasmid and thereafter inserting at least one DNA sequence encoding a foreign protein, into E1 or E3 deletion with or without the control of an exogenous promoter. The recombinant expression cassette is contacted with the wild-type BAV DNA through homologous recombination or other conventional genetic engineering method within an E1 transformed cell line to obtain the desired recombinant.

The invention also includes an expression system comprising an bovine adenovirus expression vector wherein a heterologous nucleotide, e.g. DNA, replaces part or all of the E3 region and/or part or all of the E1 region. The expression system can be used wherein the foreign nucleotide sequences, e.g. DNA, is with or without the control of any other heterologous promoter.

The BAV E1 gene products of the adenovirus of the invention transactivate most of the cellular genes, and therefore, cell lines which constitutively express E1 proteins can express cellular polypeptides at a higher level than normal cell lines. The recombinant mammalian, particularly bovine, cell lines of the invention can be used to prepare and isolate polypeptides, including those such as (a) proteins associated with adenovirus E1A proteins: e.g. p300, retinoblastoma(Rb) protein, cyclins, kinases and the like.; (b) proteins associated with adenovirus E1B protein: e.g. p53 and the like.; (c) growth factors, such as epidermal growth factor (EGF), transforming growth factor (TGF) and the like; (d) receptors such as epidermal growth factor receptor (EGF-R), fibroblast growth factor receptor (FGF-R), tumor necrosis factor receptor (TNF-R), insulin-like growth factor receptor (IFG-R), major histocompatibility complex class I receptor and the like; (e) proteins encoded by proto-oncogenes such as protein kinases (tyrosine-specific protein kinases and protein kinases specific for serine or threonine), p21 proteins (guanine nucleotide-binding proteins with GTPase activity and the like; (f) other cellular proteins such as actins, collagens, fibronectins, integrins, phospholipids, proteoglycans, histones and the like, and (g) proteins involved in regulation of transcription such as TATA-box-binding protein (TBP), TBP-associated factors (TAFs). SP1 binding protein and the like.

The invention also includes a method for providing gene therapy to a mammal in need thereof to control a gene deficiency which comprises administering to said mammal a live recombinant bovine adenovirus containing a foreign nucleotide sequence encoding a non-defective form of said gene under conditions wherein the recombinant virus vector genome is incorporated into said mammalian genome or is maintained independently and extrachromosomally to provide expression of the required gene in the target organ or tissue. These kinds of techniques are recently being used by those of skill in the art to replace a defective gene or portion thereof. Examples of foreign genes nucleotide sequences or portions thereof that can be incorporated for use in a conventional gene therapy include, cystic fibrosis transmembrane conductance regulator gene, human minidystrophin gene, alpha1-antitrypsin gene and the like.

EXAMPLES

Described below are examples of the present invention. These examples are provided only for illustrative purposes and are not intended to limit the scope of the present invention in any way. In light of the present disclosure, numerous embodiments within the scope of the claims will be apparent to those of ordinary skill in the art. The contents of the references cited in the specification are incorporated by reference herein.

Cells and Viruses

Cell culture media and reagents were obtained from GIBCO/BRL Canada (Burlington, Ontario, Canada). Media were supplemented with 25 mM Hepes and 50 µg/ml gentamicin. MDBK cells or MDBK cells transformed with a plasmid containing BAV3 E1 sequences were grown in MEM supplemented with 10% Fetal bovine serum. The wild-type BAV3 ((strain WBR-1) (Darbyshire et al, 1965 *J. Comparative Pathology* 75:327) was kindly provided by Dr. B. Darbyshire, University of Guelph, Guelph, Canada) and BAV3-luciferase recombinants working stocks and virus titrations were done in MDBK cells.

Enzymes, Bacteria and Plasmids

Restriction endonucleases, polymerase chain reaction (PCR) and other enzymes required for DNA manipulations were purchased from Pharmacia LKB Biotechnology (Canada) Ltd. (Dorval, Quebec, Canada), Boehringer-Mannheim, Inc. (Laval or Montreal, Quebec, Canada), New England BioLabs (Beverly, Mass.), or GIBCO/BRL Canada (Burlington, Ontario, Canada) and used as per manufacturer's instructions. Restriction enzyme fragments of BAV3 DNA were inserted into pUC18 or pUC19 (Yanich-Penon et al (1985) *Gene* 33:103–109) following standard procedures (Sambrook et al (1989) *Molecular Cloning: A Laboratory Manual*, 2nd ed. Cold Spring Harbour Laboratory, New York). *E. coli* strain DH5 (supE44 hsdR17 recA1 endA1 gyrA96 thi-1 relA1) was transformed with recombinant plasmids by electroporation (Dower et al. (1988) *Nuc. Acids Res.*, 16:6127–6145). Plasmid DNA was prepared using the alkaline lysis procedure (Bernboim and Doly (1978) *Nuc. Acids Res.*, 7:1513–1523). The plasmid, pSVOA/L containing the entire cDNA encoding firefly luciferase (de Wet et al (1987) *Mol. Cell. Biol.* 7:725–737), was a gift from D. R. Helinski, University of California, San Diego, La Jolla, Calif.

Construction of Recombinant BAV3

MDBK cells transformed with a plasmid containing BAV3 E1 sequences were cotransfected with the wt BAV3 DNA digested with PvuI and the plasmid, pSM51-Luc (FIGS. 9 and 10) using the lipofection-mediated cotransfection protocol (GIBCO/BRL, Life Technologies, Inc., Grand Island, N.Y.). The virus plaques produced following cotransfection were isolated, plaque purified and the presence of the luciferase gene in the BAV3 genome was detected by agarose gel electrophoresis of recombinant virus DNA digested with appropriate restriction enzymes.

Southern Blot and Hybridization

Mock or virus-infected MDBK cells were harvested in lysis buffer (500 µg/ml pronase in 0.01 M Tris, pH 7.4, 0.01 M EDTA, 0.5% SDS) and DNA was extracted (Graham et al (1991) Manipulation of adenovirus vectors In: Methods and Molecular Biology, 7:Gene Transfer and Expression Techniques (Eds. Murray and Walker) Humana Press, Clifton, N.J. pp. 109–128). 100 ng DNA was digested either with BamHI, EcoRI or XbaI and resolved on a 1% agarose gel by electrophoresis. DNA bands from the agarose gel were transferred to a GeneScreenPlus™ membrane (Du Pont Canada Inc. (NEN Products), Lachine, Quebec, Canada) by the capillary blot procedure (Southern, E. M. (1975) *J. Mol. Biol.* 98:503–517). Probes were labeled with $^{32}$P using an Oligolabeling Kit (Pharmacia LKB Biotechnology (Canada) Ltd., Dorval, Quebec, Canada) and the unincorporated label was removed by passing the labeled probe through a sephadex G-50 column (Sambrook et al (1989) supra). Probes were kept in a boiling water bath for 2 min and used in hybridization experiments following GeneScreenPlus™ hybridization protocol. The DNA bands which hybridized with the probe were visualized by autoradiography.

Luciferase Assays

The protocol was essentially the same as described (Mittal et al (1993) *Virus Res.* 28:67–90). Briefly, MDBK cell monolayers in 25 mm multi-well dishes (Corning Glass Works, Corning, N.Y.) were infected in duplicate either with BAV3-Luc (3.1) or BAV3-Luc (3.2) at a m.o.i. of 50 p.f.u. per cell. At indicated time points post-infection, recombinant virus-infected cell monolayers were washed once with PBS (0.137 M NaCl, 2.7 mM KCl, 8 mM $Na_2HPO_4$, 1.5 mM $KH_2PO_4$) and harvested in 1 ml luciferase extraction buffer (100 mM potassium phosphate, pH 7.8, 1 mM dithiothreitol). The cell pellets were resuspended in 200 µl of luciferase extraction buffer and lysed by three cycles of freezing and thawing. The supernatants were assayed for luciferase activity. For the luciferase assay, 20 µl of undiluted or serially diluted cell extract was mixed with 350 µl of luciferase assay buffer (25 mM glycylglycine, pH 7.8, 15 mM $MgCl_2$, 5 mM ATP) in a 3.5 ml tube (Sarstedt Inc., St-Laurent, Quebec, Canada). Up to 48 tubes can be kept in the luminometer rack and the equipment was programed to inject 100 µl of luciferin solution (1 mM luciferin in 100 mM potassium phosphate buffer, pH 7.8) in the tube present in the luminometer chamber to start the enzyme reaction. The Luminometer (Packard Picolite Luminometer, Packard Instrument Canada, Ltd., Mississauga, Ontario, Canada) used in the present study produced 300 to 450 light units of background count in a 10 sec reaction time. Known amounts of the purified firefly luciferase were used in luciferase assays to calculate the amount of active luciferase present in each sample.

Western Blotting

Mock or virus-infected MDBK cells were lysed in 1:2 diluted 2× loading buffer (80 mM Tris-HCl, pH 6.8, 0.67 M urea, 25% glycerol, 2.5% SDS, 1 M mercaptoethanol, 0.001% bromophenol blue), boiled for 3 min and then centrifuged to pellet cell debris. Proteins were separated by SDS-polyacrylamide gel electrophoresis (SDS-PAGE) on 0.1% SDS-10% polyacrylamide gels (Laemmli, et al (1970) *Nature* 227:680–685). After the end of the run, polypeptide bands in the gel were electrophoretically transferred to a nitrocellulose membrane (Bio-Rad Laboratories, Richmond, Calif.). The membrane was incubated at room temperature for 2 h with 1:4000 diluted rabbit anti-luciferase antibody (Mittal et al (1993) supra). The binding of anti-luciferase antibody to the specific protein band/s on the membrane was detected with 1:5000 diluted horseradish peroxidase conjugated-goat anti-rabbit IgG (Bio-Rad Laboratories, Richmond, Calif.) and with an ECL Western blotting detection system (Amersham Canada Ltd., Oakville, Ontario).

Example 1

Cloning of BAV3 E1 Region DNA for Sequencing

To complement the restriction site (Kurokawa et al, 1978 *J. Virol.*, 28:212–218; Hu et al, 1984 *J. Virol.* 49:604–608) other restriction enzyme sites in the BAV3 genome were defined. The 8.4 kilobase pair (kb) SalI B fragment which extends from the left end of the genome to approximately 24% was cloned into the SmaI-SalI sites of pUC18 essentially as described previously (Graham et al, 1989 *EMBO Journal* 8:2077–2085). Beginning at the left end of the BAV3 genome, the relevant restriction sites used for subsequent subcloning and their approximate positions are: SacI (2%), EcoRI (3.5%), HindIII (5%), SacI (5.5%), SmaI (5.6%) and HindIII (11%). Through the use of appropriate restriction enzymes, the original plasmid was collapsed to contain smaller inserts which could be sequenced using the pUC universal primers. Some fragments were also subcloned in both pUC18 and pUC19 to allow confirmational sequencing in both directions. These procedures, together with the use of twelve different oligonucleotide primers hybridizing with BAV3 sequences, allowed to sequence the BAV3 genome from its left end to the HindIII site at 11%.

To ensure that some features of the sequence obtained were not unique to the initial clone selected for sequencing, two more pUC19 clones were prepared containing the SalI fragment from a completely independent DNA preparation. These clones were used to confirm the original sequence for the region from approximately 3% to 5.5% of the BAV3 genome.

DNA sequencing reactions were based on the chain-termination method (Sanger et al. 1977 *PNAS, USA* 74:5463–5467) and manual sequencing followed the DNA sequencing protocol described in the Sequenase™ kit produced by US Biochemical. [$\alpha$-$^{35}$S]dATPs was obtained from Amersham Canada Ltd. All oligonucleotides used as primers were synthesized by the Central Facility of the Molecular Biology and Biotechnology Institute (MOBIX) at McMaster University, Hamilton, Ontario. The entire region (0 to 11%) of the BAV3 genome was sequenced by at least two independent determinations for each position by automated sequencing on a 373A DNA Sequencer (Applied Biosystems) using Taq-Dye terminators. Over half of the region was further sequenced by manual procedures to confirm overlaps and other regions of interest.

DNA sequence analysis and protein comparisons were carried out on a MICROGENIE program.

Example 2

Coding Sequences of the BAV3 E1 Region

BAV3 genomic DNA, from the left end of the genome to the HindIII site at approximately 11%, was cloned into plasmids and sequenced by a combination of manual and automated sequencing. An examination of the resultant BAV3 E1 genomic sequence (FIG. 1) revealed a number of interesting features relevant both to transactivation and to other functions associated with adenovirus E1 proteins. On the basis of open reading frames (ORFs) it was possible to assign potential coding regions analogous to those defined in human Ad5 (HAd5). As shown in FIG. 1, ORFs corresponding roughly to the first exon and unique region of HAd5 E1A as well are ORFs corresponding to the 19 k and 58 k proteins of E1B and the ORF corresponding to protein IX were all defined in this sequence. The open reading frame defining the probable E1A coding region begins at the ATG at nt 606 and continues to a probable splice donor site at position 1215. The first consensus splice acceptor site after this is located after nt 1322 and defines an intron of 107 base pairs with an internal consensus splice branching site at position 1292. The putative BAV3 E1A polypeptide encoded by a message corresponding to these splice sites would have 211 amino acids and a unmodified molecular weight of 23,323. The major homology of the protein encoded by this ORF and HAd5 E1A is in the residues corresponding to CR3 (shown in FIG. 2). The homology of amino acid sequences on both sides of the putative intron strengthens the assignment of probable splice donor and acceptor sites. The CR3 has been shown to be of prime importance in the transactivation activity of HAd5 E1A gene products. As seen in FIG. 2A the homology of this sequence in the BAV3 protein to the corresponding region of the 289R E1A protein of HAd5 includes complete conservation of the CysX$_2$CysX$_{13}$CysX$_2$Cys sequence motif (SEQ ID NO: 30) which defines the metal binding site of this protein (Berg, 1986 *Science* 232:485–487) as well as conservation of a number of amino acids within this region and within the promoter binding region as defined by Lillie and Green 1989 *Nature* 338:39–44).

The only other region of significant homology between the BAV3 E1A protein and that of HAd5 was a stretch of amino acids known to be important in binding of the cellular Rb protein to the HAd5 E1A protein (Dyson et al, 1990 *J. Virol.* 64:1353–1356). As shown in FIG. 2B, this sequence, which is located between amino acids 120 and 132 in the CR2 region of HAd5 E1A, is found near the amino (N-) terminus of the BAV3 protein between amino acids 26 and 37.

An open reading frame from the ATG at nt 1476 to the termination signal at 1947 defines a protein of 157 amino acids with two regions of major homology to the HAd5 E1B 19k protein. As shown in FIG. 3 both the BAV3 and the HAd5 proteins have a centrally located hydrophobic amino acid sequence. The sequence in BAV3, with substitutions of valine for alanine and leucine for valine, should result in a somewhat more hydrophobic pocket than the corresponding HAd5 region. The other portion of HAd5 19k that may be conserved in the BAV3 protein is the serine rich sequence found near the N-terminus (residues 20 to 26) in HAd5 19k and near the C-terminus (residues 136 to 142) in the BAV3 protein (also shown in FIG. 3).

On ORF beginning at the ATG at nt 1850 and terminating at nt 3110 overlaps the preceding BAV3 protein reading frame and thus has the same relationship to it as does the HAd5 E1B 56k protein to E1B 19k protein. As shown in FIG. 4 this BAV3 protein of 420R and the corresponding HAd5 E1B 56k protein of 496R show considerable sequence homology over their C-terminal 346 residues. The N-terminal regions of these proteins (not depicted in the figure) show no significant homology and differ in overall length.

Following the E1B ORFs, the open reading frame beginning at nt 3200 and ending at the translation terminator TAA at nt 3575 defines a protein of 125R with an unmodified molecular weight of 13,706. As seen in FIG. 5 this protein shares some homology with the structural protein IX of HAd5 particularly in N-terminal sequences.

Possible Transcription Control Regions in BAV3 E1

The inverted terminal repeats (ITR) at the ends of the BAV3 genome have been shown to extend to 195 nt (Shinagawa et al, 1987 *Gene* 55:85–93). The GC-rich 3' portion of the ITR contains a number of consensus binding sites for the transcription stimulating protein SP1 (Dynan and Tijan (1983) *Cell* 35:79–87) and possible consensus sites for the adenovirus transcription factor (ATF) (Lee et al. (1987) *Nature* 325:368–372) occur at nts 60 and 220. While there are no exact consensus sites for the factors EF-1A (Bruder and Healing (1989) *Mol. Cell Biol.* 9:5143–5153) or E2F (Kovesdi et al, 1987 *PNAS, USA* 84:2180–2184) upstream of the ATG at nt 606, there are numerous degenerate sequences which may define the enhancer region comparable to that seen in HAd5 (Hearing and Shenk, 1986 *Cell* 45:229–236).

The proposed BAV3 E1A coding sequence terminates at a TGA residue at nt 1346 which is located within a 35 base pair sequence which is immediately directly repeated (see FIG. 1). Two repeats of this sequence were detected in three independently derived clones for a plaque purified stock of BAV3. The number of direct repeats can vary in any BAV3 population though plaque purification allows for isolation of a relatively homogeneous population of viruses. That direct repeats in the sequences can function as promoter or enhancer elements for E1B transcription is being tested.

There are no strong polyA addition consensus sites between the E1A and the E1B coding sequences and in fact no AATAA sequence is found until after the protein IX coding sequences following E1B. The TATAAA sequence beginning at nt 1453 could function as the proximal promoter for E1B but it is located closer to the ATG at 1476 than is considered usual (McKnight et al, 1982 *Science* 217:316–322). The TATA sequence located further upstream immediately before the proposed E1A intron sequence also seems inappropriately positioned to serve as a transcription box for the E1B proteins. There are clearly some unique features in this region of the BAV3 genome.

The transcriptional control elements for the protein IX transcription unit are conventional and well defined. Almost immediately following the open reading frame for the larger E1B protein there is, at nt 3117, a SP1 binding sequence. This is followed at 3135 by a TATAAAT sequence which could promote a transcript for the protein IX open reading frame beginning at the ATG at 3200 and ending with the TAA at 3575. One polyA addition sequence begins within the translation termination codon and four other AATAA sequences are located at nts 3612, 3664, 3796 and 3932.

In keeping with the general organization of the E1A region of other adenoviruses, the BAV3 E1A region contains an intron sequence with translation termination codons in all three reading frames and which is therefore probably deleted by splicing from all E1A mRNA transcripts. The largest possible protein produced from the BAV3 E1A region will have 211 amino acid residues and is the equivalent of the 289 amino acid protein translated from the 13 s mRNA of HAd5. Two striking features in a comparison of these proteins are the high degree of homology in a region corresponding to CR3 and the absence in BAV3 of most of amino acids corresponding to the second exon of HAd5. In fact the only amino acids encoded in the second exon of BAV3 are, those which are considered to constitute part of CR3. A great deal of work carried out with HAd5 has identified the importance of the CR3 sequences in transactivation of other HAd5 genes. While a detailed analysis of the corresponding BAV3 region and its possible role in transactivation of BAV3 genes needs to be carried out, it is none-the-less interesting to note a couple of possibly pertinent features. The HAd5 CR3 region has been operationally subdivided into three regions (Lillie et al, 1989 *Nature* 338:39–44; see FIG. 8); an N-terminal region from 139 to 153 which has four acidic residues and is thought to be important in transcription activation, a central, metal-binding, region defined by the Cys-$X_2$-Cys-$X_{13}$-Cys$X_2$-Cys sequence (SEQ ID NO: 30) which is essential for both promoter binding and activation, and a C-terminal region (residues 175–189) which is essential for promoter binding. Since, in most instances, E1A protein is thought not to interact directly with DNA (Ferguson et al 1985), the promoter binding regions may be involved in forming associations with proteins which then allow association with DNA. In FIG. 2*a* the BAV3 E1A protein contains the central, metal binding domain and has considerable homology in the carboxy portion of this region. The BAV3 E1A protein also shows identity of sequence with HAd5 in the carboxy 6 amino acids of the promoter binding domain. These features may allow the BAV3 E1A protein to interact with the same transcription activating factors required for HAd5 E1A function. In contrast, except for a Glu-Glu pair there is little homology between the bovine and human viruses in the activation domain. The fact that this domain can be functionally substituted by a heterologous acidic activation sequence (Lillie et al, 1989 supra) suggests that protein specificity is not required in this region and this may allow the BAV3 E1A protein to function in the activation of BAV3 genes. The BAV3 E1A activation region contains six acidic residues in the 18 residues amino to the metal binding domain.

The other interesting feature of BAV3 E1A, which is undoubtedly relevant to the oncogenic potential of this virus, is the presence of the sequence Asp27-Leu-Glu-Cys-His-Glu which conforms to, a core sequence known to be important in the binding of cellular Rb and related proteins by the transforming proteins of a number of DNA tumour viruses (Dyson et al, 1990 supra). From deletion mutant analysis there is a clear association between the potential of HAd5 E1A proteins to bind Rb and the ability of the protein to induce morphological transformation in appropriate cells (see references in Dyson et al, 1990 supra). The BAV3 E1A protein is distinct from its HAd5 counterpart in the relative position of this Rb binding sequence which is in the CR2 of HAd5 E1A and near the N-terminus of the BAV3 E1A protein.

Through the use of alternative splice sites HAd5 E1A transcripts can give rise to at least 5 distinct mRNA species (Berk et al, 1978 *Cell* 14:695–711; Stephens et al, 1987 *EMBO Journal* 6:2027–2035). Whether BAV3, like HAd5, can generate a number of different mRNA species through the use of alternative splice sites in the E1A transcripts remains to be determined. For example a potential splice donor site which could delete the sequence equivalent to the unique sequence of HAd5 is present immediately after nt 1080 but it is not known if this site is actually used.

HAd5 E1B encodes two proteins (19 k and 56 k) either of which can cooperate with E1A, by pathways which are additive and therefore presumably independent (McLorie et al, 1991 *J. Gen. Virol.* 72:1467–1471), to produce morphological transformation of cells in culture (see for example: Branton et al, 1985 supra; Graham, 1984 supra). The significance of the conservation of the hydrophobic stretch of amino acids in the central portion of the shorter E1B proteins of HAd5 and BAV3 is not clear as yet. A second short region of homology Gln-Ser-Ser-X-Ser-Thr-Ser (SEQ ID NO: 31) at residue 136 near the C-terminus of the BAV3 protein is located near the N-terminus at residue 20 in the HAd5 19 k protein. The major difference in both length and sequence of the larger (420R) E1B protein of BAV3 from the corresponding HAd5 protein (496R) is confined to the N-terminus of these proteins. The two proteins show considerable evolutionary homology in the 345 amino acids that extend to their C-termini. A similar degree of homology extends into the N-terminal halves of protein IX of BAV3 and HAd5. Taken together these analyses suggest that while BAV3 and the human adenoviruses have diverged by simple point mutational events in some regions, more dramatic genetic events such as deletion and recombination may have been operating in other regions particularly those defining the junction between E1A and E1B.

Example 3

Cloning and Sequencing of the BAV3 E3 and Fibre Genes

The general organization of adenovirus genomes seems to be relatively well conserved so it was possible to predict, from the locations of a number of HAd E3 regions, that BAV E3 should lie between map units (m.u.) 77 to 86. To prepare DNA for cloning and sequencing, BAV3 (strain WBR-1) was grown in Madin-Darby bovine kidney (MDBK) cells, virions were purified and DNA was extracted (Graham, F. L.

& Prevec, L. (1991) Methods in Molecular Biology, vol. 7, Gene Transfer and Expression Protocols, pp. 109–146. Edited by E. J. Murray, Clifton, N.J.; Humana Press.). Previously published restriction maps for EcoRI and BamHI (Kurokawa et al., 1978) were confirmed (FIG. 6). The BamHI D and EcoRI F fragments of BAV3 DNA were isolated and inserted into pUC18 and pUC19 vectors, and nested sets of deletions were made using exonuclease III and S1 nuclease (Henikoff, S. (1984) *Gene*, 28:351–359). The resulting clones were sequenced by the dideoxynucleotide chain termination technique (Sanger, F., Nicklen, S. & Coulson, A. R. (1977) *Proceedings of the National Academy of Sciences, U.S.A.*, 74:5463–5467). The nucleotide sequence from positions 1 to 287 was obtained from the right end of the BamHI B fragment (FIG. 6). The sequence of the regions spanning (i) the BamHI site at nucleotide 3306 and the EcoRI site at nucleotide 3406, and (ii) the EcoRI site at nucleotide 4801 and the nucleotide 5100 was obtained from a plasmid containing the XbaI C fragment (m.u. 83 to 100; not shown) using primers hybriding to BAV3 sequences. Analysis of the sequence was performed with the aid of the PC/GENE sequence analysis package developed by Amos Bairoch, Department of Medical Biochemistry, University of Geneva, Switzerland.

The 5100 nucleotide sequence which extends between 77 and 92 m.u. of the BAV3 genome is shown in FIG. 7. The upper strand contains 14 open reading frames (ORFs) which could encode polypeptides of 60 amino acid residues or more (FIGS. 6 and 7). The lower strand contains no ORF encoding a protein of longer than 50 amino acids after an initiation codon. The predicted amino acid sequence for each ORF on the upper strand was analyzed for homology with predicted amino acid sequences from several sequenced Ads: HAd2 (Hérissé, J., Courtois, G. & Galibert, F. (1980) *Nucleic Acids Research*, 8:2173–2192; Hérissé, J., Courtois, G. & Galibert, F. (1981) *Nucleic Acids Research*, 9:1229–1249), –3(Signas, C., Akusjarvi, G. & Pettersson, U. (1985) *Journal of Virology*, 15:672–678.), –5(Cladaras, C. & Wold, W. S. M. (1985) *Virology*, 140:28–43), –7 (Hong, J. S., Mullis, K. G. & Engler, J. A. (1988) *Virology*, 167:545–553) and –35 (Flomenberg, P. R., Chen, M. & Horwitz, M. S. (1988) *Journal of Virology*, 62:4431–4437), and murine Ad1 (MAd1) (Raviprakash, K. S., Grunhaus, A., E1 Kholy, M. A. & Horwitz, M. S. (1989) *Journal of Virology*, 63:5455–5458) and canine Ad1 (CAd1) (Dragulev, B. P., Sira, S., Abouhaidar, M. G. & Campbell, J. B. (1991) *Virology*, 183:298–305). Three of the BAV3 ORFs exhibited homology with characterized HAd proteins pVIII, fibre and the 14.7K E3 protein. The amino acid sequence predicted from BAV3 ORF 1 shows overall identity of approximately 55% when compared to the C-terminal 75% of HAd2 pVIII (Cladaras & Wold, 1985, supra) (FIG. 8a), indicating that ORF 1 encodes the right end of BAd3 pVIII. Near the C-terminal end of BAd3 pVIII there is a 67 amino acid stretch (residues 59 to 125; FIG. 8a) which has 75% identity with HAd2 pVIII. This region has previously been shown to be highly conserved among different Ads (Cladaras & Wold, 1985, supra; Signas, C., Akusjarvi, G. & Pettersson, U. (1986) *Gene*, 50:173–184,; Raviprakash et al., 1989, supra; Dragulev et al., 1991, supra).

The fibre protein is present on the surface of the virion as long projections from each vertex of the icosahedral capsid and is involved in a number of Ad functions including attachment of the virus to the cell surface during infection, assembly of virions and antigenicity (Philipson, L. (1983) *Current Topics in Microbiology and Immunology*, 109:1–52). On the basis of the primary structure of HAd2 fibre protein, it has been proposed that the shaft region (between amino acid residues 40 and 400) is composed of a number of repeating structural motifs containing about 15 hydrophobic residues organized in two short β-sheets and two β-bends (Green, N. M., Wrigley, N. G., Russell, W. C., Martin, S. R. & McLachlan, A. D. (1983) *EMBO Journal*, 2:1357–1365). The amino acid sequences at the N terminus of the BAV3 ORF 6-encoded protein share about 60% identity with the HAd2 fibre protein tail, but there is little or no similarity in the knob region, and about 45% identity overall (FIG. 8c). The BAd3 fibre gene would encode a protein of 976 residues if no splicing occurs, i.e. 394 amino acid residues longer than the HAd2 fibre protein. The number of repeating motifs in the shaft region of the fibre protein from different Ads varies between 28 and 23 (Signas et al., 1985, supra; Chroboczek, J. & Jacrot, B. (1987) *Virology*, 161:549–554; Hong et al., 1988, supra; Raviprakash et al., 1989, supra; Dragulev et al., 1991, supra). The BAV3 fibre protein can be organized into 52 such repeats in this region (not shown), which would account for most of the difference in size compared to those of HAd2, HAd3, HAD5, HAd7, CAd1 and MAd1 (Signas et al., 1985,supra; Hérissé et al., 1980,supra; Hérissé & Galibert, 1981, supra; Hong et al., 1988,supra; Raviprakash et al., 1989, supra; Dragulev et al., 1991, supra).

HAd2 and HAd5 E3 lies between the pVIII and the fibre genes an encodes at least 10 polypeptides (Cladaras & Wold, 1985,supra). The promoter for E3 of these two serotypes lies within the sequences encoding pVIII, about 320 bp 5' of the termination codon. No consensus TATA box is found in the corresponding region of the BAV3 sequences. A non-canonical polyadenylation signal (ATAAA) for E3 transcripts is located at position 1723, between the end of the putative E3 region and the beginning of ORF 6, encoding the fibre protein, and two consensus signals are located within ORF 6 at positions 2575 and 3565. The polyadenylation signal for the fibre protein is located at nucleotide 4877. Six ORFs were identified in the BAV3 genone between the pVIII and the fibre genes, but only four (ORFs 2, 3, 4 and 5) have the potential to encode polypeptides of at least 50 amino acids after an initiation codon (FIG. 7). The amino acid sequence predicted to be encoded by ORF 2 is 307 residues long and contains eight potential N-glycosylation sites (FIG. 7) as well as a hydrophobic sequence which may be a potential transmembrane domain (PLLFAFVLCTGCAVLLTAFGPSILSGT) (SEQ ID NO: 32) between residues 262 and 289. This domain may be a part of the protein homologous to the HAd2 and HAd5 19K E3 glycoprotein (Cladaras & Wold, 1985, supra), and the proposed CAd1 22.2K protein (Dragulev et al., 1991, supra), but ORF 2 does not show appreciable homology with these proteins. The ORF 4 shows approximately 44% identity with the 14.7K E3 protein of HAd5 (FIGS. 6 and 8b), which has been shown to prevent lysis of virus-infected mouse cells by tumour necrosis factor (Gooding, L. R., Elmore, L. W., Tollefson, A. E., Brody, H. A. & Wold, W. S. M. (1988) *Cell*, 53:341–346; Wold, W. S. M. & Gooding, L. R. (1989) *Molecular Biology and Medicine*, 6:433–452). Analysis of the 14.7K protein sequence from HAd2, –3, –5 and –7 has revealed a highly conserved domain, which in HAd5 lies between amino acid residues 41 and 56 (Horton, T. M., Tollefson, A. E., Wold, W. S. M. & Gooding, L. R. (1990) *Journal of Virology*, 64:1250–1255). The corresponding region in the BAV3 ORF 4-encoded protein, between amino acids 70 and 85, contains 11 amino acids identical to those of the HAd5 14.7K protein conserved domain (FIG. 8b).

The BAV3 E3 region appears to be approximately 1.5 kbp long, about half the size of those of HAd2 and –5 (Cladaras & Wold, 1985, supra), and novel splicing events in BAV3 E3 would be required to generate more homologues to the HAd3 E3 proteins. A similarly short E3 region has been reported for MAd1 (RAviprakash et al., 1989, supra) and CAd1 (Dragulev et al., 1991,supra).

Example 4

Construction of BAV3-luciferase Recombinants

Adenovirus-based mammalian cell expression vectors have gained tremendous importance in the last few years as a vehicle for recombinant vaccine delivery, and also in gene therapy. BAV3-based expression vectors have a greater potential for developing novel recombinant vaccines for veterinary use. To show that BAV3 E3 gene products are not essential for virus growth in cultured cells and this locus could be used to insert foreign DNA sequences, a 1.7 kb fragment containing the firefly luciferase gene was introduced in the 696 bp deletion of the E3 region of the BAV3 genome in the E3 parallel orientation to generate a BAV3 recombinant.

The rationale of using the luciferase gene is that it acted as a highly sensitive reporter gene when introduced in the E3 region Qf the HAd5 genome to generate HAd5-Luc recombinants (Mittal et al (1993) *Virus Res.* 28:67–90).

Figure 9:
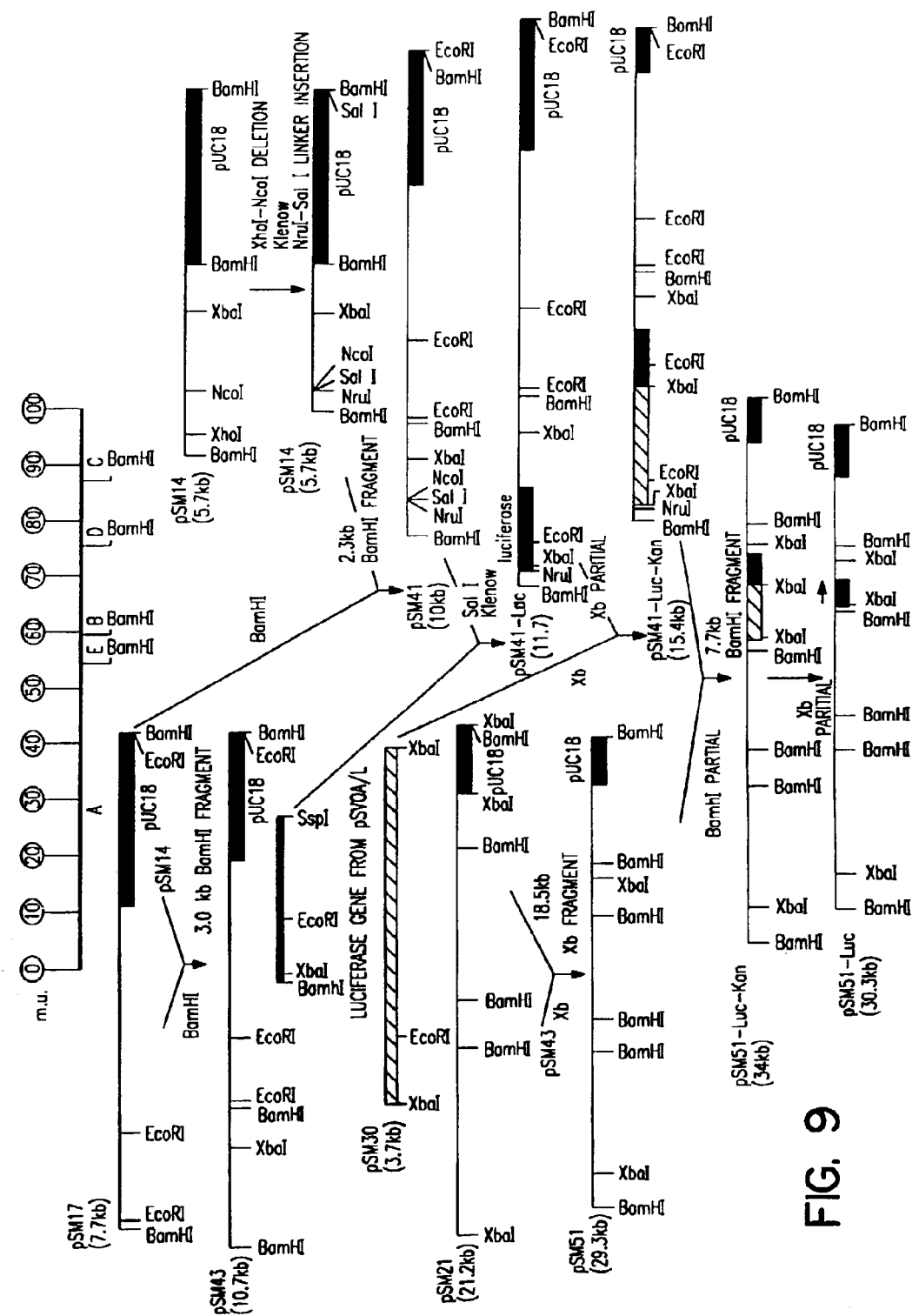
FIG. 9. Construction of BAV3 E3 transfer vector containing the firefly luciferase gene. The 3.0 kb BamHI 'D' fragment of the BAV3 genome which falls between m.u. 77.8 and 86.4, contains almost the entire E3 region (Mittal et al (1992) *J. Gen. Virol.* 73:3295–3000). This 3.0 kb fragment was isolated by digesting BAV3 DNA with BamHI and cloned into pUC18 at the BamHI site to obtain pSM14. Similarly, the 4.8 kb BamHI 'C' fragment of BAV3 DNA which extends between m.u. 86.4 and 100 was isolated and inserted into pUC18 to produce pSM17. To delete a 696 bp XhoI-NcoI fragment, pSM14 was cleaved with XhoI and NcoI, the larger fragment was purified and the ends were made blunt with Klenow fragment of DNA polymerase I and a NruI-SalI linker was inserted to generate pSM14 del2. A 2.3 kb BamHI fragment containing BAV3 sequences, an E3 deletion and NruI and SalI cloning sites, was inserted into pSM17 at the BamHI site to obtain pSM41, however, this step was not required for construction of a BAV3 E3 transfer vector. A 1716 bp fragment containing the firefly luciferase gene (de Wet et al (1987) *Mol. Cell. Biol.* 7:725–737) was isolated by digesting pSVOA/L (provided by D. R. Helinski, University of California at San Diego, Calif.) with BsmI and SspI as described (Mittal et al (1993) *Virus Res.* 28:67–90), and the ends were made blunt with Klenow. The luciferase gene was inserted into pSM41 at the SalI site by blunt end ligation. The resultant plasmid was named pSM41-Luc which contained the luciferase gene in the same orientation as the E3 transcription unit. The plasmid pKN30 was digested with XbaI and inserted into pSM41-Luc (partially cleaved with XbaI) at a XbaI site present within the luciferase gene to obtain pSM41-Luc-Kan. The plasmid pSM14 was digested with BamHI and a 3.0 kb fragment was isolated and inserted into pSM17 at the BamHI site to generate pSM43. The 18.5 kb XbaI 'A' fragment of the BAV3 genome which falls between m.u. 31.5 and 84.3 was cloned into pUC18 at the XbaI site to result pSM21. A 18.5 kb XbaI fragment was purified from pSM21 after cleavage with XbaI and inserted into pSM43 at the XbaI site and the resultant plasmid was named pSM51. A 7.7 kb BamHI fragment containing the luciferase gene and kan$^r$ gene was isolated after digesting pSM41-Luc-Kan with BamHI and ligated to pSM51, partially digested with BamHI, to isolate pSM51-Luc-Kan in the presence of ampicillin and kanamycin. Finally the kan$^r$ gene was deleted from pSM51-Luc-Kan by partial cleavage with XbaI and religation to obtain pSM51-Luc.

To facilitate the insertion of the firefly luciferase gene into the E3 region of the BAV3 genome, a BAV3 E3 transfer vector containing the luciferase gene was constructed (FIG. 9). The BAV3 E3 region falls approximately between m.u. 77 and 82. In our first series of vectors we replaced a 696 bp XhoI-NcoI E3 deletion (between m.u. 78.8 and 80.8) with a NruI-SalI cloning sites for insertion of foreign genes to obtain pSM14del2. A 1716 bp BsmI-SspI fragment containing the luciferase gene was isolated and first inserted into an intermediate plasmid, pSM41, in the E3 locus at the SalI site by blunt end ligation to generate pSM41-Luc. The luciferase gene without any exogenous regulatory sequences, was inserted into the E3 locus in the same orientation as the E3 transcription unit. The kan$^r$ gene was inserted into pSM41-Luc at the XbaI site present within the luciferase gene to generate an amp$^r$/kan$^r$ plasmid, pSM41-Luc-Kan. A 7.7 kb fragment containing the BAV3 sequences along with the luciferase gene and the kan$^r$ gene was obtained from pSM41-Luc-Kan by digestion with BamHI and inserted into an amp$^r$ plasmid, pSM51 partially digested with BamHI to replace a 3.0 kb BamHI fragment (lies between m.u. 77.8 and 86.4) to generate a doubly resistant (kan$^r$ & amp$^r$) plasmid, pSM51-Luc-Kan. The kan$^r$ gene was deleted from pSM51-Luc-Kan by partial cleavage with XbaI to generate pSM51-Luc containing the luciferase gene in the E3-parallel orientation.

Figure 10:
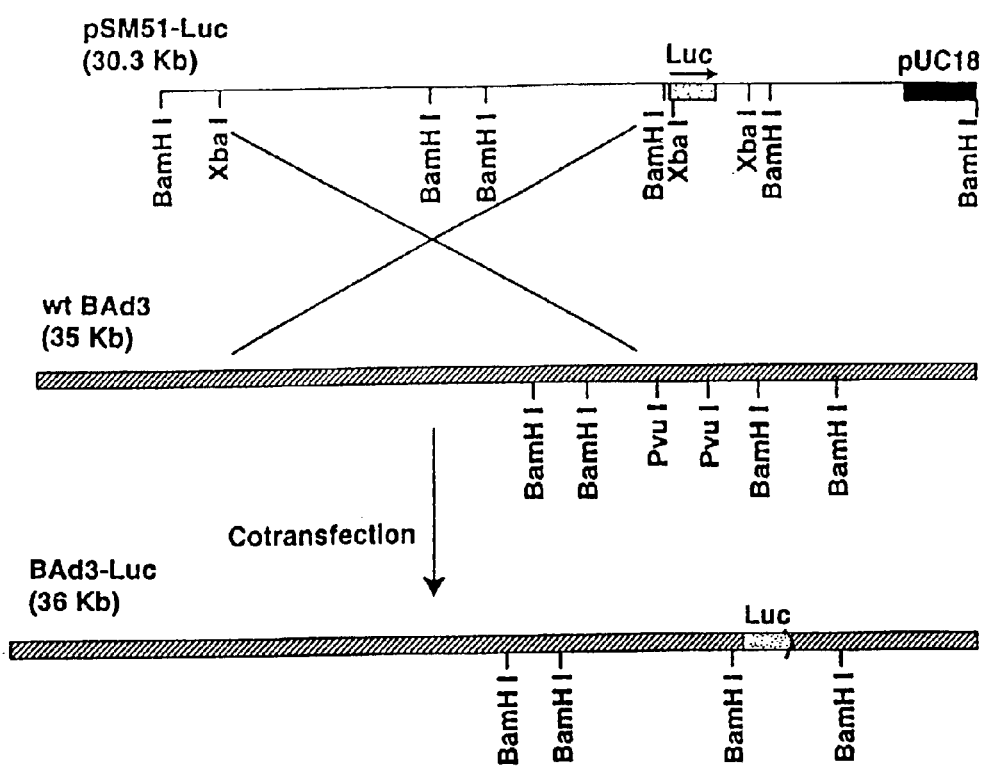
FIG. 10. Generation of BAV3 recombinants containing the firefly luciferase in the E3 region. The plasmid pSM51-Luc contains the BAV3 genome between m.u. 77.8–84.3 and 31.5–100, a 696 bp deletion in E3 and the luciferase gene in E3 in the E3 parallel orientation. The BAV3 genome digested with PvuI and uncut pSM51-Luc were used for cotransfection of MDBK cells transformed with a plasmid containing BAV3 E1 sequences to rescue the luciferase gene in E3 of the BAV3 genome by in vivo recombination. The resulting BAV3-luciferase recombinants (BAV3-Luc) isolated from two independent experiments were named BAV3-Luc (3.1) and BAV3-Luc (3.2). The BamHI restriction map of the BAV3-Luc genome is shown. The position and orientation of the firefly luciferase gene is shown as a hatched arrow.

MDBK cells transformed with a plasmid containing the BAV3 E1 sequences was cotransfected with the wt BAV3 DNA digested with PvuI, which make two cuts within the BAV3 genome at m.u 65.7 and 71.1, and the plasmid, pSM51-Luc to rescue the luciferase gene in E3 of the BAV3 genome by in vivo recombination (FIG. 10). The digestion of the wt BAV3 DNA with PvuI was helpful in minimizing the generation of the wt virus plaques following cotransfection. The left end of the wt BAV3 genome represented by PvuI 'A' fragment falls between m.u. 0 and 65.7, and pSM51-Luc which extends between m.u. 31.5 and 100 (except for E3 deletion replaced with the luciferase gene) have sufficient overlapping BAV3 DNA sequences to generate recombinant viruses.

Two virus plaques were obtained in two independent cotransfection experiments which were grown in MDBK cells. The viral DNA from both plaques was extracted and analyzed by agarose gel electrophoresis after digesting either with BamHI, EcoRI or XbaI to identify the presence and orientation of the luciferase gene in the viral genome (data not shown). In the genomes of both recombinants, the luciferase gene was present in the E3 region in the E3 parallel orientation. The BAV3-luciferase recombinants were plaque purified and named BAV3-Luc (3.1) and BAV3-Luc (3.2) to represent plaques obtained from two independent experiments. Since both recombinant virus isolates were identical they will be referred to as BAV3-Luc. The presence of the luciferase gene in BAV3-Luc isolates are further confirmed by Southern blot analyses and luciferase assays using extracts from recombinant virus-infected cells.

Characterization of BAV3-recombinants

Southern blot analyses of the wt BAV3 and recombinants genomic DNA digested either with BamHI, EcoRI or XbaI, were carried out to confirm the presence and orientation of the luciferase gene in the E3 locus and the deletion of the 696 bp XhoI-NcoI fragment from E3 of the BAV3-Luc genome (FIG. 11). When the blot was probed with a 696 XhoI-NcoI fragment of E3 of the BAV3 genome (panel A, lanes 4 to 9) no hybridization signal was detected with the DNA fragments from the recombinant viruses, however, the expected bands (3.0 kb BamHI, 8.1 kb EcoRI, and 18.5 kb XbaI) of the wt BAV3 DNA fragments (panel A, lanes 10 to 12) showed hybridization, confirming that the 696 bp XhoI-NcoI fragment of the E3 region was indeed deleted in the BAV3-Luc genomic DNA. In panel B, when an identical blot was probed with the luciferase gene, there were strong hybridization signals with the DNA fragments from the recombinant viruses (4.0 kb BamHI (lane 4 & 7), 6.0 kb & 3.2 kb EcoRI (lanes 5 & 8), 16.7 kb & 2.9 kb XbaI (lanes 6 & 9)). These results confirmed that the BAV3-Luc contains the luciferase gene in the E3 parallel orientation with a 696 bp XhoI-NcoI E3 deletion.

Figure 12:
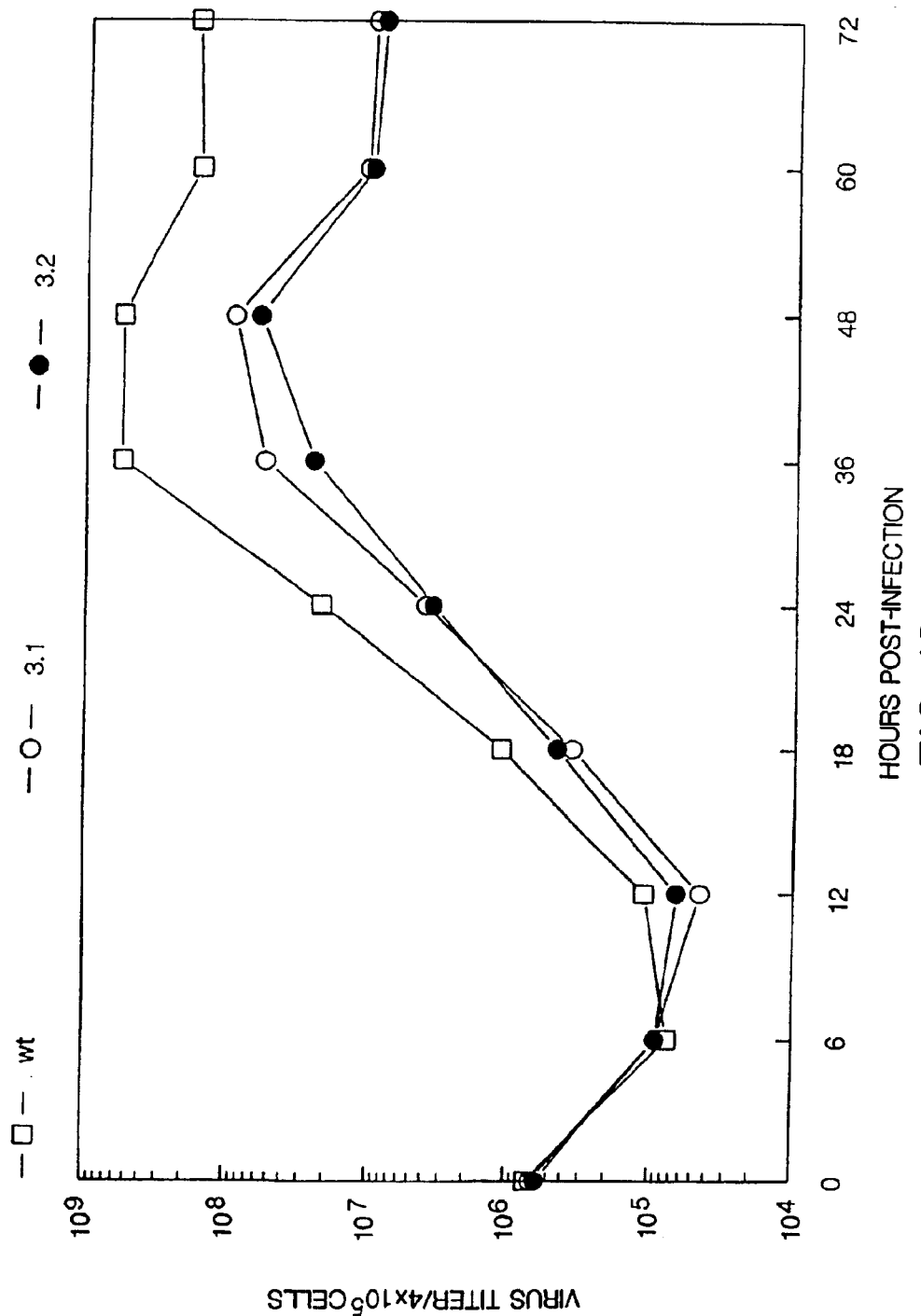
FIG. 12. Single step growth curve for wt BAV3 and BAV3-Luc. Confluent monolayers of MDBK cells in 25 mm multi-well culture plates were inoculated with the wt BAV3, BAV3-Luc (3.1) or BAV3-Luc (3.2) at a m.o.i. of 10 p.f.u. per cell. The virus was allowed to adsorb for 1 h at 37° C., cell monolayers were washed 3 times with PBS$^{++}$ (0.137 M NaCl, 2.7 mM KCl, 8 mM Na$_2$HPO$_4$, 1.5 mM KH$_2$PO$_4$, containing 0.01% CaCl$_2$·2H$_2$O & 0.01% MgCl$_2$·6H$_2$O) and incubated at 37° C. in 1 ml maintenance medium containing 2% horse serum. At various times post-infection, cells were harvested along with the supernatant, frozen and thawed three times and titrated on MDBK cells by plaque assay. Results are the means of duplicate samples.

The growth characteristics of the recombinant viruses was compared with the wt BAV3 in a single step growth curve (FIG. 12). Virus titers in MDBK cells-infected with the wt BAV3 started increasing at 12 h post-infection reaching a maximum at 36–48 h post-infection and then declined thereafter. Virus titers of the recombinant viruses also started increasing at 12 h postinfection reaching a maximum at 48 h post-infection and then declined, however, the titers of recombinant viruses remained approximately one log lower than the wt virus. The plaque size of the recombinant viruses were also comparatively smaller than the wt virus (data not shown).

Kinetics of Luciferase Expression by BAV3-Luc

Figure 13:
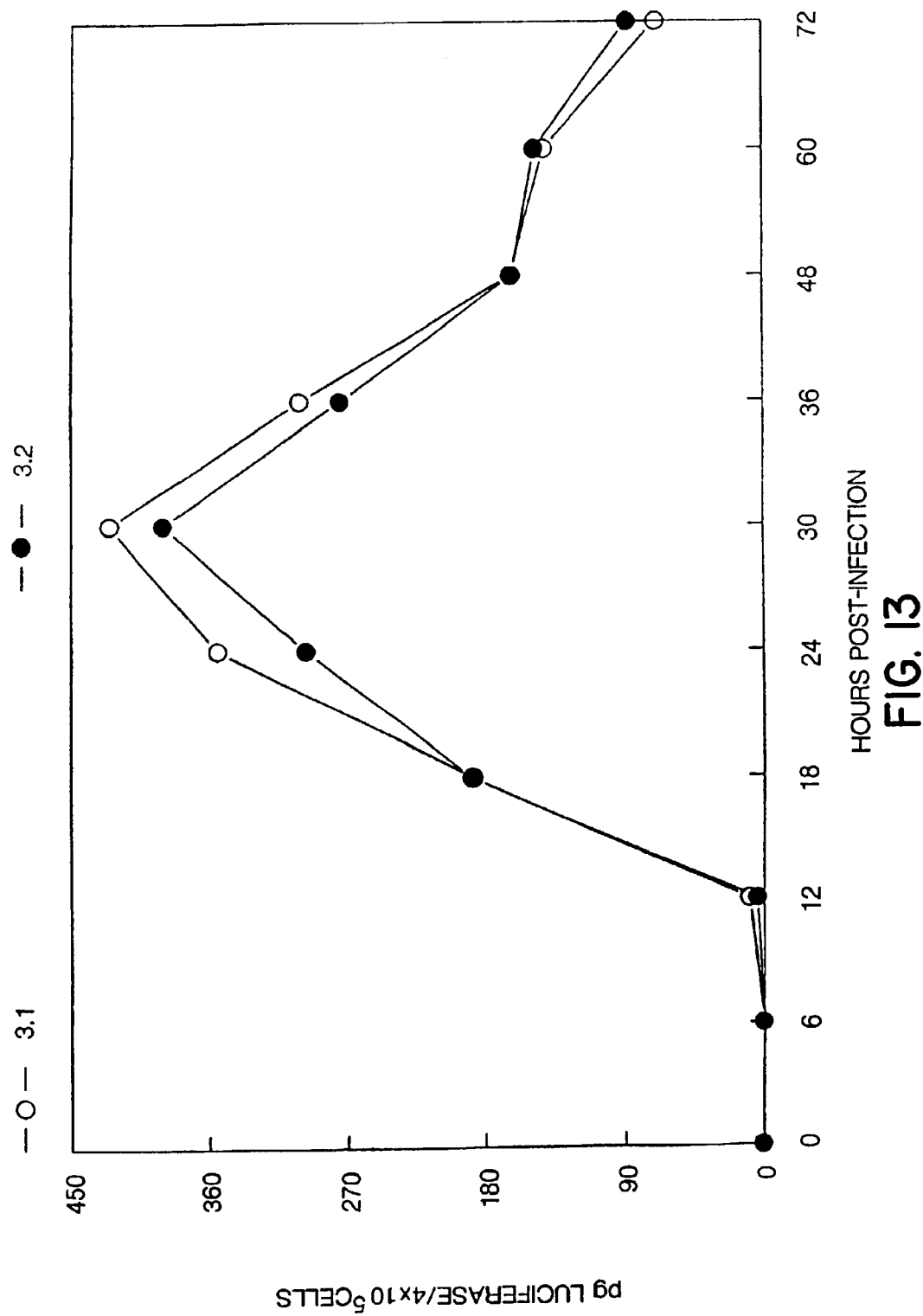
FIG. 13. Kinetics of luciferase expression in MDBK cells-infected with BAV3-Luc. Confluent MDBK cell monolayers in 25 mm multi-well culture plates were infected with BAV3-Luc (3.1) or BAV3-Luc (3.2) at a m.o.i. of 50 p.f.u. per cell. At indicated time points post-infection, virus-infected cells were harvested and assayed in duplicate for luciferase activity.
Figure 14A:
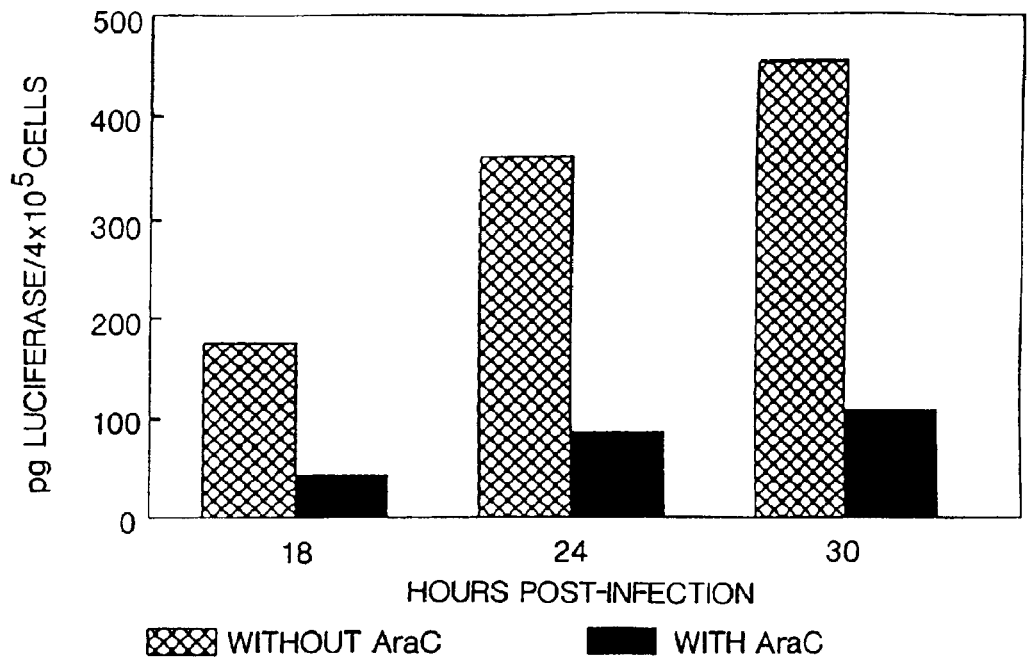
FIGS. 14A–14B. Luciferase expression in the presence of 1-β-D-arabinofluranosyl cytosine (AraC) in MDBK cells-infected with BAV3-Luc. Confluent MDBK cell monolayers in 25 mm multi-well culture plates were infected with A) BAV3-Luc (3.1) or B) BAV3-Luc (3.2) at a m.o.i. of 50 p.f.u. per cell and incubated in the absence or presence of 50 µg AraC per ml of maintenance medium. At indicated time points post-infection, virus-infected cells were harvested and assayed in duplicate for luciferase activity.
Figure 14B:
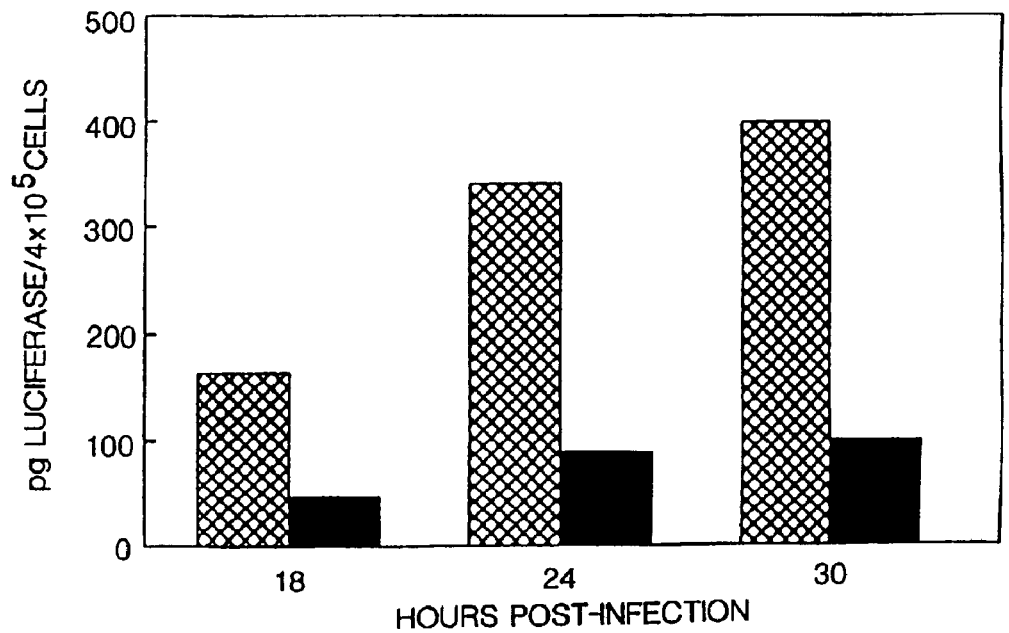

Luciferase activity in BAV3-Luc-infected MDBK cells was monitored at different times post-infection by luciferase assays (FIG. 13). A low level of luciferase activity was first observed at 12 h post-infection reaching a peak at 30 h post-infection and then dropped subsequently. At 30 h post-infection, approximately 425 pg luciferase was detected in $4 \times 10^5$ BAV3-Luc (3.1)—infected MDBK cells. In MDBK cells-infected with the wt BAV3, luciferase expression was not detected (data not shown). The kinetics of luciferase expression by BAV3-Luc (3.1) and BAV3-Luc (3.2) appears very much similar. The kinetics of luciferase expression also showed that the majority of enzyme expression in virus-infected cells seemed to occur late in infection. To determine luciferase expression in the absence of viral DNA replication, BAV3-Luc-infected MDBK cells were incubated in the presence of an inhibitor of DNA synthesis, 1-β-D—arabinofuranosyl cytosine (AraC) and luciferase activity was measured in virus-infected cell extracts at various times post-infection and compared to luciferase expression obtained in the absence of AraC (FIG. 14). When the recombinant virus-infected cells were incubated in the presence of AraC, luciferase expression at 18, 24 and 30 h post-infection was approximately 20–30% of the value obtained in the absence of AraC. These results indicated that the majority of luciferase expression in MDBK cells infected with BAV3-Luc took place after the onset of viral DNA synthesis. To confirm this MDBK cells-infected with the BAV3-Luc were grown in the absence or presence of AraC, harvested at 18 h, 24 h, and 30 h post-infection, viral DNA extracted and analyzed by dot bot analysis using pSM51-Luc (see FIG. 9) as a probe (data not shown). In the presence of AraC, viral DNA synthesis was severely reduced compared to viral DNA synthesis in the absence of AraC.

Western Blot Analysis of BAV3-Luc-Infected Cells

Figure 15A:
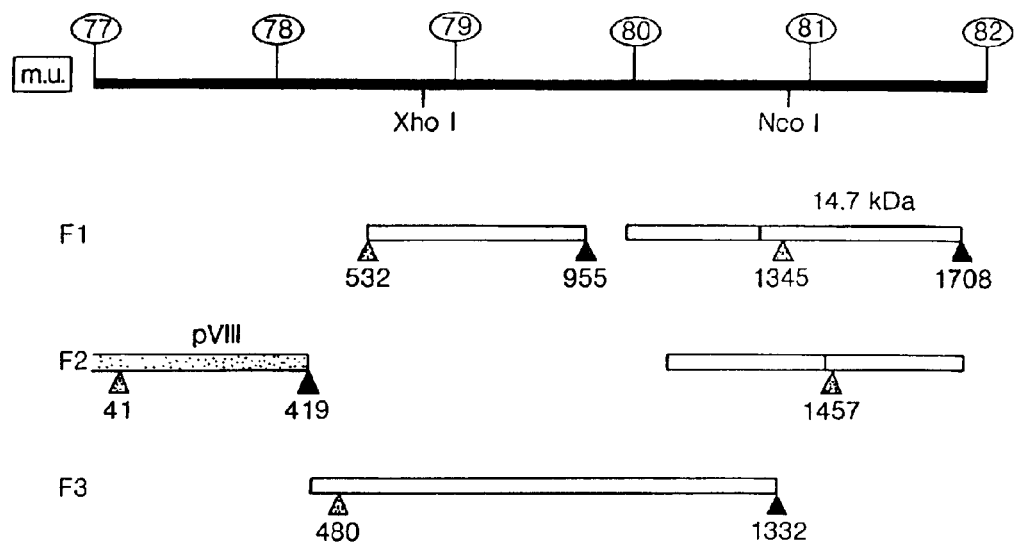
FIGS. 15A–15B. Transcription maps of the wt BAV3 and BAV3-Luc genomes in the E3 region. The genome of wt BAV3 between m.u. 77 and 82 is shown which represents the E3 region. The location of XhoI and NcoI sites which were used to make an E3 deletion are shown. (a) The three frames (F1, F2 and F3) representing the open reading frames (ORFs) in the upper strand of the wt BAV3 genome in the E3 region are represented by bars. The shaded portions indicate regions of similarities to pVIII and E3-14.7 kDa proteins of HAd5. The positions of the initiation and termination codons for ORFs likely to code for viral proteins are shown by open and closed triangles, respectively. (b) The predicted ORFs for the upper strand in E3 of the BAV3-Luc genome are shown after a 696 bp XhoI-NcoI E3 deletion replaced by the luciferase gene. The ORFs for pVIII and E3-14.7 kDa proteins are intact. The transcription map of the wt BAV3 E3 was adapted from the DNA sequence submitted to the GenBank database under accession number D16839.
Figure 15B:
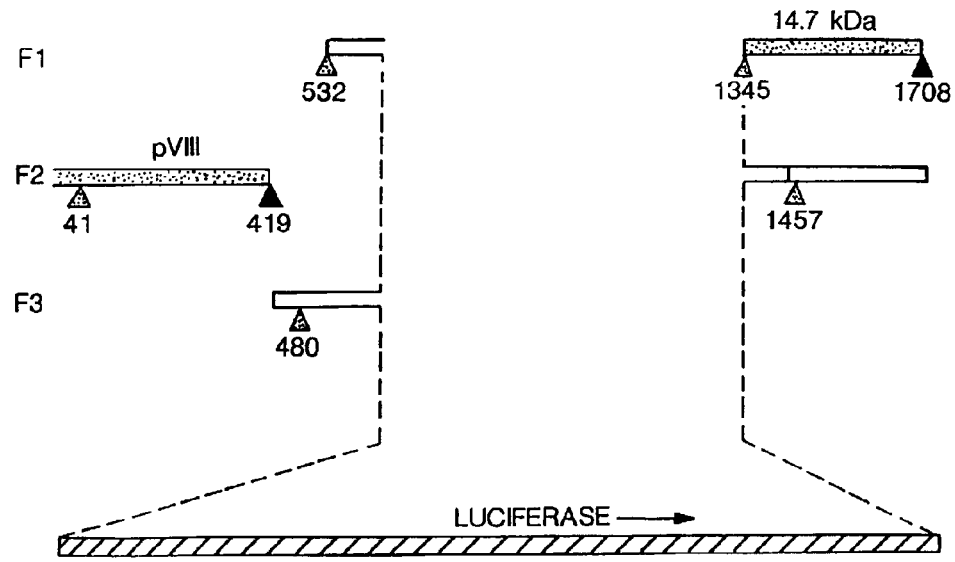

Luciferase was expressed as an active enzyme as determined by luciferase assays using extracts from MDBK cells-infected with-BAV3-Luc (see FIG. 13). The luciferase gene without any exogenous regulatory sequences was inserted into E3 of the BAV3 genome, therefore, there was a possibility of luciferase expression as a fusion protein with part of an E3 protein if the luciferase gene was in the same frame, Such as, F1 and F3 which represent open reading frames (ORFs) for E3 proteins (FIG. 15) or the fusion protein may arise due to recognition of an upstream initiation codon in the luciferase ORF. To explore this possibility we sequenced the DNA at the junction of the luciferase gene and the BAV3 sequences with the help of a plasmid, pSM51-Luc and a synthetic primer design to bind luciferase coding sequences near the initiation codon (data not shown).

The luciferase coding region fell in frame F2. The luciferase initiation codon was the first start codon in this frame, however, the ORF started at 84 nucleotides upstream of the luciferase start codon. To further confirm that luciferase protein is of the same molecular weight as purified firefly luciferase, unlabeled mock-infected, wt BAV3-infected or BAV3-Luc-infected MDBK cell extracts were reacted with an anti-luciferase antibody in a Western blot (FIG. 16). A 62 kDa polypeptide band was visible in the BAV3-Luc (lane 3 and 4)-infected cell extracts which were of the same molecular weight as pure firefly luciferase (lane 5). We are not sure whether a band of approximately 30 kDa which also reacted with the anti-luciferase antibody in lanes 3 and 4 represented a degraded luciferase protein.

The majority of luciferase expression is probably driven from the major late promoter (MLP) to provide expression paralleling viral late gene expression, moreover, the enzyme expression seen in the presence of AraC may be taking place from the E3 promoter. In HAd5 vectors, foreign genes without any exogenous regulatory sequences when inserted in E3 also displayed late kinetics and were inhibited by AraC. The BAV3 recombinant virus replicated relatively well in cultured cells but not as good as the wt BAV3. This is not surprising as infectious virus titers of a number of HAd5 recombinants were slightly lower than the wt HAd5 (Bett et al (1993) *J. Virol.* 67:5911–5921). This may be because of reduced expression of fiber protein in recombinant adenoviruses having inserts in the E3 region compared to the wt virus (Bett et al, supra and Mittal et al (1993) *Virus Res.* 28:67–90).

The E3 of BAV3 is approximately half the size of the E3 region of HAd2 or HAd5 and thus has the coding potential for only half the number of proteins compared to E3 of HAd2 or HAd5 (Cladaras et al (1985) *Virology* 140:28–43; Hérissé et al (1980) *Nuc. Acids Res.* 8:2173–2192; Herisse et al (1981) *Nuc. Acids Res.* 9:1229–1249 and Mittal et al (1993 *J. Gen. Virol.* 73:3295–3000). BAV3 E3 gene products have been shown to be not required for virus growth in tissue culture. However, presently it is known that BAV3 E3 gene products also evade immune surveillance in vivo like HAds E3 proteins. One of the BAV3 E3 open reading frames (ORFs) has been shown to have amino acid homology with the 14.7 kDa E3 protein of HAds (Mittal et al (1993) supra). The 14.7 kDa E3 protein of HAds prevents lysis of virus-infected mouse cells by tumour necrosis factor (Gooding et al (1988) *Cell* 53:341–346 and Horton et al (1990) *J. Virol.* 64:1250–1255). The study of pathogenesis and immune responses of a series of BAV3 E3 deletion mutants in cattle provides very useful information regarding the role of E3 gene products in modulating immune responses in their natural host.

The BAV3-based vector has a 0.7 kb E3 deletion which can hold an insert up to 2.5 kb in size. The BAV3 E3 deletion can extend probably up to 1.4 kb which in turn would also increase the insertion capacity of this system. The role of the MLP and the E3 promoter is examined to determine their ability to drive expression of a foreign gene inserted into E3 when a proper polyadenylation signal is provided. Exogenous promoters, such as, the simian virus 40 (SV40) promoter (Subramant et al (1983) *Anal. Biochem.* 135:1–15), the human cytomegalovirus immediate early promoter (Boshart et al (1985) *Cell* 43:215–222), and the human beta-actin promoter (Gunning et al (1987) *PNAS, USA* 84:4831–4835) are tested to evaluate their ability to facilitate expression of foreign genes when introduced into E3 of the BAV3 genome.

Recently HAd-based expression vectors are under close scrutiny for their potential use in human gene therapy (Ragot et al (1993) *Nature* 361:647–650; Rosenfeld et al (1991) *Science* 252:431–434; Rosenfeld et al (1992) *Cell* 68:141–155 and Stratford-Perricaudet et al (1990) *Hum. Gene. Ther.* 1:241–256). A preferable adenovirus vector for gene therapy would be one which maintains expression of the required gene for indefinite or for a long period in the target organ or tissue. It may be obtained if the recombinant virus vector genome is incorporate into the host genome or maintained its independent existence extrachromosomally without active virus replication. HAds replicate very well in human, being their natural host. HAds can be made defective in replication by deleting the E1 region, however, how such vectors would maintain the expression of the target gene in a required fashion is not very clear. Moreover, the presence of anti-HAds antibodies in almost every human being may create some problems with the HAd-based delivery system. The adenovirus genomes have a tendency to form circles in non-permissive cells. BAV-based vectors could provide a possible alternative to HAd-based vectors for human gene therapy. As BAV3 does not replicate in human, the recombinant BAV3 genomes may be maintained as independent circles in human cells providing expression of the essential protein for a long period of time.

The foreign gene insertion in animal adenoviruses is much more difficult than HAds because it is hard to develop a cell line which is also good for adenovirus DNA-mediated transfection. This may be one of the major reasons that the development of an animal adenovirus-based expression system has not been reported so far. It took us more than a year to isolate a cell line suitable for BAV3 DNA-mediated transfection. However, the rapid implementation of BAV-based expression vectors for the production of live virus recombinant vaccines for farm animals, is very promising. BAVs grow in the respiratory and gastrointestinal tracts of cattle, therefore, recombinant BAV-based vaccines have use to provide a protective mucosal immune response, in addition to humoral and cellular immune responses, against pathogens where mucosal immunity plays a major role in protection.

Example 5

Generation of Cell Lines Transformed with the BAV3 E1 Sequences

MDBK cells in monolayer cultures were transfected with pSM71-neo, pSM61-kan1 or pSM61-kan2 by a lipofection-mediated transfection technique (GIBCO/BRL, Life Technologies, Inc., Grand Island, N.Y.). At 48 h after transfection, cells were maintained in the MEM supplemented with 5% fetal bovine serum and 700 µg/ml G418. The medium was changed every 3 rd day. In the presence of G418, only those cells would grow which have stably incorporated the plasmid DNA used in transfection experiments into their genomes and are expressing the neo$^r$ gene. The cells which have incorporated the neo$^r$ gene might also have taken up the BAV3 E1 sequences and thus expressing BAV3 E1 protein/s. A number of neo$^r$ (i.e., G418-resistant) colonies were isolated, expended and tested for the presence of BAV3 E1 message/s by Northern blot analyses using a DNA probe containing only the BAV3 E1 sequences. Expression of BAV3 E1 protein/s were confirmed by a complimentation assay using a HAd5 deletion mutant defective in E1 function due to an E1 deletion.

Fetal bovine kidney cells in monolayers were also transfected with pSM71-neo, pSM61kan-1 or pSM61-kan2 by the lipofection-mediated transfection technique, electroporation (Chu et al (1987) *Nucl. Acids Res.* 15:1311–1326), or calcium phosphate precipitation technique (Graham et al (1973) *Virology* 52:456–467). Similarly, a number of G418-resistant colonies were isolated, expended and tested for the presence of BAV3 E1 gene products as mentioned above.

Example 6

Generation of a BAV3 Recombinant Containing the Beta-galactosidase Gene as an E1 Insert As E1 gene products are essential for virus replication, adenovirus recombinants containing E1 inserts will grow only in a cell line which is transformed with the adenovirus E1 sequences and expresses E1. A number of cell line which are transformed with the BAV3 E1 sequences were isolated as described earlier. The technique of foreign gene insertions into the E1 regions is similar to the gene insertion into the E3 region of the BAV3 genome, however, for insertion into E1 there is a need of an E1 transfer plasmid which contains DNA sequences from the left end of the BAV3 genome, an appropriate deletion and a cloning site for the insertion of foreign DNA sequences. G418-resistant MDBK cell monolayers were cotransfected with the wild-type (wt) BAV3 DNA and pSM71-Z following the lipofection-mediated-transfection procedure (GIBCO/BRL, Life Technologies, Inc., Grand Island, N.Y.). The monolayers were incubated at 37° C. under an agarose overlay. After a week post-incubation an another layer of overlay containing 300 ug/ml Blu-gal™ (GIBCO/BRL Canada, Burlington, Ontario, Canada) was put onto each monolayer. The blue plaques were isolated, plaque purified and the presence of the beta-galactosidase gene in the BAV3 genome was identified by agarose gel electrophoresis of recombinant virus DNA digested with suitable restriction enzymes and confirmed by beta-galactosidase assays using extracts from recombinant virus infected cells.

Deposit of Biological Materials

The following materials were deposited and are maintained with the Veterinary Infectious Disease Organization (VIDO), Saskatoon, Saskatchewan, Canada.

The nucleotide sequences of the deposited materials are incorporated by reference herein, as well as the sequences of the polypeptides encoded thereby. In the event of any discrepancy between a sequence expressly disclosed herein and a deposited sequence, the deposited sequence is controlling.

| Material | Internal Accession No. | Deposit Date |
|---|---|---|
| Recombinant plasmids | | |
| pSM51 | pSM51 | Dec. 6, 1993 |
| pSM71 | pSM71 | Dec. 6, 1993 |
| Recombinant cell lines | | |
| MDBK cells transformed with BAV3 E1 sequences (MDBK-BAVE1) | | Dec. 6, 1993 |
| Fetal bovine kidney cells transformed with BAV3 E1 sequences(FBK-BAV-E1) | | Dec. 6, 1993 |

While the present invention has been illustrated above by certain specific embodiments, the specific examples are not intended to limit the scope of the invention as described in the appended claims.

What is claimed is:

1. A replication-defective recombinant bovine adenovirus (BAV) expression vector comprising a bovine adenovirus genome with a deletion of all or part of the E1 region;
   said expression vector further comprising an insertion, at the site of the deletion, of a non-BAV nucleotide sequence under the control of an effective promoter.

2. The recombinant BAV expression vector of claim 1 further comprising a deletion of part or all of the E3 region.

3. The recombinant BAV expression vector of claim 2 comprising an insertion at the site of the E3 deletion, of one or more non-BAV nucleotide sequences, said non-BAV nucleotide sequences being under the control of one or more effective promoters.

4. The replication-defective recombinant BAV expression vector of claim 1 wherein the non-BAV nucleotide sequence is a mammalian sequence.

5. The replication-defective recombinant BAV expression vector of claim 1 wherein the non-BAV nucleotide sequence is a human sequence.

6. A method for introducing and expressing a non-BAV nucleotide sequence in a mammalian cell, wherein the method comprises contacting said mammalian cell with the replication-defective recombinant BAV expression vector according to claim 1.

7. A method for introducing and expressing a non-BAV nucleotide sequence in a mammalian cell, wherein the method comprises contacting said mammalian cell with the replication-defective recombinant BAV expression vector according to claim 3.

8. The method according to claim 6, wherein the non-BAV nucleotide sequence is a mammalian sequence.

9. The method according to claim 6, wherein the non-BAV nucleotide sequence is a human sequence.

10. The vector of claim 1 wherein said BAV is BAV subgroup 1.

11. A replication-defective recombinant bovine adenovirus (BAV) comprising a bovine adenovirus subgroup 1 genome with a deletion of part or all of the E1 multiple gene coding region, said deletion being replaced by a heterologous nucleotide sequence coding for a polypeptide produced by a disease causing organism or an antigenic determinant produced by a disease causing organism, wherein said heterologous nucleotide sequence is in association with an effective promoter.

12. The recombinant BAV of claim 11 further comprising a deletion of part or all of E3.

13. A method for eliciting an immune response in a mammalian host to protect against an infection comprising administering a vaccine composition comprising,
   (a) a replication-defective recombinant BAV of claim 11 wherein the heterologous nucleotide sequence encodes an antigenic determinant produced by a disease organism; and
   (b) a pharmaceutically acceptable excipient.

14. A vaccine for protecting a mammalian host against infection comprising:
   (a) a replication-defective recombinant BAV of claim 11 wherein the beterologous nucleotide sequence encodes an antigenic determinant produced by a disease organism; and
   (b) a phannaceutically acceptable excipient.

15. A replication-defective recombinant bovine adenovirus vector (BAV) comprising a bovine adenovims subgroup 1 gename wherein part or all of the E1 multiple gene coding region and part or all of the E3 multiple gene coding region are deleted and a heterologous nucleotide sequence encoding a foreign protein or fragment thereof is inserted into at least one of the deletions.

16. The vector of claim 11 which is a bovine adenovirus type 3.

17. The vector of claim 15 which is a bovine adenovirus type 3.

* * * * *